United States Patent [19]

Heck et al.

[11] Patent Number: 4,952,397
[45] Date of Patent: Aug. 28, 1990

[54] 2-QUATERNARY HETEROARYLALKYLTHIO CARBAPENEMS HAVING AN ACID MOIETY SUBSTITUENT

[75] Inventors: James V. Heck, Scotch Plains; Ronald W. Ratcliffe, Matawan, both of N.J.

[73] Assignee: Merck & Co., Inc., Rahway, N.J.

[21] Appl. No.: 275,811

[22] Filed: Nov. 23, 1988

Related U.S. Application Data

[63] Continuation-in-part of Ser. No. 744,740, Jun. 17, 1985, abandoned, and a continuation-in-part of Ser. No. 744,741, Jun. 17, 1985, abandoned, and a continuation-in-part of Ser. No. 123,494, Nov. 10, 1987.

[51] Int. Cl.$^5$ .................... C07D 487/04; A61K 31/40
[52] U.S. Cl. ..................... 424/114; 540/350; 514/210
[58] Field of Search .............. 540/350; 514/210; 424/114

[56] References Cited

U.S. PATENT DOCUMENTS 4,552,696 11/1985 Kim et al. ............... 540/350
4,680,292 7/1987 Christenson et al. ............... 540/350

Primary Examiner—Nicholas S. Rizzo
Attorney, Agent, or Firm—Raymond M. Speer; Hesna J. Pfeiffer

[57] ABSTRACT

Compounds of the formula:

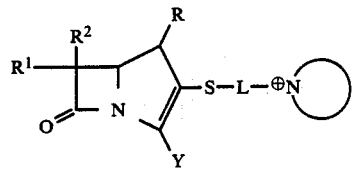

wherein

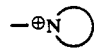

is a quaternized, monocyclic or bicyclic heteroaryl group, substituted by an acid moiety, and their preparation and use as antibiotics are disclosed.

13 Claims, No Drawings

2-QUATERNARY HETEROARYLALKYLTHIO CARBAPENEMS HAVING AN ACID MOIETY SUBSTITUENT

REFERENCE TO RELATED APPLICATIONS

This application is a continuation-in-part of U.S. patent application Ser. Nos. 744,740 and 744,741, both filed June 17, 1985, both now abandoned; and of Ser. No. 123,494, filed Nov. 20, 1987.

BACKGROUND OF THE INVENTION

The present invention is concerned with improved carbapenem antibiotics characterized by having a monocyclic or bicyclic quaternary heteroarylalkylthio substituent in the 2-position. The heteroaryl portion of the substituent is further substituted with an acidic moiety.

Thienamycin is a known carbapenem, broad spectrum antibiotic of the formula:

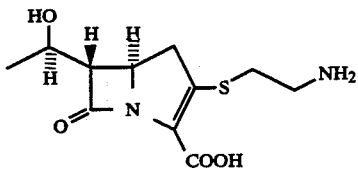

A

Other derivatives of A are also known. The present quaternary, monocyclic or bicyclic heteroarylalkylthio substituted carbapenems have an antibiotic spectrum similar to or better than A. The present carbapenems also exhibit reduced seizure potential, i.e., less tendency to produce convulsions, when compared to the N-formimidoyl and N-acetimidoyl derivatives of A, and to related quaternary, monocyclic or bicyclic heteroarylalkylthio substituted carbapenems that lack the additional acidic moiety in the heteroaryl group.

U.S. Pat. No. 4,552,696 (Kim and Misco) discloses carbapenem antibiotics having a 2-sidechain of the formula

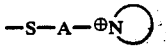

wherein a possible substituent of the heteroaryl group is carboxyl. However, this carboxyl substituent is only one of a vast number of other enumerated substituents, and no special significance of any kind is attached to it. Furthermore, the patent disclosure contains data relating to "Toxicity After Intracranial Administration to Mice" and thus demonstrates an awareness of the problem of convulsive potential. Yet, there is no appreciation that an acidic moiety in the heteroaryl group, which makes the carbapenem compound overall an anionic zwitterion, will uniformly confer a significantly reduced tendency to produce convulsions in the overall compound.

SUMMARY OF THE INVENTION

The present invention provides novel carbapenem compounds of the formula:

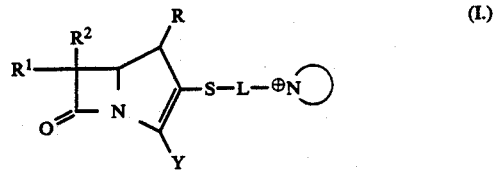

(I.)

wherein R is H or $CH_3$; $R^1$ and $R^2$ are independently H, $CH_3-$, $CH_3CH_2-$, $(CH_3)_2CH-$, $HOCH_2-$, $CH_3CH(OH)-$, $(CH_3)_2C(OH)-$, $FCH_2-$, $F_2CH-$, $F_3C-$, $CH_3CH(F)-$, $CH_3CF_2-$, or $(CH_3)_2C(F)-$;

is a quaternary, monocyclic or bicyclic, substituted heteroaryl group containing (a) when monocyclic, up to 4 heteroatoms and up to 6 total ring atoms or (b) when bicyclic up to 6 heteroatoms and 9–10 ring atoms. The heteroaryl group is required to be substituted by an acidic sidechain of the structure $-B$ or $-(CH_2)_n-X-(CH_2)_m-W-B$ where:

n is 0–4;
m is 0–4,;
x is $CR^sR^t$; $CH=CH$; phenylene ($-C_6H_4-$); NH; $N(C_1-C_4$ alkyl); O; S; S=O; C=O; $SO_2$; $SO_2NH$; $CO_2$; CONH; $OCO_2$; OC=O; or NHC=O; where $R^t$ is H or $C_1-C_4$-alkyl; and $R^s$ is H, OH, $C_1-C_4$ alkyl, $O(C_1-C_4$ alkyl), $NH_2$, $NH(C_1-C_4$ alkyl), $N(C_1-C_4$ alkyl)$_2$, CN, $CONH_2$, $CON(C_1-C_4$ alkyl)$_2$, $CO_2H$, $SO_2NH_2$, or $SO_2NH(C_1-C_4$ alkyl);
W is a single bond; NH; $N(C_1-C_4$ alkyl); O; or S;
B is an acidic function selected from carboxy ($CO_2H$); phosphono [$P=O(OH)_2$]; alkylphosphono {$P=O(OH)-[O(C_1-C_4$ alkyl)]}; alkylphosphinyl [$P=O(OH)-(C_1-C_4$alkyl)]; phosphoramido [$P=O(OH)NH_2$]; substituted phosphoramido [$P=O(OH)NH(C_1-C_4$alkyl) and $P=O(OH)NHR^x$]; sulfino ($SO_2H$); sulfo($SO_3H$); 5-tetrazolyl ($CN_4H$); arylsulfonamido ($SO_2NHR^x$); $CONHR^y$; $SO_2NHR^y$ and acylsulfonamido selected from the structures $CONHSO_2R^x$, $CONHSO_2NH_2$, $CONHSO_2$ ($C_1-C_4$alkyl), $CONHSO_2NH(C_1-C_4$alkyl), $CONHSO_2N(C_1-C_4$alkyl)$_2$, $SO_2NHCO(C_1-C_4$ alkyl), $SO_2NHCONH_2$, $SO_2NHCONH(C_1-C_4$-alkyl), $SO_2NHCON(C_1-C_4$alkyl)$_2$, $SO_2NHCOR^x$, $SO_2NHCN$, $SO_2NHCSNH_2$, $SO_2NHCSNH$ ($C_1-C_4$ alkyl), $SO_2NHCSN(C_1-C_4$ alkyl)$_2$, $SO_2NHSO_2R^x$, and $SO_2NHSO_2R^w$, where $R^x$ is substituted or unsubstituted phenyl, naphthyl, or heteroaryl; $R^w$ is $C_1-C_4$ alkyl, $NH_2$, $NH(C_1-C_4$ alkyl), $N(C_1-C_4$ alkyl)$_2$, OH, or $O(C_1-C_4$ alkyl); and $R^y$ is OH, SH, $O(C_1-C_6$ alkyl), $S(C_1-C_6$ alkyl), O-phenyl, S-Phenyl, O-heteroaryl, S-heteroaryl; where for $R^x$ and $R^y$ heteroaryl means (a) a monocyclic group having 5 or 6 total ring atoms in which from 1 to 4 carbon ring atoms are replaced by heteroatoms selected from N, O, and S, or (b) a bicyclic group having 9 or 10 total ring atoms in which from 1 to 6 carbon ring atoms are replaced by heteroatoms selected from N, O, and S; and where for $R^x$ and $R^y$ the phenyl, naphthyl, and heteroaryl groups may be further mono- or disubstituted by groups independently selected from $C_1-C_4$ alkyl; $C_1-C_4$-alkoxy; Br; Cl; F;

CF₃; OH; (C₁-C₄ alkyl)carbonyloxy; carbamoyl, carbamoyloxy, sulfamoyl, and amino where the nitrogen may be unsubstituted or mono- or disubstituted with C₁-C₄ alkyl; C₁-C₄ alkylthio; C₁-C₄ alkylsulfinyl; C₁-C₄ alkylsulfonyl; formylamino; (C₁-C₄ alkyl)carbonylamino; (C₁-C₄alkoxyl)-carbonylamino; ureido in which the terminal nitrogen may be unsubstituted or substituted by C₁-C₄ alkyl; (C₁-C₄ alkyl)sulfonamido; cyano; (C₁-C₄alkoxyl)carbonyl; thiocarbamoyl; nitro; carboxyl; formyl; and (C₁-C₄ alkyl)carbonyl.

In addition, the heteroaryl group

is optionally substituted by one to three of the radicals independently selected from the group consisting of:
(a) a trifluoromethyl group: —CF₃;
(b) a halogen atom: —Br, —Cl, —F, or —I;
(c) C₁-C₄ alkoxy radical: —OC₁₋₄alkyl;
(d) a hydroxy group: —OH;
(e) (C₁-C₆alkyl) carbonyloxy radical:

(f) a carbamoyloxy radical which is unsubstituted or substituted on nitrogen with one or two C₁-C₄ alkyl groups:

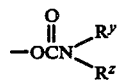

where $R^y$ and $R^z$ are independently H or C₁₋₄alkyl;
(g) a C₁-C₆alkylthio radical, C₁-C₆alkylsulfinyl radical or C₁-C₆alkylsulfonyl radical:

alkyl where n=0-2;
(h) a sulfamoyl group which is unsubstituted or substituted on nitrogen by one or two C₁-C₄ alkyl groups:

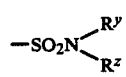

where $R^y$ and $R^z$ are as defined above;
(i) an amino group, or a mono (C₁-C₄alkyl) amino or di(C₁-C₄ alkyl)-amino group:

where $R^y$ and $R^z$ are as defined above;
(j) a formylamino group:

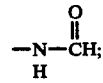

(k) substituted or unsubstituted (C₁-C₆ alkyl)carbonylamino radical:

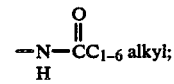

(l) a (C₁-C₄alkoxy) carbonylamino radical:

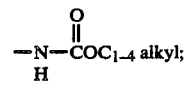

(m) a ureido group in which the terminal nitrogen is unsubstituted or substituted with one or two C₁-C₄ alkyl group:

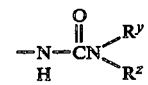

where $R^y$ and $R^z$ are as defined above;
(n) a C₁-C₆ alkyl sulfonamido group:

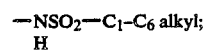

(o) a cyano group: —CN;
(p) a formyl or acetalized formyl radical:

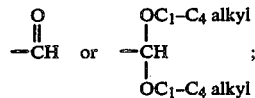

(q) (C₁-C₆ alkyl)carbonyl radical:

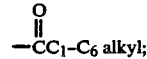

(r) substituted or unsubstituted phenylcarbonyl or heteroarylcarbonyl:

(s) a hydroximinomethyl radical in which the oxygen or carbon atom is optionally substituted by a C₁-C₄ alkyl group:

where $R^y$ and $R^z$ are as defined above;
(t) a (C₁-C₆ alkoxy)carbonyl radical:

(u) a carbamoyl radical which is unsubstituted or substituted on nitrogen by one or two $C_1-C_4$ alkyl groups:

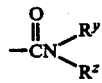

where $R^y$ and $R^z$ are as defined above;
(v) an N-hydroxycarbamoyl or N($C_1-C_4$ alkoxy)carbamoyl radical in which the nitrogen atom may be additionally substituted by a $C_1-C_4$ alkyl group:

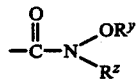

where $R^y$ and $R^z$ are as defined above;
(w) a thiocarbamoyl group:

(x) an amidino group

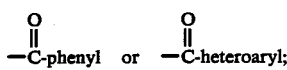

where $R^5$, $R^6$ and $R^7$ are independently hydrogen, $C_1-C_4$ alkyl or wherein two of the alkyl groups together form a $C_2-C_6$ alkylene radical optionally interrupted by a heteroatom and joined together to form a ring;
(y) a guanidinyl group where $R^5$ in (x) above is $NR^8R^9$ and $R^8$ and $R^9$ are as defined for $R^5$ through $R^7$ above;
(z) a carbamimidoyl group

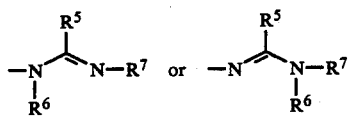

where $R^5$, $R^6$ and $R^7$ are as defined above;
(aa) a $C_2-C_6$ alkenyl radical;
(ab) a $C_2-C_6$ alkynyl radical;
(ac) a $C_3-C_7$ cycloalkyl radical;
(ad) a $C_5-C_7$ cycloalkenyl radical;
(ae) a substituted or unsubstituted phenyl or heteroaryl group;
(af) a sulfo group: $-SO_3H$;
(ag) a carboxy group: $-COOH$;
(ah) $C_1-C_6$ alkyl radical; and·
(ai) $C_1-C_4$ alkyl monosubstituted by one of the substituents (a)-(ag) above;
wherein for those radicals above which are indicated to be optionally substituted, the substituents are one or two in number and independently selected from hydroxy, $C_1-C_4$ alkoxy, mercapto, amino, mono- or di($C_1-C_4$ alkyl)amino, cyano, halo, $CF_3$, COOH, sulfo, carbamoyl, and sulfamoyl;

L is a substituted or unsubstituted, straight or branched chain, bivalent $C_1-C_6$ alkyl, $C_2-C_6$ alkenyl or $C_3-C_6$ cycloalkyl, or $C_1-C_4$ alkyl-X—$C_1-C_4$ alkyl wherein X is O, S, NH, or N($C_{1-4}$ alkyl), wherein the substituents are selected from radicals (a) through (ai) defined above;

together, in addition to the individual definitions of L and

above, may be the group

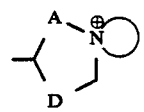

where

is a 5- to 6-membered heteroaryl group containing from one to three heteroatoms which is substituted by an acidic moiety, and which is optionally substituted by one or more members independently selected from the group consisting of the substituents defined as (a)-(ai) under

and A and D are independently selected from a direct bond or a substituted or unsubstituted $C_1-C_4$ alkylene group optionally interrupted by a heteroatom; provided that, A and D cannot both be a direct bond, and that the ring containing A and D contains from 5 to 8 atoms; and wherein the substituents on A and D are selected from hydroxyl, $C_1-C_3$alkoxy, amino, carboxyl, cyano, carbamoyl, trifluoromethyl, $C_1-C_4$ alkyl, and di($C_1-C_4$ alkyl)amino; and
Y is selected from:
 (i) COOH or a pharmaceutically acceptable ester or salt thereof,
 (ii) $COOR^3$ wherein $R^3$ is a readily removable carboxyl covering group,
 (iii) COOM wherein M is an alkali metal, or
 (iv) $COO\ominus$, provided that an additional compensating cationic group is present in the structure.

The most common Y group of the present invention is COOM wherein M is a metal cation such as Na, K, or ½ Ca. Since the heteroarylium group is substituted by an acidic substituent which is predominantly ionized, that is anionic, at or near neutral PH in aqueous solution, the Y group is usually of the salt form COOM. In structural terms wherein B⊖ represents the ionized or anionic form of the acidic group, the compounds of the present invention can be represented as shown below wherein all charges are compensated for.

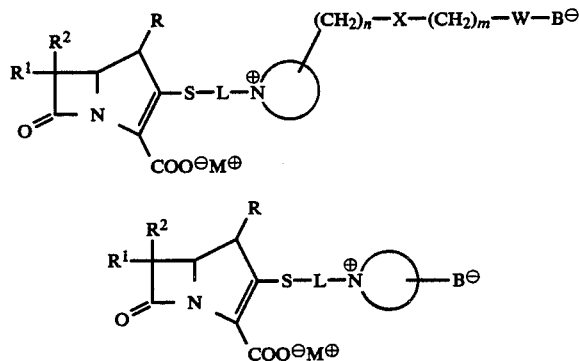

It should be noted that it is possible for the M group to be located at either the carboxyl or B center as long as the net charge of the compound remains zero. Compounds of this type are referred to as anionic zwitterions since that is the overall charge type of the molecule when excluding the external M cation. If the compound where additionally substituted by a cationic group such as an ammonium substituent, the compensatory, M group would not be required and the compound would be a double zwitterion.

The substituent R=methyl may be of either configuration, i.e., the α or β-stereoisomer. The β- stereoisomer is preferred, since it has been found that this configuration gives improved stability toward the DHP-I enzyme.

The

group must have an acidic sidechain but m optionally have from 1 to 3 additional substituents which may be the same or different and are selected on an independent basis. While a single such additional substituent is usually preferred, there is occasion to use up to three such substituents, e.g., where it is desired to enhance the effect of a particular substituent group by employing multiple substituents. Thus, two sulfomethyl substituents may be used. At other times it may be desired to employ a substituent known to enhance antibacterial activity of the overall molecule against a particular bacterium, for example, while also employing a substituent known to improve the duration of action of the overall molecule.

With reference to the above definitions, "alkyl" means a straight or branched chain aliphatic hydrocarbon radical.

The term "heteroatom" means N, S, or O, selected on an independent basis.

Under the definition of "Y", the term "pharmaceutically acceptable ester or salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of raw materials, ease of crystallization, yield, stability, hygroscopicity, and flowability of the resulting bulk drug. Since the compounds of the present invention may be carboxylates, the salts would be cations such as benzathine, chloroprocaine, choline, diethanolamine, meglumine and procaine. The metallic cations such as aluminum, calcium, lithium, magnesium and zinc are potential choices. The alkali metal cations sodium and potassium are specifically defined.

The term "readily removable carboxyl covering group" means a conventional substituent which takes the place of the acidic hydrogen of the carboxyl group and thereby prevents said group from reacting with any of the reagents employed in the various steps of the overall synthesis. Such covering of the carboxyl group is often necessary to prevent unwanted competing reactions involving said carboxyl group from taking place. Thus, all of these compounds are intermediates. The conventional covering substituent must also be "readily removable", by which is meant that it is selectively removable, i.e., it is not likely to be removed during the course of ordinary procedures which are to be carried out on the carbapenem nucleus and sidechains, while, on the other hand, it is likely to be removed by procedures which are not so harsh as to disturb the basic ring structure of the carbapenem nucleus or unprotected substituents thereon.

It is preferred that when one of $R^1$ or $R^2$ is H, the other is (R)CH₃CH(OH)— or (R)CH₃CH(F)—; and (R)CH₃CH(OH)— is most preferred.

A preferred group of compounds of Formula I are those where L is $C_1-C_6$ branched or linear alkyl, both substituted and unsubstituted. The preferred substituents are OH, CF₃, OC₁₋₄ alkyl, CN, CONH₂, CONH(- C₁-C₄ alkyl), CON(C₁-C₄ alkyl)₂, COOH, NH₂, NH(C₁-C₄ alkyl), and N(C₁-C₄ alkyl)₂ and especially OCH₃, OH, NH₂, and CF₃. Examples of preferred L groups are —CH₂—, —CH(CH₃)—, —CH(CH₂CH₃)—, —CH(CH₂OCH₃), —CH₂—CH₂—, —CH(CH₃)—CH₂—, —CH(CH₂CH₃)—CH₂—, —C(CH₃)₂—CH₂—, —(CH₂)₃—, —CH(CH₃)—(CH₂)₂—, CH₂—CH(CH₃)—, —CH₂—C(CH₃)₂—CH₂—, —(CH₂)₄—, —CH(CF₃)—CH₂—, —CH(CH₂OH)—CH₂—, —CH(CH₂NH₂)—CH₂—, —CH(CH₂OCH₃)—CH₂—, and the like.

Especially preferred compounds of Formula I compounds are those where L is —CH₂—, —CH₂CH₂— or —CH(CH₃)CH₂—. Of course it is understood that where any substituent group has an asymmetric center e.g.

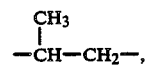

then all stereoisomers are included as mixtures or as separate isomers.

In the preferred embodiment, the

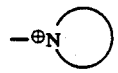

group is quaternized, monocyclic heteroaryl, substituted by an acidic group and optionally substituted by one or more additional substituents, containing in addition to the quaternary N, up to 2 additional hetero atoms selected from O, N and S.

Representative useful monocyclic

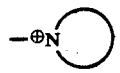

groups are substituted pyridinium, pyridazinium, pyrimidinium, pyrazinium, pyrazolium, triazolium, imidiazolium, thiazolium, oxazolium, isoxazolium and the like.

The pyridinium group is most preferred since it provides, when incorporated into the carbapenem final product, the desired properties of good antibacterial spectrum and potency combined with chemical stability. It also provides ready availability and ease of handling as a starting material. However, any of the other groups set out above, as well as those falling within the definition of

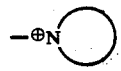

set out herein but not specifically described above, are also suitable, although perhaps in some cases less desirable in terms of one or more of the criteria mentioned above.

Preferred Formula I compounds are those where monocyclic

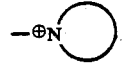

is a six membered heteroaryl, such as substituted pyridinium, pyridazinium or pyrazinium, and preferably substituted pyridinium, wherein the acidic moiety is selected from COOH, ($C_1$-$C_4$ alkyl)COOH, $SO_3H$, ($C_1$-$C_4$ alkyl) $SO_3H$, $SO_2NH$(heteroaryl), ($C_1$-$C_4$ alkyl) $SO_2NH$ (heteroaryl), and ($C_1C_4$ alkyl) $SO_2NHCN$; and the optional substituents (one to three) are selected from OH, $NH_2$, $NHCH_3$, $OCH_3$, $COO$—$C_1$-$C_3$ alkyl, C(O)NHOH, phenyl,N($CH_3$)$_2$, C(O)$CH_3$, C(O)N(CH$_3$)OH, $SO_3H$, $SCH_3$, CHO, COOH, S(O)$CH_3$, $SO_2CH_3$, $SO_2NH_2$, $SO_2NHCH_3$, $SO_2CH_3$, CN, $CSNH_2$, Cl, F, Br, $CF_3$, $CONH_2$, $CONH(CH_3)$, CH=N—OH, $C_1$-$C_6$ alkenyl and substituted and unsubstituted $C_1$-$C_6$ alkyl.

The most preferred acidic moieties are $SO_3H$, $CH_2SO_3$, $CH_2CH_2SO_2NH$(heteroaryl), and $CH_2SO_2NHCN$; and the most preferred optional substituents are $C_1$-$C_6$ alkyl, $NH_2$, $NHCH_3$, $OCH_3$, Cl, F, Br, $CF_3$, N($CH_3$)$_2$, $SCH_3$, S(O)$CH_3$, $SO_2CH_3$, $SO_2NH_2$, $SO_2NHCH_3$, CN, $CSNH_2$, CH=N—OH, $CONH_2$, $CONH(CH_3)$.

The compounds of the present invention are characterized by having an acidic substituent on the N-containing mono- or bicyclic quaternary heteroaryl group in the 2-position. The acidic substituent forms an anion under physiologic conditions of pH, and this anionic site, combined with the quaternary nitrogen center and the carboxylate group, lead to compounds that are overall anionic zwitterions. This novel characteristic has been found to result in at least one surprising and important improvement in the biological properties of the compounds, reduced CNS side-effects. A more particular group of the compounds, those wherein the acidic function is a sulfoalky group of the formula $CH_2SO_3H$, $CH_2SO_2NH$ (heteroaryl), or $CH_2SO_2NHCN$, have been found to have the additional surprising and important biological property of enhanced potency against Pseudomonas species, an especially important nosocomial pathogen. In this most preferred group of compounds, it is preferred that the N-containing mono- or bicyclic quaternary heteroaryl group in the 2-position is pyridinium, the linking moiety L is —$CH_2CH_2$—, and the acidic substituent is $CH_2SO_3H$, $CH_2SO_2NH$(heteroaryl), or $CH_2SO_2NHCN$.

An especially preferred subgenus of compounds within the scope of the present invention are 2-[4-(N-cyanosulfamoylmethyl)-1-pyridinium] ethylthio carbapenems of the following formula:

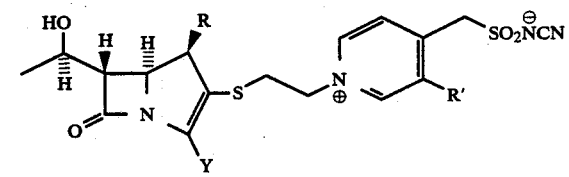

where
R is H or $CH_3$;
R' is H, F, Cl, $NH_2$, $CH_3$, $SO_2NHCH_3$, $SO_2NH_2$, $SO_2CH_3$, $OCH_3$, $CONH_2$, S(O)$CH_3$, or $CONHCH_3$; and
Y is as defined above.

Within this subgenus, the preferred compounds are those wherein R is H and R' is H, F, or Cl.

Representative examples of preferred

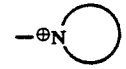

pyridinium groups and substituents are those having the following formulas:

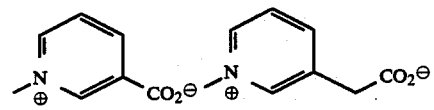

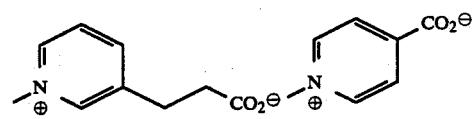

11
-continued
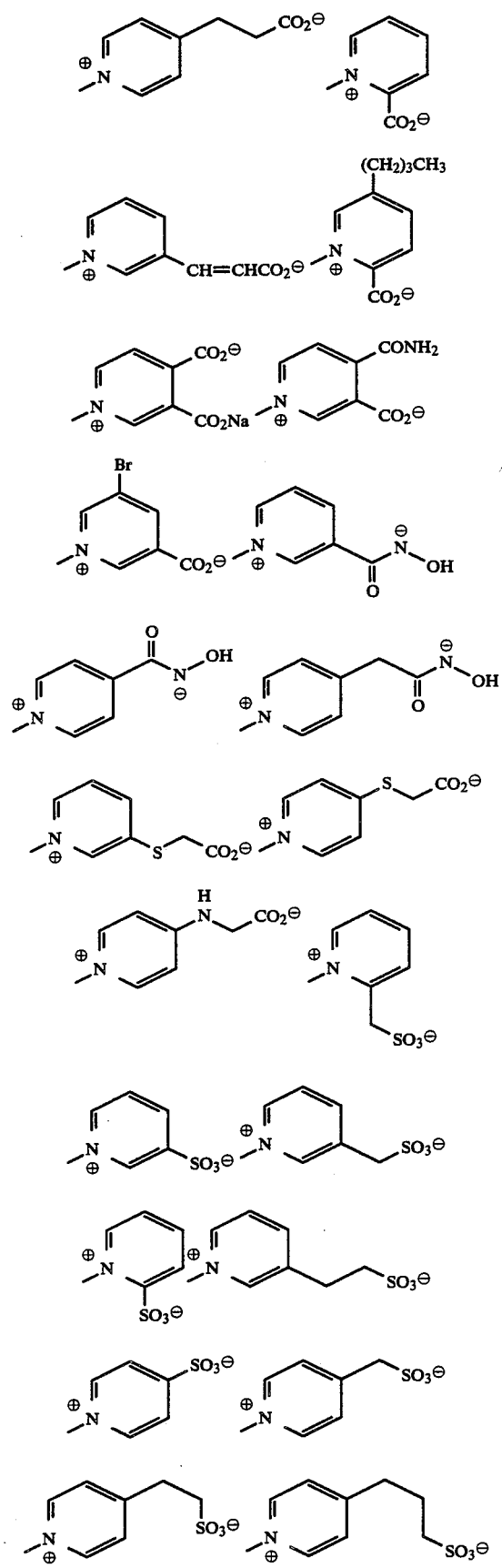
12
-continued
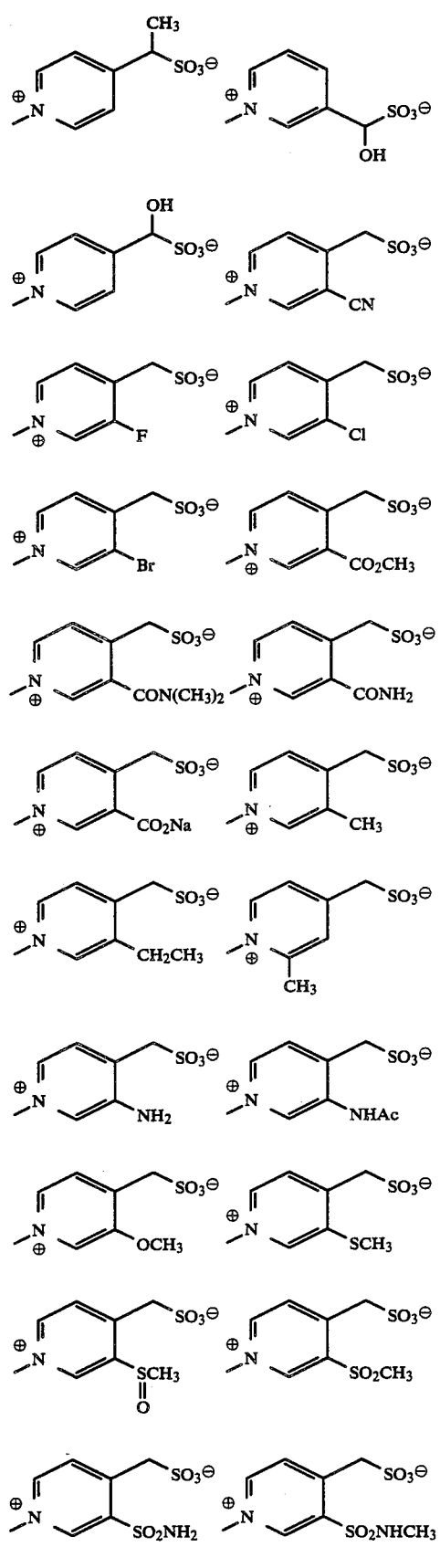

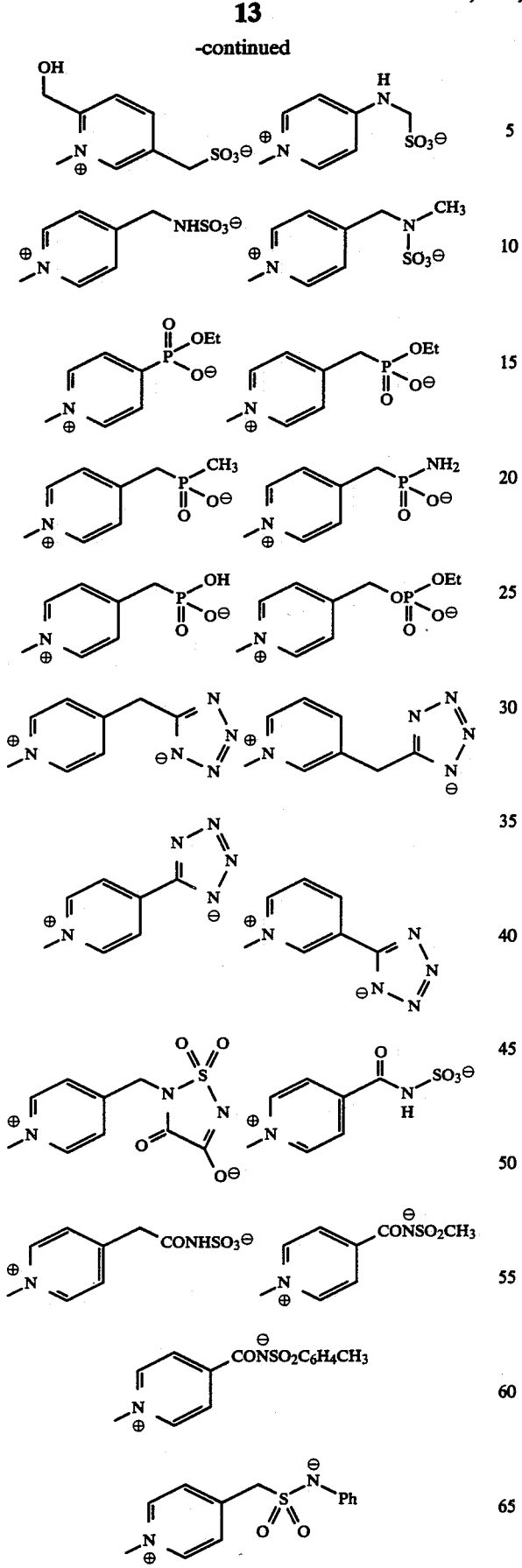
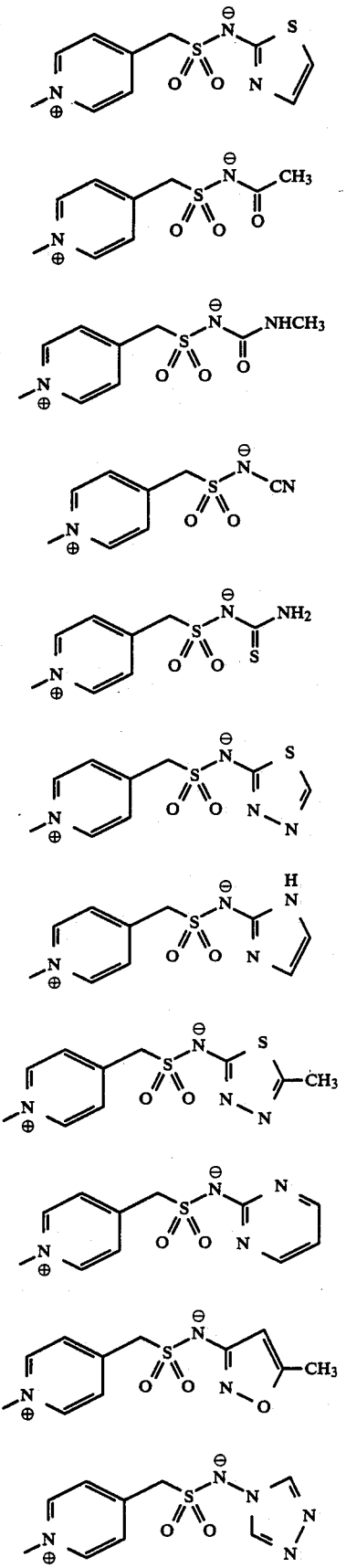

-continued
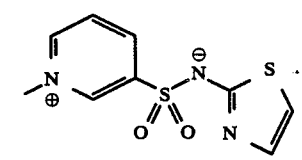
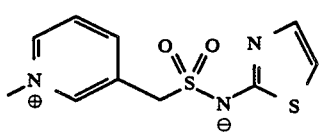
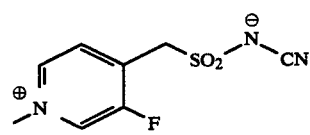
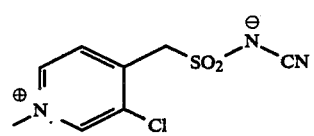
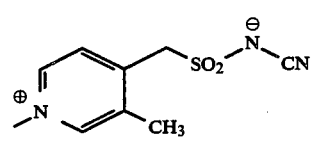
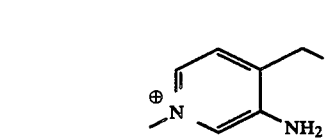
Especially preferred compounds are those of structure Ia wherein R is H or CH₃ and the heteroarylium moiety
is selected from the groups shown below:
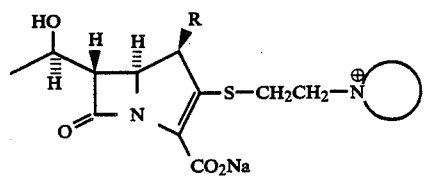
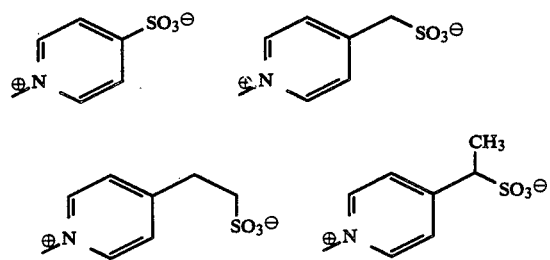
-continued
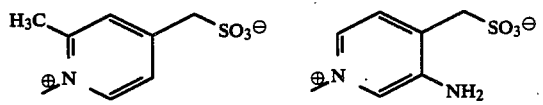
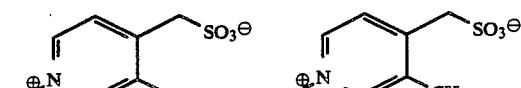
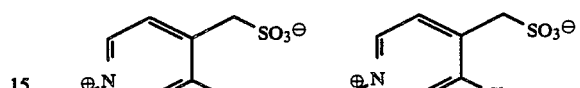
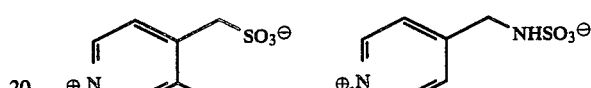
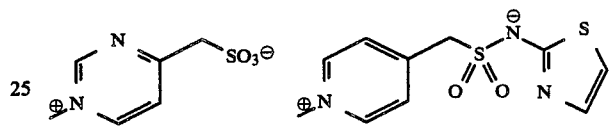
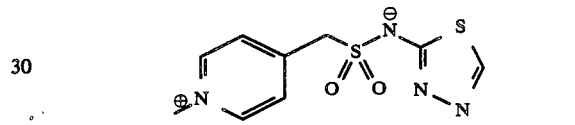
Representative examples of preferred monocyclic
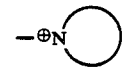
other than pyridinium, with preferred substituents, are those having the following formulas:
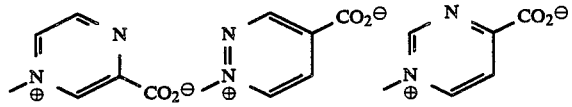
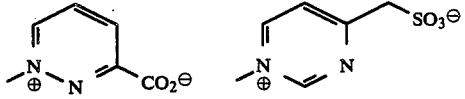

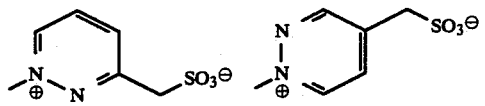
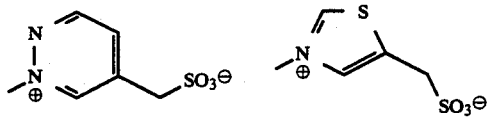
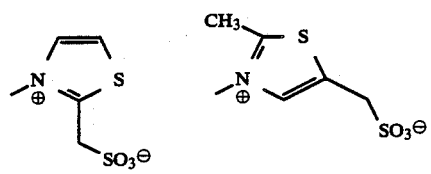
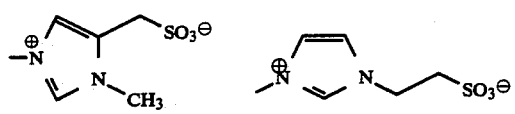
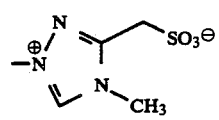

In another preferred embodiment, the

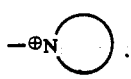

group is a quaternized, bicyclic, heteroaryl substituted by an acidic group, and containing in addition to the quaternary N, up to 5 additional heteroatoms independently selected from O, N and S, and 9-10 total ring atoms.

Representative useful

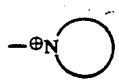

groups are substituted and unsubstituted quinolinium,, isoquinolinium, quinoxalinium, isocinolinium, thienopyridinium, furopyridinium, naphthyridinium, pyrazinopyridinium

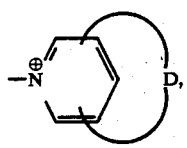

where D is $C_{2-6}$ alkylene ring which may be interrupted by one or more O, S or N heteroatoms.

Preferred Formula I compounds are those where

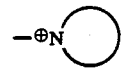

is a bicyclic 9 or 10 membered ring, and more preferably substituted quinolinium, isoquinolinium, or thienopyridinium.

In addition to the acidic group, which may be on either of the rings of the bicyclic heteroaryl, optionally one to three additional substituents may be present. The preferred additional substituents, as well as the preferred acidic groups, are the same as those for the monocylic heteroaryl groups, which have been described further above.

Representative examples of preferred bicyclic

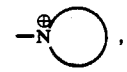

with preferred substituents, are those having the following formulas:

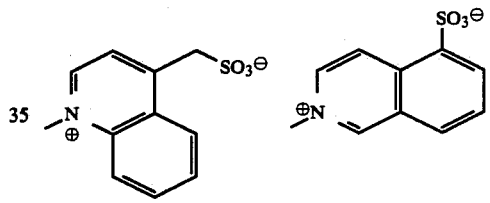
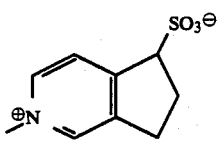
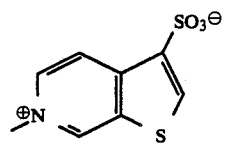
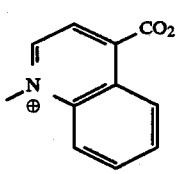
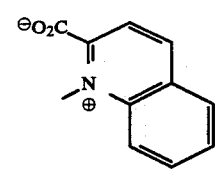
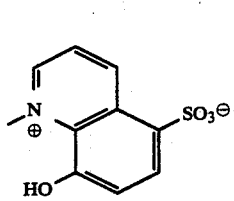
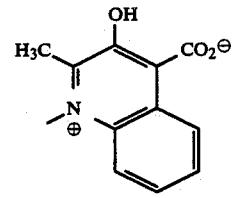
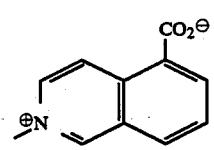
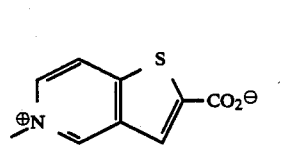

-continued

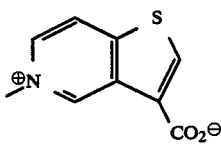

Where

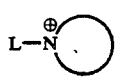 is 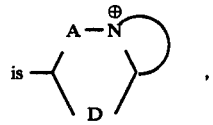, representative examples of preferred groups are:

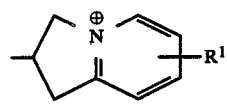

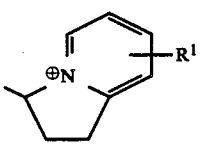

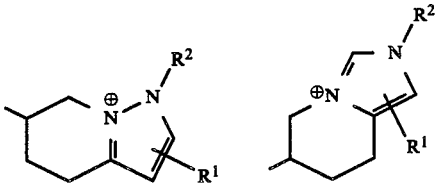

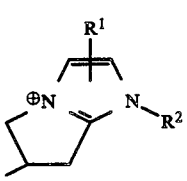 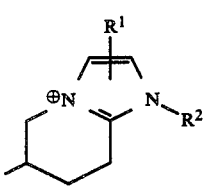

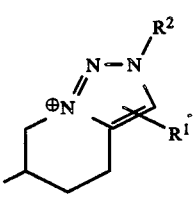

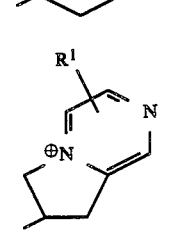

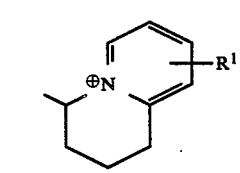 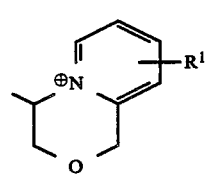

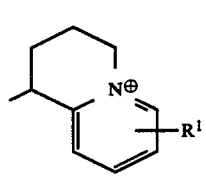 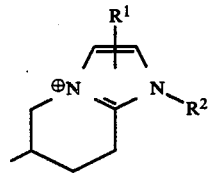

wherein $R^1$ is H or a suitable acidic substituent such as $CO_2H$, $SO_3H$, or $C_1$-$C_4$ alkyl substituted by $CO_2H$ or $SO_3H$ and $R^2$ is substituted or unsubstituted $C_1$-$C_4$ alkyl wherein the substituents are selected from OH, $N(C_1$-$C_3$ alkyl$)_2$, CN, $CONH_2$, and $O(C_1$-$C_4$ alkyl). Alternatively, $R^2$ can be a suitable acidic group such as $C_1$-$C_4$ alkyl substituted by $CO_2H$ or $SO_3H$ and $R^1$ is one of the optional substituents mentioned below.

The heteroarylium group may be optionally substituted by a group selected from $C_1$-$C_3$ alkyl, CN, $CONH_2$, $NH_2$, $NH(C_1$-$C_3$ alkyl), $N(C_1$-$C_3$alkyl$)_2$, OH, $O(C_1$-$C_4$ alkyl), $SO_2NH_2$, $CH_2N(C_1$-$C_3$ alkyl$)_2$, Br, F, $SO_2NH_2$, and $SO_2NH(C_{1-3}$ alkyl).

Especially preferred

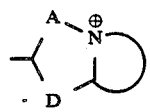

groups are where (a) A is $(CH_2)_2$ or $(CH_2)_3$, and D is a single bond, (b) A is $CH_2$ and D is $CH_2$ or $(CH_2)_2$, or (c) A is a single bond and D is $(CH_2)_{2-3}$, and the heteroaryl moiety is preferably pyridinium, thiazolium, or imidiazolium.

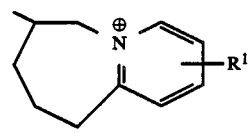 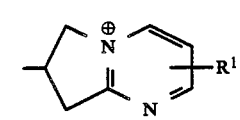

The compounds of Formula I include anionic zwitterion salts when Y is COOM:

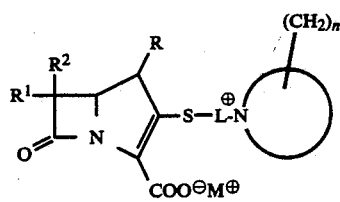

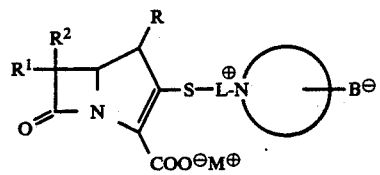

or, when Y is other than COOM, inner (zwitterionic) salts:

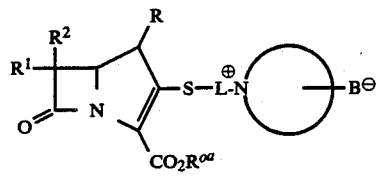

or

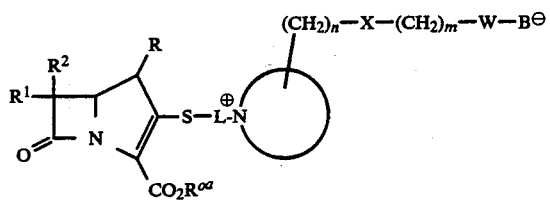

R°ᵃ is a pharmaceutically acceptable ester, e.g., pivaloyloxymethyl, phthalidyl, phthalimidomethyl, acetoxymethyl, ethoxycarbonyloxyethyl, pivaloyloxyethyl, 4-methyl-2-oxo-1,3-dioxolen-5-yl-methyl.

Again, the compounds of Formula I include the stereoisomers as mixtures and as separate isomers.

Compounds having the (5R,6S,8R) or (1R, 5S, 6S, 8R) stereochemistry shown below are preferred:

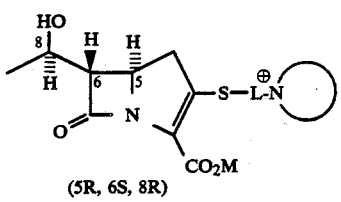
(5R, 6S, 8R)

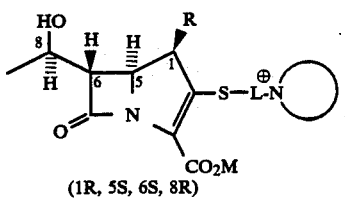
(1R, 5S, 6S, 8R)

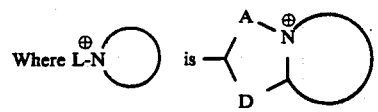

or when L contains a chiral center, the side chain chirality leads to diastereomeric products. The products can be separated by conventional methods, used as mixtures or synthesized stereospecifically from optically active mercaptans. Representative zwitterionic structures are shown below:

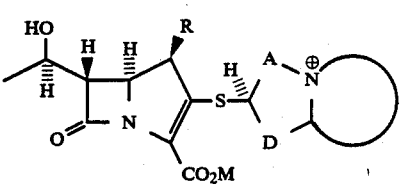

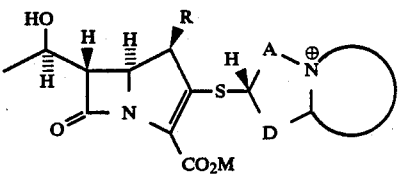

For many of the compounds exemplified in this specification, the R substituent is hydrogen. This is the result of a more facile synthesis for such compounds, however, and does not evidence any reference for R=hydrogen. To the contrary, the compounds wherein R=methyl will often be found to possess greater stability to dehydropeptidase (DHP-I) enzyme, a renal dipeptidase which mediates lactam hydrolysis of carbapenem compounds in man, resulting in significantly reduced urinary recoveries.

The carbapenem compounds of the present invention are useful per se and in their pharmaceutically acceptable salt and ester forms in the treatment of bacterial infections in animal and human subjects. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above include non-toxic acid addition salts. The Formula I compounds be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The pharmaceutically acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically acceptable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may also take the form where Y is $COOR^3$, where $R^3$ is a readily removable carboxyl covering group. Such conventional covering groups consist of known ester groups which are used to protectively cover the carboxyl group during the synthesis procedures described further below. These conventional covering groups are readily removable, i.e., they can be removed, if desired, by procedures which will not cause cleavage or other disruption of the remaining portions of the molecule. Such procedures include chemical and enzymatic hydrolysis, treatment with chemical reducing agents under mild conditions, and catalytic hydrogenation. Examples of such ester protecting groups include benzhydryl, p-nitrobenzyl, 2-naphthylmethyl, allyl, benzyl, trichloroethyl, silyl such as trimethylsilyl, phenacyl, p-methoxybenzyl, acetonyl, o-nitrobenzyl, 4-pyridylmethyl, and $C_1$–$C_6$ alkyl such as methyl, ethyl or t-butyl.

The compounds of the present invention are valuable antibacterial agents active against various Gram-positive and Gram-negative bacteria and accordingly find utility in human and veterinary medicine. Representative pathogens which are sensitive to the antibacterial agents of the present invention include various species of the following: Staphylococcus, Enterococcus, *Escherichia Coli*, Klebsiella, Enterobacter, Bacillus, Salmonella, Pseudomonas, Serratia and Proteus. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: typically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration—the parenteral route by injection being preferred for generalized infections. Such matters, however, are left to the routine discretion of the therapist according to principles of treatment well known in the antibacterial art. In general, a daily dosage consists of from about 5 to about 600 mg of active ingredient per kg of body weight of the subject in one or more treatments per day. A preferred daily dosage for adult humans lies in the range of from about 10 to 240 mg of active ingredient per kg of body weight. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10–60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compounds is parenteral by i.v. infusion, i.v. bolus, or i.m. injection.

For adults, 5–50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections, and particularly urinary tract infections, a dose of 250 mg t.i.d. or q.i.d. is recommended. For moderate infections against highly susceptible gram positive and gram negative organisms, a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5–25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Certain of these carbapenems are susceptible to attack by a renal enzyme known as dehydropeptidase (DHP). This attack or degradation may reduce the efficacy of the carbapenem antibacterial agent. Inhibitors of DHP and their use with carbapenem antibacterial agents are disclosed in the prior art [see European Patent Applications No. 79102616.4 filed July 24, 1979 (Patent No. 0 010 573); 79102615.6, filed July 24, 1979

(Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1.define the procedure for determining DHP susceptibility of the present carbapenems and 2.disclose suitable inhibitors, combination compositions and methods of treatment, they are incorporated herein by reference. A preferred weight ratio of Formula I compound:DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

These combination compositions and their use are further embodiments of the present invention.

DETAILED DESCRIPTION OF THE INVENTION

The compounds of Formula I may be prepared by any convenient process.

One such process is illustrated of the following reaction equations:

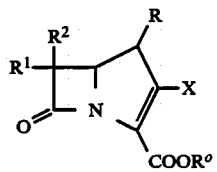

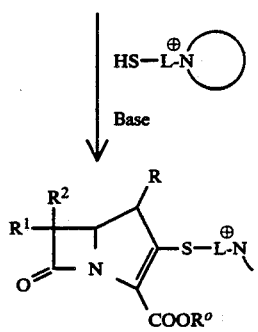

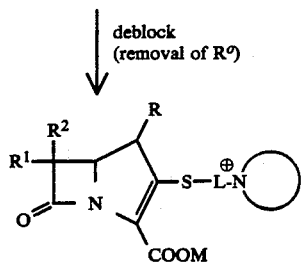

where R° is other than (—) or H and is a readily removable carboxyl covering group e.g. p-NO$_2$benzyl or allyl. x is a leaving group such as OP(O)(O0)$_2$,

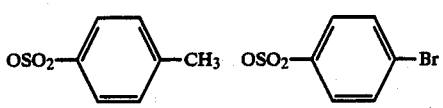

OSO$_2$CF$_3$, S(O)R" where R" is CH$_3$, CH$_2$CH$_3$, CH$_2$CH$_2$NHC(O)CH$_3$ and the like.

The process conditions are generally those available in the prior art. Thus, the side chain addition reaction is carried out in a solvent such as acetonitrile, dimethylformamide, dimethylacetamide, tetrahydrofuran, or N-ethylpyrrolidinone with or without added water to solubilize the reactants in the presence of a base such as N,N-diisopropylethylamine, triethylamine, or 4-dimethylaminopryidine at a temperature of from −40° C. to 25° C. for a period of 5 minutes to 10 hours. The deblocking reaction wherein R° is p-nitrobenzyl is usually conducted in an aqueous system containing cosolvents such as tetrahydrofuran, ethanol, n-butanol, 2-amyl alcohol, of ethyl acetate and a pH 6.8–7.0 aqueous buffer. Suitable buffers include phosphate buffers and buffers derived from non-nucleophilic amines such as N-methylmorpholine or morpholinopropane sulfonic acid. The reaction is conducted at 0° C. to 40° C. for 0.5 to 5 hours under 1–100 atmospheres of hydrogen in the presence of a catalyst such as 10% palladium on carbon or 20% palladium hydroxide on carbon. The final products are purified by ion exchange chromatography and/or reverse phase chromatography, exclusion chromatography, or by a combination of these techniques. When a pharmaceutically acceptable ester of the final product is desired, the deblocking step is omitted and the appropriate R° group is incorporated into the starting material.

A second process for preparing Formula I compounds is illustrated by the following reaction equations:

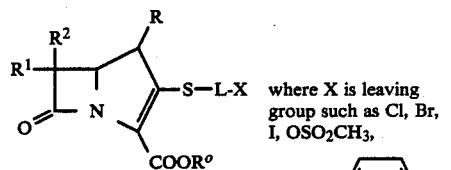 where X is leaving group such as Cl, Br, I, OSO$_2$CH$_3$,

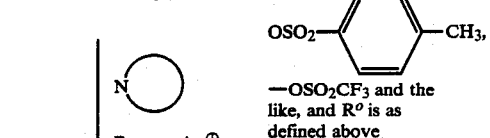 —OSO$_2$CF$_3$ and the like, and R° is as defined above

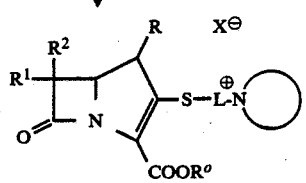

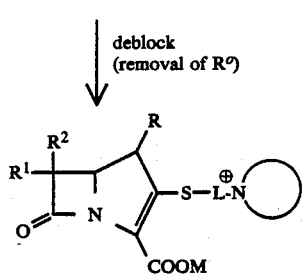

Again, the process conditions are those available in the prior art.

A third process for preparing Formula I compounds is illustrated by the following equations:

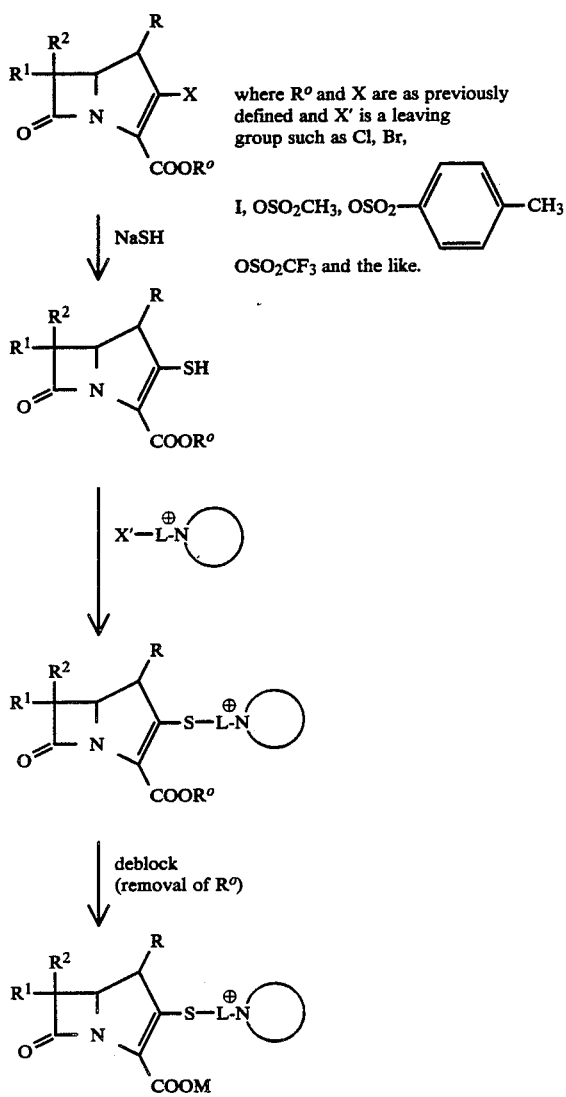

where $R^o$ and X are as previously defined and X' is a leaving group such as Cl, Br, I, $OSO_2CH_3$, $OSO_2\text{—}\langle\text{—}\rangle\text{—}CH_3$ $OSO_2CF_3$ and the like.

Again, the process conditions are those available in the prior art.

Following are examples illustrating the preparation of compounds of Formula I. Examples 1–10, 65 and 66 include complete experimental detail along with accompanying physical data for intermediates and final products. The chemistry leading to the final products of Examples 11–64, 67 and 68 utilizes procedures similar to that of Examples 1–10, and is presented in summary form along with physical data for the final products. The compounds of Example 69 are prepared by analogy to those of Examples 1–68.

Temperatures are give in °C. unless otherwise specified. The UV data for the carbapenem products usually includes the results of extinguishing the bicyclic β-lactam-thieno ether chromophore with hydroxyamine ($NH_2OH$). This result is expressed as a percentage loss of the unextinguished λ max or as the λ max and molar absorptivity of the extinguished chromophore as determined by subtraiting the $NH_2OH$ treated curve from the extinguished curve. The final products are usually purified by chromatography on a column of Dowex 50W (sodium form) resin followed by chromatography on reverse phase, silica gel plates (RPS). Alternative purification procedures include Chromatography on the neutral polystyrene resins XAD-2 or SP207 (brominated polystryene), or by RPS chromatography only. The yields of crude and chromatographed products are based on UV analysis of appropriate solutions using, in most cases, an assumed $NH_2OH$ extinguished molar absorptivity of 9500 for 100% pure products.

The following abbreviations are used in the examples are accompanying schemes:
Ac=acetyl
iAm=isoamyl
Bu=butyl
DMAC=N,N-dimethylacetamide
DMF=N,N-dimethylformamide
Et=ethyl
EtOAc=ethyl acetate
LDA=lithium diisopropylamide
Me=methyl
MeCN=acetonitrile
Ms=methanesulfonyl
NBS=N-bromosuccinimide
Ph or φ phenyl
PNB=p-nitrobenzyl
iPr=isopropyl
THF=tetrahydrofuran
Ts=p-toluenesulfonyl

EXAMPLE 1

Sodium (5R,6S)-2-[2-(3-carboxylato-1-pyridiniun)ethylthio]-6-[1(R)-hydroxyethyl]carbapen-2-em-3-carboxylate

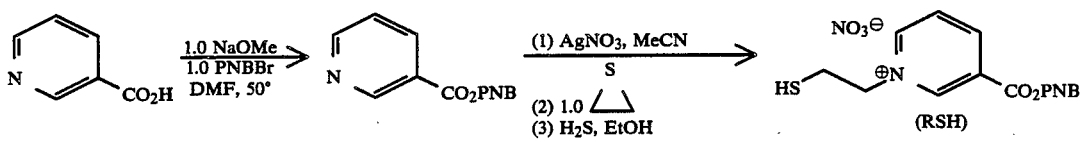

-continued

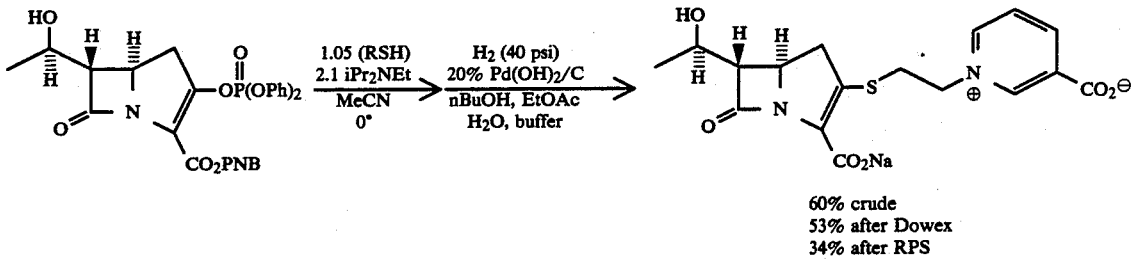

60% crude
53% after Dowex
34% after RPS

Detailed procedures and physical data follow.

STEP 1 p-Nitrobenzyl nicotinate

A Suspension of nicotinic acid (5.00 g, 40.6 mmol) in N,N-dimethylformaide (40 ml) was treated with sodium methoxide (2.19 g, 40.6 mmol). The resulting solution was treated with p-nitrobenzylbromide (8.77 g, 40.6 mmol) and heated at 50°, After heating 16 hrs the reaction was allowed to cool to ambient temperature and diluted with ethyl acetate (100 ml) and saturated aqueous sodium bicarbonate solution and filtered. The organic fraction was separated and washed with water, brine, dried over anhydrous magnesium sulfate, filtered and evaporated under vacuum to a solid.

The crude product was chromatographed on a column of silica gel (E. Merck #7734) eluted with hexane-ethyl acetate (2:1). The product crystallized from the eluting solvent upon standing and was recovered to give a white crystalline product, 2.85 g(29% yield).

NMR(CDCl$_3$)δ 5.56(s, CH$_2$), 7.63(dd, pyridyl H5), 7.80(d, aryl 2H), 8.28(d, aryl 2H), 8.39(td, pyridyl H4), 8.87(dd, pyridyl H6), 9.20(d, pyridyl H2).

STEP 2

1-(2-Mercaptoethyl)-3-(p-nitrobenzyloxycarbonyl) pyridinium nitrate

A solution of silver nitrate (1.39 g, 8.19 mmol) in acetonitrile (10 ml) was added to a solution of p-nitrobenzyl nicotinate (2.00 g, 8.19 mmol) in acetonitrile (50 ml). A tan precipitate formed. The mixture was stirred at room temperature and treated with ethylene sulfide (0.49 ml, 8.19 mmol). After 1.5 hours, the mixture was filtered to remove the precipitate which dried under vacuum to an off-white solid. This material was suspended in ethanol (75 ml), treated with hydrogen sulfide over 5 minutes, and stirred an additional 5 minutes at room temperature. The mixture was centrifuged and filtered to remove the silver sulfide. The filtrate, on standing overnight at room temperature, deposited the title compound (0.30 g) as fine white needles.

NMR (DMSO-d$_6$)δ 2.72 (t, J=7 Hz, SH), 3.15 (q, J=7 Hz, SCH$_2$), 4.90 (t, J=7 Hz, NCH$_2$), 5.66 (s, CH$_2$Ar), 7.87 (d, J=8 Hz, 2 ArH), 8.33 (d, J=8 Hz, 2 ArH), 8.38 (m, pyridyl H5), 9.14 (d, J=8 Hz, pyridyl H4), 9.31 (d, J=6 Hz, pyridyl H6), 9.70 (s, pyridyl H2).

STEP 3

Sodium (5R,6S)-2-[2-(3-carboxylato-1-pyridinium) ethylthio]-6-[1(R)-hydroxyethyl]carbapen-'-em-3-carboxylate A solution of p-nitrobenzyl (5R,6S)-2-(diphenylphosphono)oxy-6-[1(R)-hydroxyethyl]carbapen-2-em-3-carboxylate (175 mg, 0.30 mmol) and 1-(2-mercaptoethyl)-3-(p-nitrobenzyloxycarbonyl)-pyridinium nitrate (120 mg, 0.32 mmol) in anhydrous acetonitrile (3.0 ml) was cooled in an ice-bath under a nitrogen atmosphere and treated with N,N-diisopropylethylamine (0.11 ml, 0.63 mmol). The resulting solution was left an ice-bath temperature overnight, then diluted with diethylether (30 ml) and passed through a celite pad. The ether insoluble oil and the residue left on the celite pad were dissolved in a mixture of n-butanol (19 ml), ethylacetate (9 ml), water (19 ml), and 0.5M pH 6.8 N-methyl morpholine-hydrochloric acid buffer (9 ml), treated with 20% palladium hydroxide on carbon (105 mg), and hydrogenated on a Parr shaker at 40 psi for 1 hour. The mixture was centrifuged to remove the catalyst and the supernatant was washed with methylene chloride (2×25 ml). The aqueous phase was concentrated under vacuum and added to a column of Dowex 50W-X4 resin (sodium form, 200–400 mesh, 1.5×33 cm) which was eluted with deionized water in a cold room. The product containing fractions were located by UV, combined, and concentrated under vacuum to ca. 2.5 ml. The solution was applied to four Analtech 0.5 mm×20×20 cm RPS-F plates which were developed with water in a cold room. The major UV visible band was removed and eluted with 4:1 acetonitrile-water. The extracts were washed with hexane, concentrated under vacuum, and lyophilized to provide the title compound (60.5 mg) as an amorphous, yellow solid.

IR (Nujol) 3350(br), 1755, 1645, 1610, 1580, 1250, 1135, 1072 cm$^{-1}$.

UV (H$_2$O)λ max 270(ε 6040), 296(ε 6970) nm. UV (H$_2$O+NH$_2$OH)λ max ext. 296(ε ext. 6250) nm.

NMR (D$_2$O)δ 1.27(d, CH$_3$CH), 2.94 and 3.11(two dd, CH$_2$), 3.33(dd, H6), 3.40 and 3.58(two tq, SCH$_2$), 4.01(dt, H5), 4.20(p, CH$_3$CH), 4.8–4.9(m, CH$_2$N), 8.10(t, pyridyl H5), 8.9–8.95(m, pyridyl H4,H6), 9.26(s, pyridyl H2).

EXAMPLE 2

Sodium (1R,5S,6S)-2-[2-(4-carboxylato-1-pyridinum)ethylthio]-6-[1-(R)-hydroxyethyl]-1-methyl-carbapen-2-em-3-carboxylate

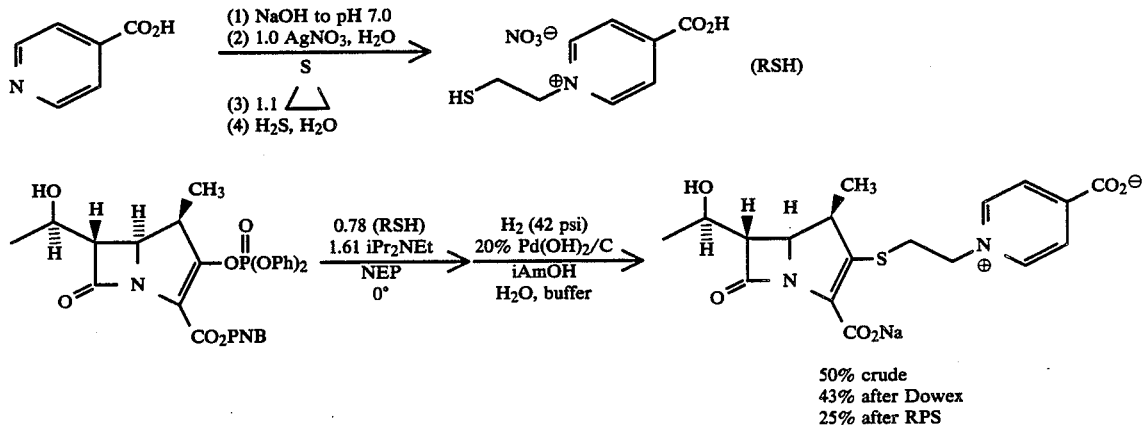

50% crude
43% after Dowex
25% after RPS

Detailed procedures and physical data follow:

STEP 1

1-(2-mercaptoethyl)-4-carboxy-pyridinium nitrate

A suspension of isonicotinic acid (2.00g, 16.2 mmol) in water (20 ml) was adjusted to pH 6 with aqueous sodium hydroxide (2.5N). The resulting solution was treated with a solution of silver nitrate (2.76 g, 16.2 mmol) in water (5ml) to give a white suspension. Additional water (20 ml) was added to facilitate stirring and the suspension was treated with ethylene sulfide (1.06 ml, 17.8 mmol). After 1 hr the yellow suspension was filtered, the cake water washed, and resuspended in water (25 ml). The suspension was bubbled with hydrogen sulfide (5 min), stirred (5 min), and filtered.

The filtrate was evaporated under vacuum to a yellow solid (1.57g, 38%).

NMR($D_2O$)δ3.17(t, J=6.4Hz, $SCH_2$), 4.83(t, J=6.4 Hz, $NCH_2$), 8.38(d, J=6.5 Hz, pyridyl H3, H5), 8.98(d, J=6.5 Hz, pyridyl H2, H6).

STEP 2

Sodium (1R,5S,6S)-2-[2-(4-carboxylato-1-pyridinium)-ethylthio]-6-[1(R)-hydroxyethyl]-1-methylcarbapen-2-em-3-carboxylate A suspension of 1-(2-mercaptoethyl)-4-carboxypyridinium nitrate (26mg, 0.10 mmol) and vinyl phosphate (75mg, 0.13 mmol) in N-ethylpyrrolidinone (0.50 ml) was cooled in an ice bath and treated with N,N-diisopropylethylamine (0.037 ml, 0.21 mmol). After 24 min the reaction solution was mixed with water (1.3 ml), pH 7.0 0.5M N-methylmorpholine-HCl buffer (1:0 ml), isoamyl alcohol (1 8 ml), and 20% palladium hydroxide on carbon (34 mg) and hydrogenated on a Parr shaker.

After 1 hr the mixture was removed from the shaker, filtered, and the organic phase discarded. The aqueous phase was washed with dichloromethane, concentrated and chromatographed on a Dowex50-X4 ($Na^+$ cycle) column eluted with water in the cold room (4°). The product solution was isolated, concentrated, and chromatographed on three 1000 micron thick (20×20 cm) RPS-F plates (Analtech) using 1.5% ethanol-water as developing solvent. The desired product bands were isolated, extracted with acetonitrile-water (100 ml, 5:1), and this solution washed with hexane. The solution was concentrated under vacuum and lyophilized to afford the product as an off-white fluff (21.2 mg).

IR (Nujol) 3350(br), 1755, 1620, 1570, 1140 $cm^{-1}$.

UV ($H_2O$)λ max 293(ε 7370)nm. UV ($H_2O$+N-$H_2OH$)λ max ext. 297(ε ext. 6280) nm.

NMR ($D_2O$)ε 1.15(d, 1-$CH_3$), 1.28(d, $CH_3CHOH$). 3.2–3.3(m, H1), 3.29 and 3.57 (two td, $SCH_2$), 3.42(dd. H6). 3.97(dd. H5). 4.22(p. $CH_3CHOH$). 4.9–5.1(m, $CH_2N$), 8.30(d, pyridyl H3, H5), 8.91(d, pyridyl H2,H6).

EXAMPLE 3

Sodium (5R,6S)-6-[1(R)-hydroxyethyl]-2-[2-(4-sulfonatomethyl)-lyridinium)ethylthio]carbapen-2-em-3-carboxylate

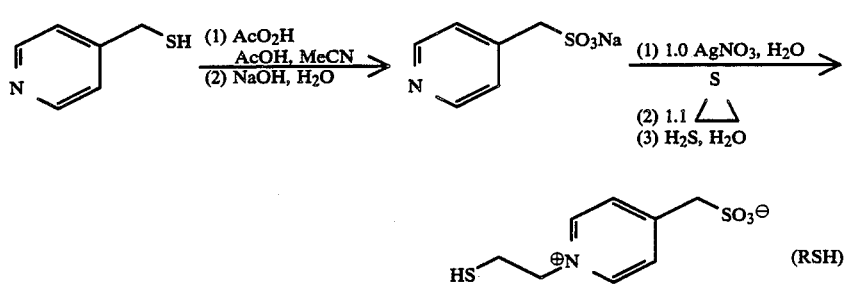

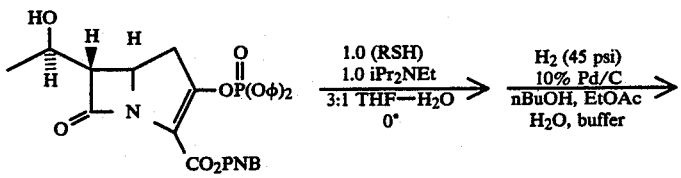

-continued

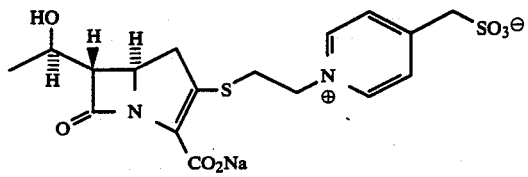

37% crude
37% after Dowex
32% after RPS

Detailed procedures and physical data follow:

STEP 1
Sodium 4-pyridylmethylsulfonate

A solution of 4-mercaptomethylpyridine (2.20 g, 17.6 mmol) in acetonitrile (8.0 ml) was added to a stirred solution of 40% peracetic acid-acetic acid (25 ml) at ice bath temperature. After addition the solution was removed from the ice bath and stirred at room temperature overnight. The solution was concentrated under vacuum to a white solid which was dissolved in water (1.5 ml) and adjusted to pH 9 with 2.5N aqueous sodium hydroxide. The resulting white suspension was filtered and the filtrate evaporated under vacuum to afford the title compound as a white solid (2.32 g).

NMR ($D_2O$) δ 4.24 (s, $CH_2$), 7.50 (d, J=5.4 Hz, ArH), 8.53 (d, J=5.4 Hz, ArH).

STEP 2
1-(2-Mercaptoethyl)-4-sulfomethylpyridinium hydroxide, inner salt A solution of silver nitrate (1.31 g, 7.68 mmol) in water (4 ml) was added to a stirred solution of sodium 4-pyridylmethylsulfonate (1.50 g, 7.68 mmol) in water (15 ml). The resulting hazy solution was treated with ethylene sulfide (0.51 ml, 8.58 mmol) added dropwise over 2 minutes. The resulting gummy mixture was let stand at room temperature 30 minutes and the supernatant decanted. The residue was mixed with water (10 ml) and vigorously bubbled with hydrogen sulfide for 10 minutes. The mixture was vigorously stirred an additional 1 hour and the silver sulfide precipitate removed by centrifugation. The supernatant was concentrated under vacuum to ca. 5 ml and charged onto a column of Dowex 50W-X4 (hydrogen form, 200–400 mesh, 1.5×33 cm). The column was eluted with water at 6.0 ml fractions/2.0 minutes. Fractions 19 to 27 were combined and evaporated under vacuum to an off-white solid. The solid was mixed with a few mls of methanol and filtered to afford the title compound as an off-white solid (303 mg).

NMR ($D_2O$) δ 3.16 (t, J=6.4 Hz, $SCH_2$), 4.52 (s, $CH_2SO_3$), 4.79 (t, J=6.4 Hz, $NCH_2$), 8.12 (d, J=6.2 Hz, pyridyl H3, H5), 8.86 (d, J=6.2 Hz, pyridyl H2, H6).

Anal. Calc'd for $C_8H_{11}NO_3S_2$: C, 41.18; H, 4.75; N, 6.00; S, 27.48. Found: C, 41.32; H, 4.77; N, 6.07; S, 27.17.

STEP 3
Sodium (5R,6S)-6-[1(R)-hydroxyethyl]-2-[2-(4-sulfonatomethyl-1-pyridinium)ethylthio]carbapen-2-em-3-carboxylate A solution of p-nitrogenzyl (5R,6S)-2-(diphenylphosphono)oxy-6[1(R)-hydroxyethyl]-carbapen-2-em-3-carboxylate (300 mg, 0.517 mmol) and 1-(2-mercaptoethyl)-4-sulfomethylpyridinium hydroxide inner salt (121 mg, 0.517 mmol) in tetrahydrofuran (2.0 ml) and water (0.65 ml) was treated at ice bath temperature with N,N-diisopropylethylamine (0.090 ml, 0.517 mmol). After stirring 10 min, the reaction solution was diluted with n-butanol (10.0 ml), ethyl acetate (5.0 ml), water (10.0 ml), and 0.5M pH 6.8 N-methylmorpholine - hydrochloric acid buffer (5.0 ml), mixed with 10% palladium on carbon (125 mg), and hydrogenated on Parr shaker at 45 psi for 75 min The catalyst was removed by filtration through a prewashed celite pad, and the filtrate washed with methylene chloride. The aqueous phase was concentrated under vacuum to ca. 7.5 ml and charged onto a column of Dowex 50W-X4 (sodium form, 200–400 mesh, 1.5×33 cm). The column was eluted with water in the cold room (4°) at 6.0 ml fractions/2.0 min. Fractions 4 to 8 were combined and concentrated under vacuum to ca. 8 ml and lyophilized to powder. This material was chromatographed on five 1.0 mm×20×20 cm Analtech RPS-F plates using water as a developing solvent in a cold room (4°). The major uv visible band on each plate at Rf 0.3 0.5 was removed and eluted with 4:1 acetonitrile-water. The eluant was washed with hexane, concentrated under vacuum to ca. 20 ml, filtered through an Acrodisc (Gelman, 0.2 micron CR) and lyophilized to afford the title compound (100.3 mg) as an amorphous white powder.

IR (Nujol) 3400 (br), 1740, 1638, 1582, 1520, 1231, 1190, 1036 $cm^{-1}$.

UV ($H_2O$) λ max 219(ε 11,400), 260(ε 6,320), 296(ε 7,250)nm.

NMR ($D_2O$) δ 1.20(d $CH_3CH$), 2.94 and 3.08(two dd, $CH_2$), 3.3–3.53(m, $SCH_2$), 3.35(dd, H6), 4.07(dt, H5), 4.20(p, $CH_3CH$), 4.52(s, $CH_2SO_3$), 4.6–4.8(m, $CH_2N$), 8.11(d, pyridyl H3,H5), 8.85(d, pyridyl H2,H6).

EXAMPLE 4

Sodium (1R,5S,6S)-6-[1(R)-hydroxyethyl]-2-[2-(4-sulfonatomethyl-1-pyridinium)ethylthio)-1-methylcarbapen-2-em-3-carboxylate

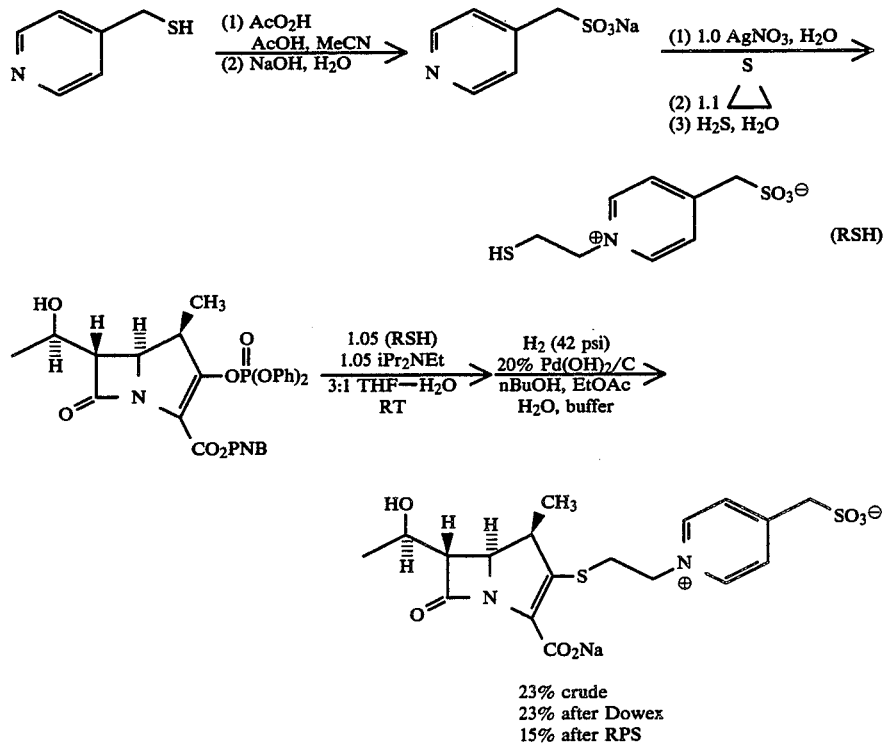

23% crude
23% after Dowex
15% after RPS

Detailed procedures and physical data follow:

STEP 1

Sodium (1R,5S,6S)-6-[(1R)-hydroxyethyl]-2-[2-(4-sulfonatomethyl)-1-pyridinium)ethylthio]-1-methylcarbapen-2-em-3-carboxylate A solution of p-nitrobenzyl (1R,5R,6S)-2-(diphenylphosphono)oxy-6-[(1R)-hydroxyethyl]-1-methylcarbapen-2-em-3-carboxylate (200 mg, 0.336 mmol) and 1-(2-mercaptoethyl)-4 sulfomethylpyridinium hydroxide inner salt (82 mg, 0.353mmol) in tetrahydrofuran (1.5 ml) and water (0.5 ml) was treated at room temperature with N,N-diisopropylethylamine (0.062 ml, 0.353mmol). After stirring 11 min, the reaction solution was diluted with n-butanol (6.7 ml), ethyl acetate (3.4 ml), water (6.7 ml), and 0.5M pH 6.8 N-methylmorpholine-hydrochloric acid buffer (3.4 ml), mixed with 20% palladium hydroxide on carbon (75 mg). and hydrogenated on a Parr shaker at 42 psi for 75 min. The catalyst was removed by filtration through a celite pad, and the filtrate washed with methylene chloride. The aqueous phase was concentrated under vaccuum to ca. 10 ml and charged onto a column of Dowex 50W-X4(sodium form, 200–400 mesh, 1.5×33 cm). The column was eluted with water in the cold room (4°) at 4.0 ml fractions/2.0 min. Fractions 4 to 10 were combined and concentrated under vacuum to ca. 8 ml and lyophilized to powder. This material was chromatographed on four 1.0 mm ×20×20 cm Analtech RPS-F plates using 2% ethanol water as a developing solvent in a cold room (4°). The uv visible band on each plate at Rf 0.4–0.5 was removed and eluted with 4:1 acetonitrile-water. The eluant was washed with hexane, concentrated under vacuum to ca. 4 ml, filtered through an Acrodisc (Gelman, 0.45 micron CR) and lyophilized to afford the title compound (35.3 mg) as an amorphous white powder.

IR (Nujol) 3400(br), 1740, 1640, 1590, 1235, 1185, 1040 cm$^{-1}$.

UV (H$_2$O) λ max 229($\epsilon$ 11600), 260($\epsilon$ 6020), 298($\epsilon$ 6940)nm. UV (H$_2$O+NH$_2$OH) λ max ext. 297nm ($\epsilon$ ext. 6130)nm.

NMR (D$_2$O) δ 1.14(d, 1-CH$_3$), 1.28(d, CH$_3$CHOH), 3.22(dq, H1), 3.29 and 3.56 (two td, SCH$\overline{_2}$), 3.41(dd, H6), 3.99(dd, H5), 4.29(p, CH$_3$CHOH), 4.53(s, CH$_2$SO$_3$), 4.7–4.9(m, CH$_2$N), 8.11(d, pyridyl H3,H5), 8.83(d, pyridyl H2,H6).

EXAMPLE 5

Sodium (5R,6S)-2-[2-(3-chloro-4-sulfonatomethyl-1-pyridinium-)ethylthio]-6-[1(R)-hydroxyethyl]carbapen-2-em-3-carboxylate

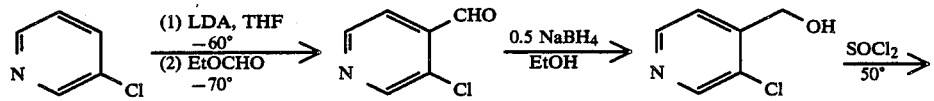

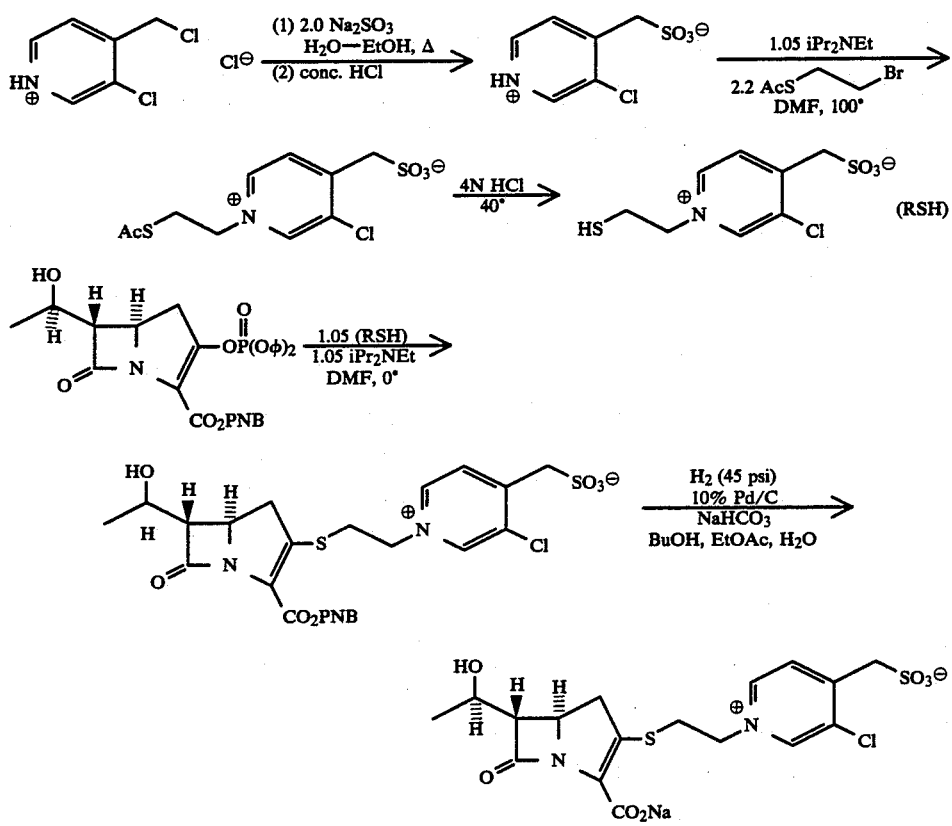

-continued

Detailed procedures and physical data follow:

STEP 1

3-Chloro-4-pyridinecarboxaldehyde

An ice cold solution of N,N diisopropylamine (66.0 ml, 0.471 mol) in freshly distilled tetrahydrofuran (1190 ml) in a dry three neck flask fitted with a dropping funnel, thermometer, and septum was treated dropwise with n-butyl lithium in hexane (2.6M, 185 ml, 0 462 mol). The solution of lithium diisopropylamide was aged at 0° for 30 min, then cooled in a chloroform-dry ice bath to −60° and treated with 3-chloropyridine (41.9 ml, 0.440 mol) added over 5 min. A brown mixture slowly developed.

After 1 hr from the completion of addition the brown mixture was cooled in an acetone-dry ice bath to an internal temperature of −70° and treated with ethyl formate (40.0 ml, 0.495 mol) added neat over 1 min. The internal temperature rose to −62°. The brown mixture yielded to a brown solution which was stirred 30 min at acetone-dry ice bath temperature (internal temperature after 30 min −70°) then treated with aqueous 3N hydrochloric acid (154 ml, 0.462 mol) and allowed to warm to ambient temperature.

The reaction was concentrated under vacuum to a viscous oil and mixed with ethyl acetate (250 ml). The organic phase was recovered and the aqueous phase extracted with ethyl acetate (200 ml). The combined organic extracts were washed with brine, dried over anhydrous magnesium sulfate, filtered, and concentrated under vacuum to a brown semi-solid (63.23 g).

The entire crude product was absorbed onto silica gel (60g, E. Merck #7734) and applied to a silica gel column (125g, column 5.5 cm ×8.7 cm diam.) packed in 3:1 hexane-ethyl acetate. The column was eluted with the same solvent system at maximum flow rate. The product was collected as a light yellow solid (43.80 g, 70%).

NMR(CDCl$_3$) δ 7.71(d, J=4.9 Hz, Ar5H), 8.70(d, J=4.9 Hz, Ar6H), 8.80(s, Ar2H), 10.50(s, CHO).

mp 58.0°–58.5°

Microanalytical: Calc'd C, 50.91; H, 2.85; N, 9.90; Found C, 50.63; H, 2.78; N, 9.66.

STEP 2

3-Chloro-4-hydroxymethylpyridine

A suspension of 3-chloro-4-pyridinecarboxaldehyde (43.80g, 0.310mol) in ethanol (200 ml) was cooled in an ice bath and treated with powdered sodium borohydride (5.85 g, 0.155 mol) added in portions over approximately 2 min. The resulting solution was removed from the ice bath and stirred at ambient temperature. After 1 hr the solution was recooled in an ice bath and treated with acetone (22 ml) to decompose excess borohydride. The solution was again removed from the ice bath and stirred at ambient temperature. After 30 min the reaction solution was evaporated under vacuum to a viscous oil.

The oil was partitioned between ethyl acetate (250 ml) and a saturated aqueous solution of sodium bicarbonate (50 ml). The organic phase was recovered and the aqueous phase extracted with additional ethyl acetate (150 ml). The combined organic phases were washed with brine, dried over anhydrous magnesium sulfate, filtered, and evaporated under vacuum to a white solid (54.90g). The crude product was dissolved in hot toluene (500 ml) and crystallized upon cooling to provide the desired product (33.90 g, 76%).

NMR(CDCl$_3$) δ 4.67(s, CH$_2$OH), 7.37(d, J=5.3Hz, Ar5H), 8.35(d, J=5.3Hz, Ar6H), 8.36(s, Ar2H).

mp 114°-115°

Microanalytical: Calc'd C, 50.19; H, 4.21; N, 9.76; Found C, 50.53; H, 4.22; N, 9.71.

STEP 3

3-Chloro-4-chloromethylpyridine hydrochloride

Solid 3-chloro-4-hydoxymethylpyridine (33.8 g, 0.235 mol) was added cautiously over 8 min to stirred thionyl chloride (72 ml, 0.706 mol) cooled in an ice bath and under a stream of N$_2$. After addition the yellow solution was heated in an oil bath at 50° and protected under a tube of Drierite. After 30 min the solution was removed from the oil bath, allowed to cool to ambient temperature, and poured into a flask of stirred anhydrous ether (1,000 ml).

The precipitate was recovered by filtration, ether washed, and the solid vacuum dried to afford the product as an off-white solid (45.77q, 98%).

NMR(DMSO-d$_6$) δ 4.88(s, CH$_2$Cl), 7.73(d, J=4.9 Hz, Ar5H), 8.62(d, J=4.9 Hz, Ar6H), 8.76 (s, Ar2H).

STEP 4

3-Chloro-4-sulfomethylpyridine

A suspension of sodium sulfite (75.90 g, 0.602 mol) in a solution of water (240 ml) and ethanol (60 ml) was treated at ambient temperature with solid 3-chloro-3-chloromethylpyridine hydrochloride (59.77g, 0.301 mol). The resulting mixture was heated in an oil bath to reflux.

After 2hr the resulting light yellow solution was removed from the bath and allowed to cool to ambient temperature and evaporated under vacuum to a semi-solid. The crude sodium salt was mixed with concentrated hydrochloric acid (100 ml) and filtered. The cake was washed with an additional amount (100 ml) of concentrated acid. The filtrate deposited additional salt and was refiltered.

The acidic filtrate was concentrated under vacuum to an orange colored semi-solid. The solid was again suspended in concentrated hydrochloric acid (50 ml) and refiltered and the salt cake washed with concentrated acid. The filtrate was concentrated under vacuum to a semi-solid and mixed with glacial acetic acid (600 ml). The mixture was heated to reflux and filtered hot. The recovered solid was washed with a small portion of acetic acid and vacuum dried to produce a lightly pink colored solid (41.10 g, 66%).

NMR(D$_2$O) δ 4.64(s, CH$_2$SO$_3$), 8.13(d, J=5.5Hz, Ar5H), 8.71(d, J=5.5Hz, Ar6H), 8.96(s, Ar2H).

STEP 5

1-(2-Acetylthioethyl)-3-chloro-4-sulfomethyl-pyridinium hydroxide, inner salt

A suspension of 3-chloro-4-sulfomethylpyridine (19.0 g, 0.092 mol) in DMF (100 ml) was treated with N,N diisopropylethylamine (16.8 ml, 0.096 mol) and 2-bromoethyl thiolacetate (16.0 ml, 0.137 mol). The resulting pale yellow solution was heated in an oil bath at 100° for 2 hrs, then treated with additional alkylating agent (7.5 ml, 0.064mol. 2.2 equiv. total) and heated overnight at 100°.

After 19 hrs heating, a dark suspension had formed and reverse phase TLC (Analtech RPS-F, H$_2$O, UV) showed no starting material. The mixture was cooled in an ice bath for 30 mins and in a freezer for 30 mins, then filtered. The filter cake was washed with cold ethanol (100 ml) and dried under a stream of N$_2$ to afford the crude product (22g) as a light yellow solid.

This material in DI H$_2$O (100 ml) was mixed with activated charcoal, heated to 35° on a steam bath, and filtered through a pad of Solka-Floc using additional rinse H$_2$O (5 ml). The aqueous filtrate was concentrated under vacuum to remove 60 ml of H$_2$O, then diluted with ethanol (250 ml) and seeded. The mixture was kept at ambient temperature for 10 mins, followed by cooling in an ice bath for 30 mins and in a freezer for 30 mins. The product was collected, washed with ethanol (100 ml), and dried under a N$_2$ stream to provide the title compound as pale yellow crystals (21.5 g).

NMR(D$_2$O) δ 2.41(s, SCOCH$_3$), 3.63(t, J=6.0 Hz, SCH$_2$), 4.91(t, J=6.0 Hz, CH$_2$N), 4.75(s, CH$_2$SO$_3$), 8.28(d, J=6.0 Hz, Ar5H), 8.94(d, J=6.0 Hz, Ar6H), 9.32(s, Ar2H).

STEP 6

1-(2-Mercaptoethyl)-3-chloro-4-sulfomethylpyridinium hydroxide, inner salt

A solution of the N-acetylthioethyl -pyridinium salt (18.5g, 0.06 mol) in 4N HCl (100 ml) was heated in a 40°oil bath and under a N$_2$ atm for 18 hrs. The solution was evaporated under vacuum and the residue twice stripped with ethanol to give an off-white solid. This material was suspended in ethanol, filtered, and dried under a N$_2$ stream to provide the product (14.0 g, 87.5%) as a white solid.

NMR(D$_2$O) δ 3.20(t, J=6.0 Hz, SCH$_2$), 4.71(s, CH$_2$SO$_3$), 4.83(t, J=6.0 Hz, CH$_2$N), 8.25(d, J=6.0 Hz, Ar5H), 8.88(d, J=6.0 Hz, Ar6H), 9.23(s, Ar2H).

Microanalytical: Calc'd C, 35.89; H, 3.76; N, 5.23; S, 23.95; Found C, 35.76; H, 3.82; N, 5.18; S, 24.28.

STEP 7 p-Nitrobenzyl (5R,6S)-2-[2-(3-chloro-4-sulfonatomethyl-1-pyridinium-)ethylthio]-6-[1-(R)-hydroxyethyl]carbapen-2-em-3-carboxylate A suspension of vinyl phosphate (2.00 g, 3.45 mmol) and finely powdered mercaptan (968 mg, 3.62 mmol) in anhydrous DMF (6.9 ml) was cooled in an ice bath under a N$_2$ atmosphere. The suspension was treated with iPr$_2$NEt (0.630 ml, 3.62 mmol) added dropwise over 40 min. After base addition a thick, light tan colored suspension resulted which was mixed with EtOH (75 ml) and filtered. The filter cake was washed with EtOH (2×50 ml) followed by Et$_2$O (50 ml) and dried under a N$_2$ stream. The final product was vacuum dried to afford an off-white crystalline solid (1.83 g, 88.8%).

NMR(DMSO-d$_6$) δ 1.16(d, CH$_3$CHOH), 3.2-3.6 (m, CH$_2$), 3.40(dd, H6), 3.57(m, SCH$_2$), 3.98(m, CH$_3$CHOH), 4.19(m, H5), 4.22(s, CH$_2$SO$_3$), 4.80(m, CH$_2$N), 5.13(d, OH), 5.40(ABq, CH$_2$Ar), 7.70 and 8.24 (two d's, ArH), 8.20(d, pyr H5), 8.95(d, pyr H6), 9.34(s, pyr H2).

STEP 8

Sodium (5R,6S)-2-[2-(3-chloro-4-sulfonatomethyl-1-pyridinium-)ethylthio]-6-[1(R)-hydroxyethyl]carbapen-2-em-3-carboxylate The crystalline ester (1.25 g, 2.09 mmol) was added to a mixture of n butanol (5 ml), ethyl aceta (25 ml), and water (100 ml) to give a freely flowing suspension in the upper phase. Solid NaHCO$_3$ (175 mg, 2.09 mmol) and 10% Pd/C (500 mg) were added and the mixture was hydrogenated in a 450 ml Paar flask at 45 psi for 2 hrs ( the ester dissolved within the first hour).

The reaction mixtures from two identical runs were combined and filtered through a pad of solka-floc. The aqueous portion of the filtrate was separated, washed with ethyl acetate (200 ml), and concentrated under vacuum to 42 ml. The concentrate was added to an ice water jacketed, prewashed column of SP-207 resin (2.5 cm ×25.5 cm, 125 cc) which was eluted initially with DI water and then with 4% methanol in water at a rate of 5 ml/min. 25 Ml fractions were collected. The progress of the chromatography was monitored by UV and NMR spectroscopy. The results are tabulated below.

| Fractions | Eluant | Volume | Weight | ε ext 300 nm |
|---|---|---|---|---|
| 1–5 | H$_2$O | 125 ml | — | — |
| 6 | H$_2$O | 25 ml | 0.056 g | 6216 |
| 7 | H$_2$O | 25 ml | 0.083 g | 6819 |
| 8 | H$_2$O | 25 ml | 0.105 g | 6653 |
| 9–27 | H$_2$O | 475 ml | 1.080 g | 6931 |
| 28–45 | 4% CH$_3$OH | 450 ml | 0.234 g | 6540 |
| 46–63 | 4% CH$_3$OH | 450 ml | 0.048 g | 6242 |

Fractions 9–27 were combined, concentrated under vacuum to 100 ml, and lyophilyzed to afford the product (1.080 g) as a yellow, amorphous solid. Other fractions were similarly processed to give the weights shown in the table. Fractions 9–27 gave the cleanest product as evidenced by UV and $^1$H NMR spectroscopy.

NMR (D$_2$O) δ 1.29 (d, CH$_3$CH), 3.00 and 3.13 (two dd, CH$_2$), 3.38 (dd, H6), 3.36 and 3.56 (two td, SCH$_2$), 4.12 (dt, H5), 4.22 (dq, CH$_3$CH), 4.69 (s, CH$_2$SO$_3$), 4.88 (m, CH$_2$N), 8.23 (d, pyr H5), 8.84 (d, pyr H6), and 9.18 (s, pyr H2).

IR (nujol) νmax 3400 (br), 1740, 1630, 1585, 1230, 1190, and 1035 cm$^{-1}$.

UV (H$_2$O) λ max 300 (sh, ε 8570), 285 (ε 10,330), 240 (ε 10,040) nm; UV (H$_2$O+NH$_2$OH) λ max 276 (ε 4,830) nm; λ max ext 297 (ε ext 7050) nm.

EXAMPLE 6

Sodium (5R,6S)-6-[1(R)hydroxyethyl]-2-[2-[4-(2-sulfonatoethyl)-1-pyridinium]-ethylthio-carbapen-2-em-3-carboxylate

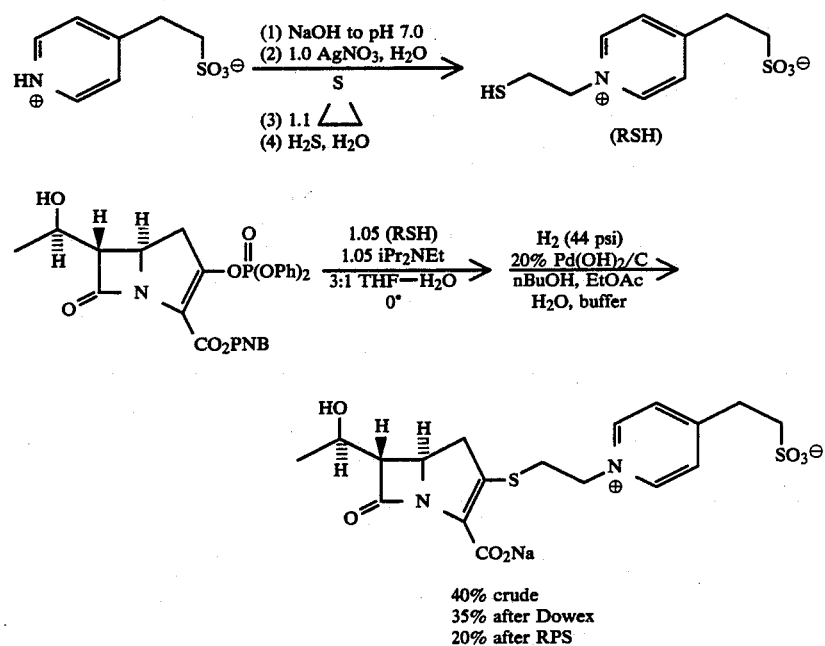

40% crude
35% after Dowex
20% after RPS

Detailed procedures and physical data follow:

STEP 1

1-(2-mercaptoethyl)-4-(2-sulfoethyl)pyridinium hydroxide inner salt

A solution of silver nitrate (1.84 g, 10.6 mmol) in water (5 ml) was added to a stirred aqueous solution (20 ml) of 4-pyridine ethane sulfonic acid (2.00 g, 10.6 mmol) which had been adjusted to pH 7 by the addition of aqueous 2.5N sodium hydroxide (3.0 ml). The solution was cooled in an ice-water bath and ethylene sulfide (0.71 ml, 11.8 mmol) added. The resulting mixture was let stand 45 minutes at ice-bath temperature and the upper clear phase decanted. The gummy solid was mixed with water (20 ml) and vigorously bubbled with hydrogen sulfide for 15 minutes. After stirring an additional 20 minutes, the mixture was filtered through a celite pad to remove silver sulfide and the filtrate was evaporated under vacuum to provide crude title compound as a white semi-solid (1.00 g).

STEP 2

Sodium (5R,6S)-6-[1(R)hydroxyethyl]2-[2-[4-(2-sulfonatoethyl(-1-pyridinium]-ethylthio]-carbapen-2-em-3-carboxylate A solution of p-nitrobenzyl (5R,6S)-2-(diphenylphosphono)oxy-6-[1R)-hydroxyethyl]-carbapen-2-em-3-carboxylate (200 mg, 0.344 mmol) and 1-(2-mercaptoethyl)-4-(2-sulfoethyl)pyridinium hydroxide inner salt 89 mg, 0.362 mmol) in tetrahydrofuran (1.0 ml) and water (0.3 ml) was treated at room temperature with N,N-diisopropylethylamine (0.063 ml, 0.362 mmol). After stirring 10 minutes, the reaction solution was diluted with n-butanol (6.8 ml), ethyl acetate (3.4 ml), water 6.8 ml), and 0.5M pH 6.8 N-methyl-morpholine-hydrochloric acid buffer (3.4 ml), mixed with 20% palladium hydroxide on carbon (80 mg), and hydrogenated on a Parr shaker at 44 psi for 75 minutes. The catalyst was removed by filtration through an Acrodisc (Gelman, 0.45 micron CR), and the filtrate washed with methylene chloride. The aqueous phase was concentrated under vacuum to ca. 8.5 ml and charged onto a column of Dowex 50W-X4 (sodium form, 200–400 mesh, 1.5×35 cm). The column was eluted with water in the room (4°) at 4.0 ml fractions/1.5 minutes. Fractions 6 to 13 were combined and concentrated under vacuum to ca. 9 ml and lyophilized to powder. This material was chromatographed on three 1.0 mm 20×20 cm Analtech RPS-F plates using 2% ethanol-water as a developing solvent in a cold room (4°). The major UV visible band on each plate at Rf 0.4–0.6 was removed and eluted with 4:1 acetonitrile-water. The eluant was washed with hexane, concentrated under vacuum to ca. 7 ml, filtered through an Acrodisc (Gelman, 0.45 micron CR) and lyophilized to afford the title compound (45 mg) as an amorphous white powder.

IR (Nujol) 3375(br), 1745, 1640, 1590, 1520, 1175, 1040 cm$^{-1}$.

UV(H$_2$O) λ max 223(ε 10510), 255(ε 5670), 295(ε 7240)nm. UV(H$_2$O+NH$_2$OH) λ max ext. 296 (ε ext. 6720)nm. NMR (D$_2$O) δ 1.28(d, CH$_3$CH), 2.94 and 3.10 (two dd, CH$_2$), 3.35(dd, H6), 3.3–3.5 (m, CH$_2$CH$_2$SO$_3$), 4.05(dt, H5), 4.22(p, CH$_3$C$\underline{H}$), 8.02(d, pyridyl H3,H5), 8.76(d, pyridyl H2, H6).

EXAMPLE 7

Sodium (1R,5S,6S)-6-[1(R)-hydroxyethyl]-2-[2-[4-(2-sulfonatoethyl)-1-pyridinium]ethylthio-1-methylcarbapen-2-em-3-carboxylate

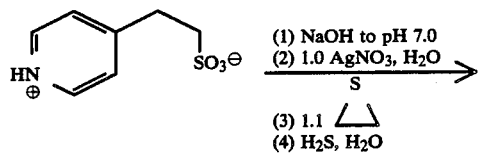

(1) NaOH to pH 7.0
(2) 1.0 AgNO$_3$, H$_2$O
(3) 1.1 △
(4) H$_2$S, H$_2$O

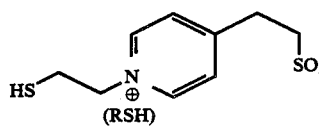
(RSH)

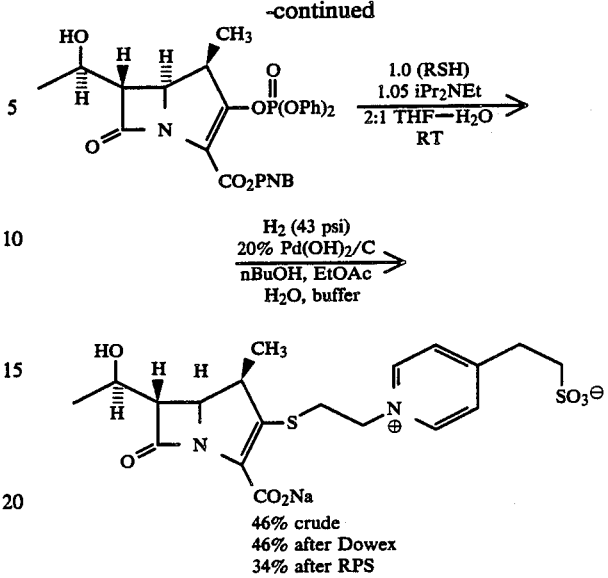

46% crude
46% after Dowex
34% after RPS

Detailed procedures and physical data follow:

STEP 1

Sodium (1R,5S,6S)-6[1(R)-hydroxyethyl]-2-[2-4-(2-sulfonatoethyl)-1-pyridinium]ethylthio-1-methylcarbapen-2-em-3-carboxylate A solution of p-nitrobenzyl (1R,5R,6S)-2-(diphenylphosphono)oxy-6-[1(R)-hydroxyethyl]-1-methylcarbapen-2-em 3-carboxylate (200 mg, 0.336 mmol) and 1-(2-mercaptoethyl)-4-(2-sulfoethyl)pyridinium hydroxide inner salt (83 mg, 0.336 mmol) in tetrahydrofuran (2.0 ml) and water (1.0 ml) was treated at room temperature with N,N-diisopropylethylamine (0.062 ml, 0.353 mmol). After stirring 15 min, the reaction solution was diluted with n-butanol (6.7 ml), ethyl acetate (3.4 ml), water (6.7 ml), and 0.5M pH 6.8 N-methylmorpholine-hydrochloric acid buffer (3.4 ml), mixed with 20% palladium hydroxide on carbon (75 mg), and hydrogenated on a Parr shaker at 43 psi for 75 min. The catalyst was removed by filtration through a celite pad, and the filtrate washed with methylene chloride. The aqueous phase was concentrated under vaccuum to ca. 8 ml and charged onto a column of Dowex 50W-X4(sodium form, 200–400 mesh, 1.5×33 cm). The column was eluted with water in the cold room (4°) at 5.0 ml fractions/2.0 min. Fractions 4 to 10 were combined and concentrated under vacuum to ca. 13 ml and lyophilized to powder. This material was chromatographed on five 0.5 mm×20×20 cm Analtech RPS-F plates using 1% ethanol/water as a developing solvent in a cold room (4°). The major uv visible band on each plate at Rf 0.3–0.5 was removed and eluted with 4:1 acetonitrile-water. The eluant was washed with hexane, concentrated under vacuum to ca. 6 ml, filtered through an Acrodisc (Gelman, 0.45micron CR) and lyophilized to afford the title compound (82.1 mg) as an amorphous white powder.

IR (Nujol) 3375(br) 1745, 1660, 1590, 1220, 1180, 1150, 1040 cm$^{-1}$.

UV (H$_2$O) λ max 255(ε 5,350), 294(ε 7,200)nm. UV (H$_2$O+NH$_2$OH) λ max ext. 297nm (ε ext. 6,630)nm.

NMR (D$_2$O) δ 1.13(d, C$\underline{H}_3$CH), 1.28(d CH$_3$CHOH), 3.1–3.7(m, SCH$_2$, CH$_2$CH$_2$SO$_3$, H1,H6), 3.94(dd, H5), 4.23(p, CH₃C$\underline{H}$OH), 4.9–5.1(m, CH₂N), 8.01(d, pyridyl H3,H5), 8.73($\overline{d}$, pyridyl H2,H6).

EXAMPLE 8

Sodium (1R,5S,6S)-6-[1(R)-hydroxyethyl]-2-[2-(4-sulfonatoaminomethyl-1-pyridinium)ethylthio]-1-methyl carbapen-2-em-3-carboxylate

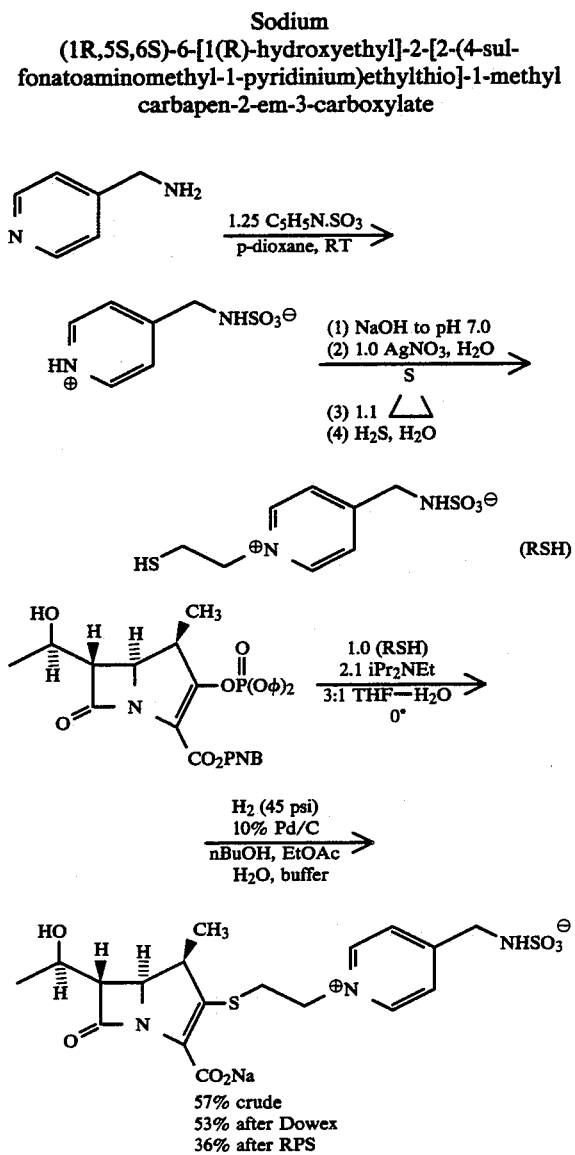

Detailed procedures and physical data follow:

STEP 1

N-(4-pyridylmethyl)sulfamic acid

A suspension of 4-(aminomethyl)pyridine (5.00 g, 46.2 mmol) and sulfur trioxide pyridine complex (9.20 g, 57.8 mmol) in p-dioxane (200 ml) was stirred at ambient temperature. After 1 hr. the suspension was mixed with water (200 ml), filtered, and concentrated under vacuum to a solid. The solid was suspended in water (20 ml), filtered, washed with water, and vacuum dried. The crude product was crystallized from hot water, washed with water, followed by methanol, and vacuum dried to afford a white crystalline product (1.02 g, 12%).

m.p. 227.0°–227.5°

Microanalytical: Calc'd C, 38.29; H, 4.28; N, 14.88; S, 17.04; Found C, 38.26; H, 4.28; N, 14.85; S, 16.80.

STEP 2

1-(2-mercaptoethyl)-4-sulfoaminomethylpyridinium hydroxide, inner salt

A suspension of N-(4-pyridylmethyl)sulfamic acid (800 ml, 4.25 mmol) in water (5.0 ml) was adjusted to pH 7.0 with aqueous sodium hydroxide solution (2.5N). The resulting solution was treated with a solution of silver nitrate (723 ml, 4.25 mmol) in water (3.0 ml) to give a white suspension. Additional water (5.0 ml) was added to facilitate stirring and the mixture was treated with ethylene sulfide (0.280 ml, 4.67 mmol).

After 10 min the supernatant was decanted and the gum resuspended in water and bubbled with hydrogen sulfide. After 10 min bubbling was stopped and the mixture stirred at ambient temperature 1 hr and filtered.

The filtrate was concentrated under vacuum and chromatographed on a Dowex50-X4 (H⁺ cycle) column eluted with water. The eluate was concentrated under vacuum to a paste which was mixed with 2-propanol (5 ml), filtered, 2-propanol washed, and vacuum dried to afford the product as a white solid (0.34 g, 32%).

m.p. 191°–192°

Microanalytical: Calc'd C, 38.69; H, 4.87; N, 11.28; S, 25.82; Found C, 38.63; H, 4.93; N, 11.31; S, 25.75.

NMR(D₂O) δ 3.15(t, J=6 Hz, SCH₂), 4.48(s, CH₂NH), 4.75 (t, J=6 Hz, NCH₂), 8.11(d, J=6.9 Hz, pyridyl H3, H5), 8.79(d, J=6.9 Hz, pyridyl H2, H6).

STEP 3

Sodium (1R,5S,6S)-6-[1(R)-hydroxyethyl]-2-[2-(4-sulfonatoamino-methyl-1-pyridinium)ethylthio]-1-methyl-carbapen-2-em-3-carboxylate A suspension of 1-(2-mercaptoetyl)-4-sulfoaminomethylpyridinium hydroxide, inner salt (84 mg, 0.34 mmol) and vinyl phosphate (200 mg, 0.34 mmol) in tetrahydrofuran (2.0 ml) and water (0.68 ml) was cooled in an ice bath and treated with N,N-diisopropylethylamine (0.124 ml, 0.70 mmol). After 15 min the solution was mixed with n-butanol (6.7 ml), ethyl acetate (3.9 ml), water (6.7 ml), pH 7.0 N-methylmorpholine-HCl buffer (0.5M, 3.9 ml), and 10% palladium on carbon (80 ml) and hydrogenated on a Parr shaker at 45 psi H₂. After 1.25 hr the mixture was removed from the shaker, filtered, the aqueous phase isolated, and washed with methylene chloride.

The concentrated aqueous phase was chromatographed on a Dowex 50-X4 (Na⁺ cycle) column eluted with water in the cold room (4°). The product solution was isolated, concentrated, and chromatographed on three 1,000 micron thick (20×20 cm) RPS-F plates (Analtech) developed in water. The desired product bands were isolated, extracted with acetonitrile-water (100 ml, 5:1), and this solution washed with hexane. The solution was concentrated under vacuum and lyophilized to afford the product as an off-white fluff (87.8 mg).

IR (Nujol) 3350(br), 1748, 1640, 1585, 1180, 1038 cm⁻¹.

UV (H₂O) λ max 219(ε 8730), 257(ε 5710), 295(ε 6960) nm.

UV (H₂O+NH₂OH) λ max. ext. 297(ε ext. 6360) nm.

NMR (D₂O) δ 1.13(d, 1-CH₃), 1.28(d, CH₃CHOH), 3.21(qd, H1), 3.28(td, SC/ Hb), 3.41(dd, H6), 3.54(ddd, SCHa$\underline{Hb}$), 3.94(dd, H5), 4.24(p, CH₃C$\underline{H}$OH), 4.49(s, CH₂NH). 4.7–4.9(m, CH₂N), 8.09(d, pyridyl H3,H5), 8.76(d, pyridyl H2, H6)

EXAMPLE 9

Sodium (5R,6S)-6-[1(R)-hydroxyethyl]-2-[2-[4-[N-(2-thiazolyl)-sulfamoylatomethyl]-1-pyridinium]ethylthio]carbapen-2-em-3-carboxylate

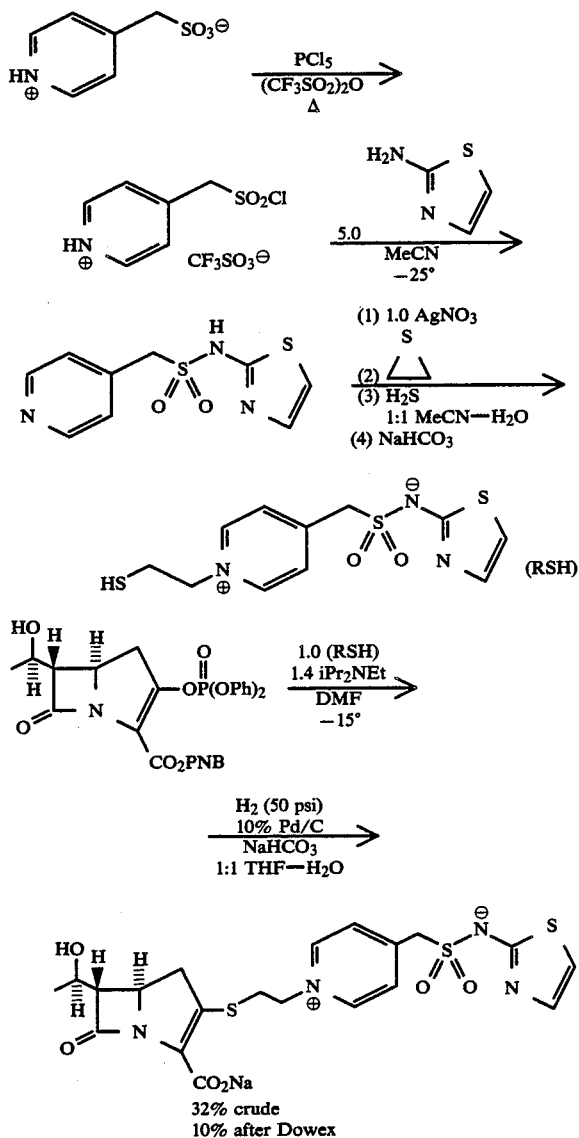

Detailed procedures and physical data follow:

STEP 1

4-[N-(2-Thiazolyl)sulfamoylmethyl]pyridine

A suspension of finely ground 4-pyridylmethane sulfonic acid (2 g) and phosphorous pentachloride (2.5 g) in trifluoromethanesulfonic anhydride (40 ml) was refluxed with stirring for 16 hours. The product sulfonyl chloride formed a heavy oily layer. The excess solvent was decanted off and the residue blown with nitrogen for a few minutes then pumped under vacuum until solidified. The solid sulfonyl chloride intermediate was dissolved in anhydrous acetonitrile (60 ml) and added dropwise over 15 minutes to a stirred solution of 2-aminothiazole (5 g) in acetonitrile (50 ml) at −15°. After 30 minutes the mixture was allowed to warm to room temperature and the product was filtered. The filter case was dissolved in hot 95% ethanol (60 ml) and the solution concentrated to half volume and chilled. The crystalline product was collected and dried to afford 1.04 g of a solid.

mp softens 195°, dec. 206°.

NMR(D₂O) δ 4.71(s, CH₂SO₃), 6.67(d, thiazolyl H5), 7.07(d, thiazolyl H4), 8.01(d, pyridyl H3 and H5), 8.65(d, pyridyl H2 and H6).

STEP 2

1-(2-Mercaptoethyl)-4-[N-(2-thiazolyl)sulfamoylmethyl]pyridinium hydroxide, inner salt To a stirred solution of 4-[N-(2-thiazolyl)sulfamoylmethyl]pyridine (150 mg, 0.59 mmol) in 1:1 acetonitrile-water (4 ml) at 0° was added silver nitrate (100 mg, 0.59 mmol). After 10 minutes, ethylene sulfide (0.036 ml, 0.6 mmol) was added and the mixture was stirred at 0° for one hour. The solvents were removed under vacuum and the residual yellow solid was triturated with water and filtered. The solid was resuspended in water (15 ml) and stirred while passing in a slow stream of hydrogen sulfide for 15 minutes. The silver sulfide was removed by filtration and the nitrogen. The solution was adjusted to pH 6.7 with sodium bicarbonate then evaporated under vacuum to afford the crude product as a resin (180 mg). NMR shows approximately 80% of the desired product.

NMR(D₂O) δ 3.2(t, CH₂S), 6.9 and 7.26(two d, thiazolyl H5 and H4), 8.24(pyridyl H3 and H5), 8.96(pyridyl H2 and H6).

STEP 3

Sodium (5R,6S)-6-[1(R)-hydroxyethyl]-2-[2-[4-[N-(2-thiazolyl)-sulfamoylatomethyl]-1-pyridinium]ethylthio]carbapen-2-em-3-carboxylate To a stirred solution of 1-(2-mercaptoethyl)-4-[N-(2-thiazolyl)sulfamoylmethyl]pyridinium hydroxide inner salt (113 mg, 0.3 mmol) in DMM (2 ml) at 0° was added the solid bicyclic vinyl phosphate (163 ml, 0.3 mmol) followed by N,N-diisopropylethylamine (0.08 ml, 0.45 mmol) dropwise over 2 minutes. The solution was stirred at 0° for 15 minutes then precipitated onto celite by the addition of ethyl ether (90 ml). The solids were filtered and washed with ether. The filter cake was eluted with 1:1 tetrahydrofuran-water (30 ml) and the filtrate collected in a hydrogenation bottle. Sodium bicarbonate (42 mg, 0.5 mmol) and 10% Pd/C catalyst were added and the mixture was shaken under hydrogen at 45 psi for 2.5 hours. The catalyst was filtered off and the filtrate extracted with other. The aqueous phase was concentrated to half volume and applied to a column (1.5×32 cm) of Dowex 50 resin (Na cycle) that was cooled by a jacket of circulating ice-water. The column was eluted with water and the fractions monitored by ultraviolet absorption. A broad peak was obtained in which the front part was more heavily contaminated with diphenyl phosphate than the trailing part. The center fraction and the trailing fraction were isolated separately and the center fraction was concentrated and immediately rechromatograped on the same column. The trailing fraction from the rechromatography was combined with the original trailing fraction, concentrated and lyophilized to afford the product as an amorphous solid (38 mg). The lyophilized center fraction from the rechromatography gave additional product (23 mg).

UV($H_2O$) λ max 262(ε 10740), 300(sh, ε 7130, 62% $NH_2OH$ ext.)nm.

NMR($D_2O$) δ 1.33(d, $CH_3$CHOH), 3.11(m, $CH_2$), 3.30-3.64(m, $SCH_2$), 3.43(dd, H6), 4.16(dt, H5), 4.27(p, $CH_3C$HOH), 4.84(HOD), 4.88(m, $CH_2N$), 7.89(d, thiazolyl H5), 8.10(d, pyridyl H3,H5), 8.85(d, pyridyl H2,H6).

EXAMPLE 10

Sodium (1R,5S,6S)-6-[1(R)-hydroxyethyl]-2-[2-[4-[N-(2-thiazolyl)sulfamoylatomethyl]-1-pyridinium]ethylthio]-1-methylcarbapen-2-em-3-carboxylate

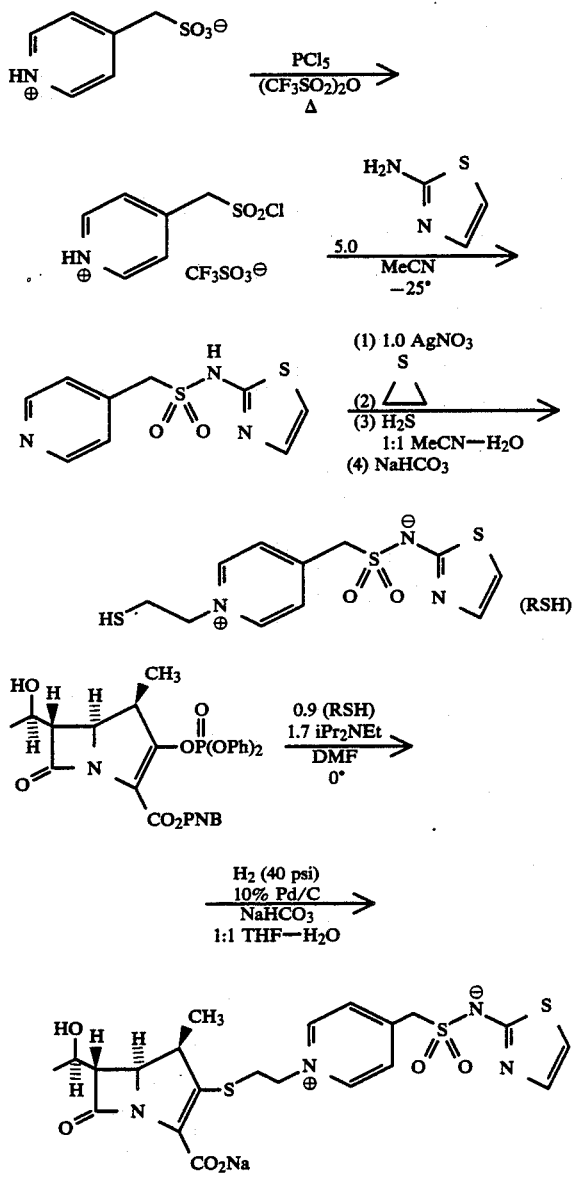

Procedure and physical data follow.

STEP 1

Sodium (1R,5S,6S)-6-[1(R)-hydroxyethyl]-2-[2-[4-[N-(2-thiazolyl)sulfamoylatomethyl]-1-pyridinium]-ethylthio]-1-methylcarbapen-2-em-3-carboxylate To a stirred solution of 1-(2-mercaptoethyl)-4-[N-(2-thiazolyl)sulfamoylmethyl]pyridinium hydroxide inner salt (60 mg, 0.16 mmol) in DMF (1 ml) at 0° was added the solid 1-methyl bicyclic vinyl phosphate (90 mg, 0.17 mmol) followed by N,N-diisopropylethylamine (0.05 ml, 0.28 mmol). The solution was stirred at 0° for 30 minutes then diluted with 1:1 tetrahydrofuran-water (7 ml). Sodium bicarbonate (14 mg) and 10% Pd/C (90 mg) were added and the mixture was shaken under hydrogen at 40 psi for 2 hours. The catalyst was filtered off and the filtrate extracted with ether. The aqueous phase was concentrated and applied to a column (1.5×20 cm) of Dowex 50 resin (Na cycle) that was cooled by a jacket of circulating ice-water. The column was eluted with water and the fractions monitored by ultraviolet absorption. A single product peak was observed. The trailing portion of the peak was concentrated under vacuum and lyophilized to provide the product as an amorphous solid (13 mg).

UV($H_2O$) λ max 265(ε 9420), 300(sh, ε 6390, 49% $NH_2OH$ ext.)nm.

NMR($D_2O$) δ 1.12(d, 1-$CH_3$), 1.26(d, $CH_3$CHOH), 3.2(m, SC/ Hb and H1), 3.39(dd, H6), 3.49(td, $S$CHa/ ), 3.98(dd, H5), 4.20(p, $CH_3C$ OH), 4.77(HOD), 4.79(m, $CH_2N$), 7.81(d, thiazolyl H5), 8.00(d, pyridyl H3,H5), 8.73(d, pyridyl H2,H6).

EXAMPLE 11

Sodium (1R,5S,6S)-2-[2-(3-carboxylato-1-pyridinium)ethylthio]-6-[1(R)-hydroxyethyl]-1-methylcarbapen-2-em-3-carboxylate

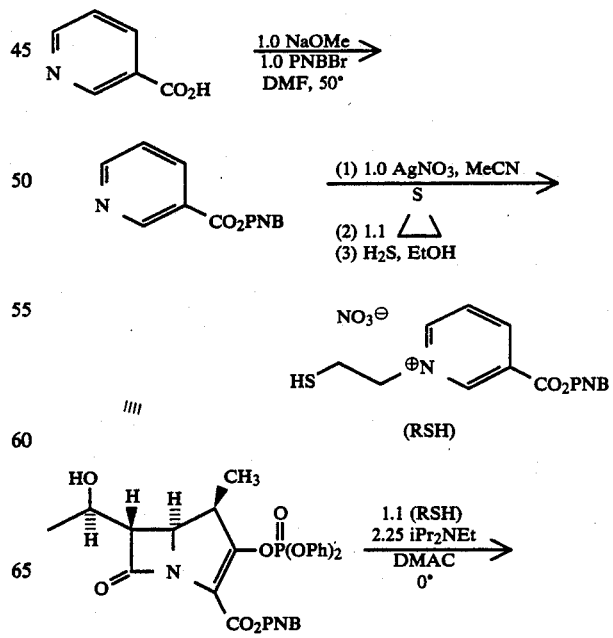

-continued

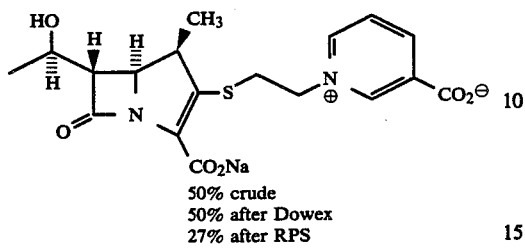

50% crude
50% after Dowex
27% after RPS

IR (Nujol) 3350(br), 1755, 1645, 1610, 1140 cm$^{-1}$.
UV (H$_2$O) λ max 294 (ε 6890)nm.
UV (H$_2$O+NH$_2$OH) λ max ext. 294(ε ext. 6070) nm.
NMR (D$_2$O) δ 1.12(d, 1-CH$_3$), 1.27(d, CH$_3$CHOH), 3.18–3.4(m, H1), 3.42(dd, H6), 3.5–3.7(m, SCH$_2$), 3.88(dd, H5), 4.24(p, CH$_3$CHOH), 4.9–5.1(m, CH$_2$N), 8.07(t, pyridyl H5), 8.86–8.95(m, pyridyl H4,H6), 9.27(s, pyridyl H2).

EXAMPLE 12

Sodium (1R,5S,6S)-2-[2-(3-carboxylatomethyl-1-pyridinium-)ethyl-thio]-6-[1(R)-hydroxyethyl]-1-methylcarbapen-2-em-3-carboxylate

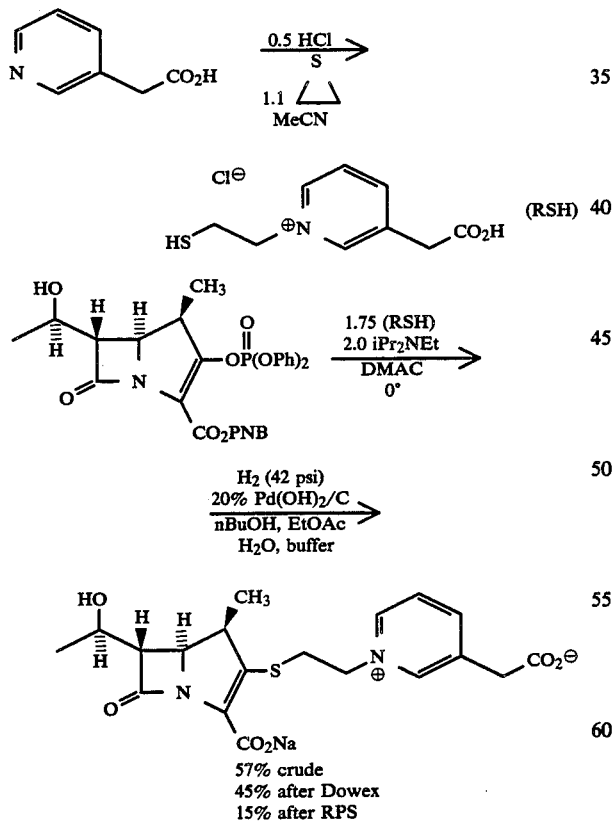

57% crude
45% after Dowex
15% after RPS

UV (H$_2$) λ max 274(ε 4980), 295(ε 5210) nm.
UV (H$_2$O+NH$_2$OH) λ max ext. 298(ε ext. 4920) nm.
NMR (D$_2$O) δ 1.13(d, 1-CH$_3$), 1.27(d, CH$_3$CHOH), 3.2(m, H1), 3.40(dd, H6), 3.55–3.65(m, SCH$_2$), 3.79(s, pyridyl CH$_2$), 391(dd, H5), 4.22(p, CH$_3$CHOH), 8.00(dd, pyridyl H5), 8.49(d, pyridyl H6), 8.72(d, pyridyl H4), 8.79(s, pyridyl H2).

EXAMPLE 13

Sodium (5R,6S)-2-[2-[4-(2-carboxylatoethyl)-1-pyridinum]-ethylthio]-6-[1(R)-hydroxyethyl]carbapen-2-em-3-carboxylate

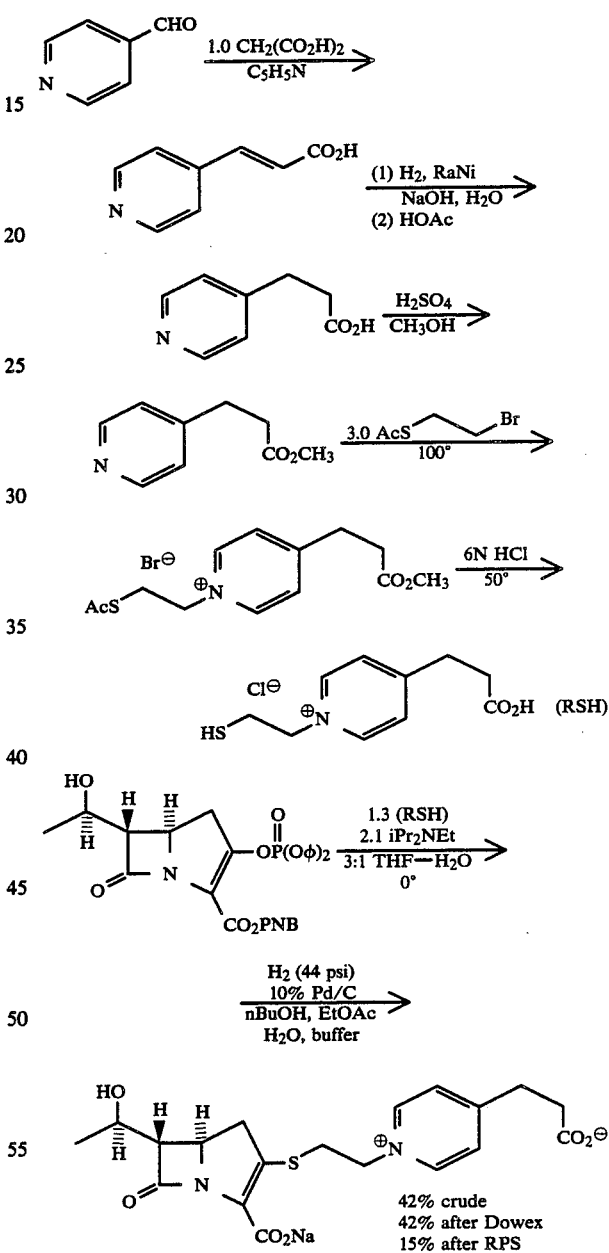

42% crude
42% after Dowex
15% after RPS

IR (Nujol) 3400(br), 1750, 1640, 1580, 1255, 1130 cm$^{-1}$.
UV (H$_2$O) λ max 223(ε 7650), 252(ε 5120), 294(ε 5200) nm.
UV (H$_2$O+NH$_2$OH) λ max. ext. 298(ε ext. 4780) nm.
NMR (D$_2$O) δ 1.28(d, CH$_3$CH), 2.67(t, CH$_2$CO$_2$), 2.92 and 3.07 (two dd, CH$_2$), 3.20(t, pyridyl CH$_2$), 3.33 and 3.51(two td, SCH$_2$), 3.4(m, H6), 4.03(dt, H5), 4.21(p, CH₃C$\underline{H}$OH), 4.7–4.9(m, C$\underline{H_2}$N), 7.92(d, pyridyl H3,H5), 8.70(d, pyridyl H2,H6).

EXAMPLE 14

Sodium
(1R,5S,6S)-2-[2-[4-(2-carboxylatoethyl)-1-pyridiniumethylthio]-6-[1(R)-hydroxyethyl]-1-methylcarbapen-2-em-3-carboxylate

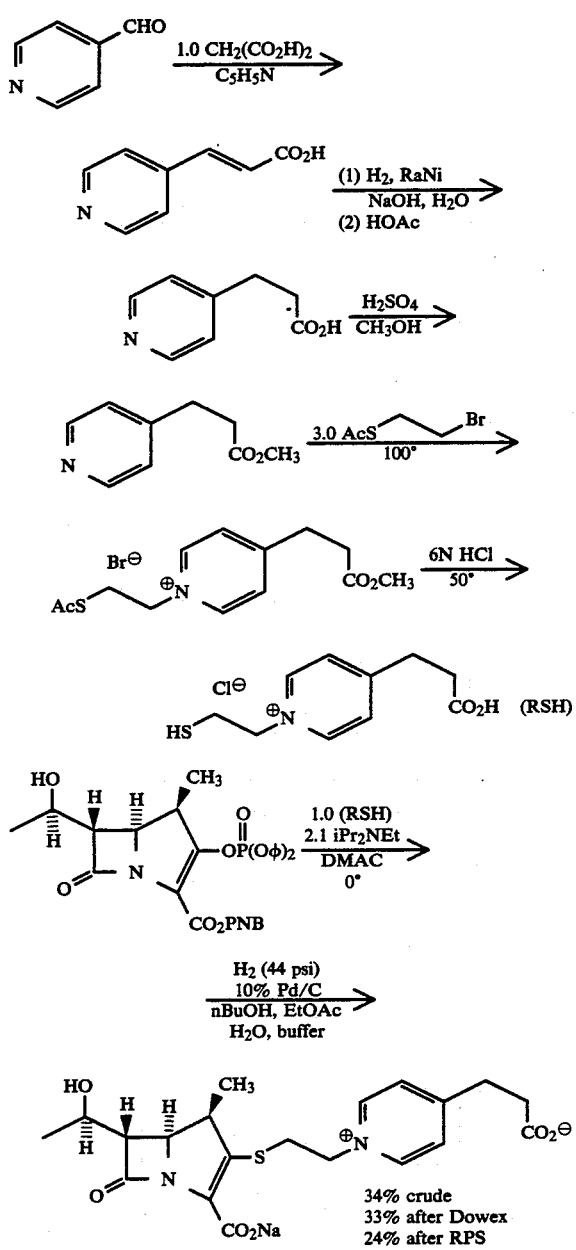

34% crude
33% after Dowex
24% after RPS

IR (Nujol) 3350(br), 1750, 1640, 1580, 1140 cm⁻¹.
UV (H₂O) λ max 226(ε 8290), 253(ε 5650), 296(ε 6740) nm.
UV (H₂O+NH₂OH) λ max. ext. 298 nm (ε ext. 6280)nm.
NMR (D₂O) δ 1.12(d, 1-CH₃), 1.28(d, C$\underline{H_3}$CHOH), 2.67(t, C$\underline{H_2}$CO₂), 3.20(t, C$\underline{H_2}$CH₂CO₂), 3.1–3.2(m, H1), 3.27(td, SC$\underline{H_a}$Hb), 3.40(dd, H6), 3.52(ddd, SCHa$\underline{H_b}$), 3.91(dd, H5), 4.23(p, CH₃C$\underline{H}$OH), 4.6–4.8(m, C$\underline{H_2}$N), 7.92(d, pyridyl H3,H5), 8.68(d, pyridyl H2,H6).

EXAMPLE 15

Sodium
(1R,5S,6S)-2-[2-(3-sulfonato-1-pyridinum)ethylthio]-6-[1(R)-hydroxyethyl]-1-methylcarbapen-2-em-3-carboxylate

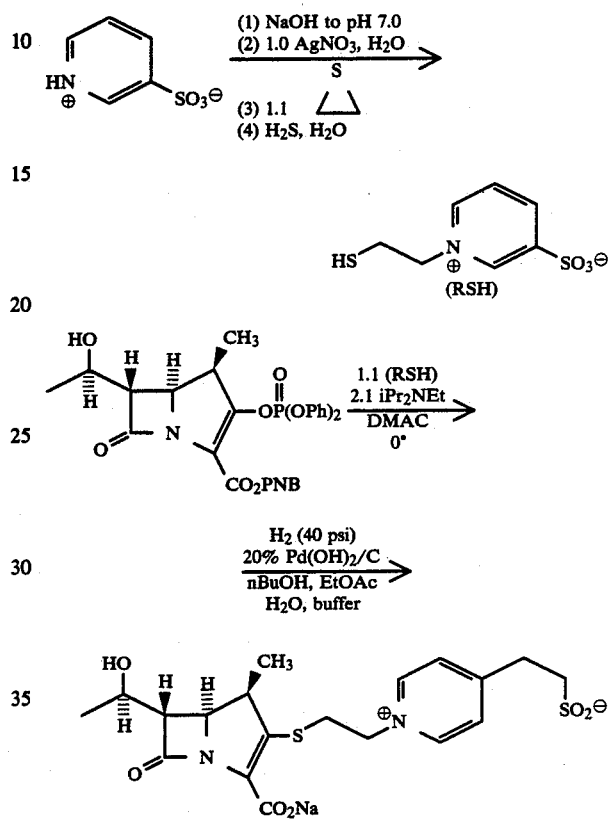

40% crude
40% after Dowex
38% after RPS

IR (Nujol) 3400(br), 1750, 1590, 1555, 11230, 1142, 1050 cm⁻¹.
UV (H₂O) λ max 270(br, ε 5,500), 293 (ε 6,440)nm.
UV (H₂O+NH₂OH) λ max ext. 295 (ε 5,620)nm.
NMR (D₂O) δ 1.12(d, CH₃CH), 1.27(d, C$\underline{H_3}$CHOH), 3.17(qd, H1), 3.36 (td, SC$\underline{H_a}$Hb), 3.41(dd, H6), 3.58(ddd, SCHa$\underline{H_b}$), 3.98(dd, H5), 4.20(p, CH₃C$\underline{H}$OH), 4.9–5.1(m, C$\underline{H_2}$N), 8.17(dd, pyridyl H5), 8.92–9.01 (m, pyridyl H4,H6), 9.40(s, pyridyl H2).

EXAMPLE 16

Sodium
(1R,5S,6S)-2-[2-(4-sulfonato-1-pyridinium)ethylthio]-6-[1(R)-hydroxyethyl]-1-methylcarbapen-2-em-3-carboxylate

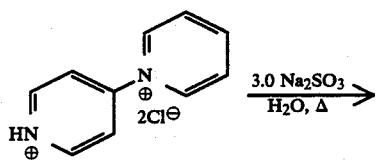

-continued

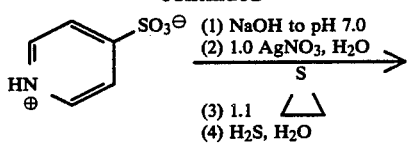

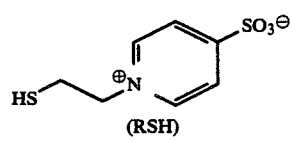

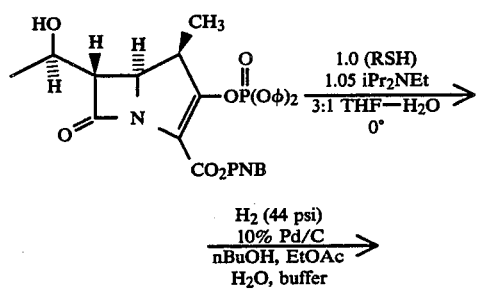

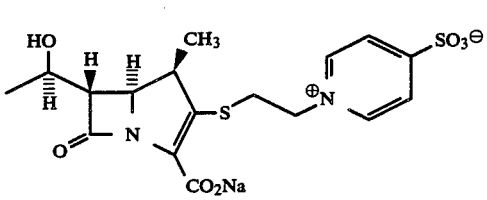

IR (Nujol) 3450(br), 1737, 1630, 1590, 1218, 1035 cm$^{-1}$.

UV (H$_2$O) λ max 227(ε 9150), 273(ε 5880), 295(ε 6550)nm.

NMR (D$_2$O) δ 1.14(d, 1-CH$_3$), 1.29(d, CH$_3$CHOH), 3.18(qd, H1), 3.30 and 3.58(two td, SCH$_2$), 3.42(dd, H6), 3.98(dd, H5), 4.22(p, CH$_3$CHOH), 4.9-5.0(m, CH$_2$N), 8.39(d, pyridyl H3,H5), 9.05(d, pyridyl H2,H6).

EXAMPLE 17

Sodium (1R,5S,6S)-2-[2-(2-sulfonatomethyl-1-pyridinium)ethylthio]-6-[1(R)-hydroxymethyl]-1-methylcarbapen-2-em-3-carboxylate

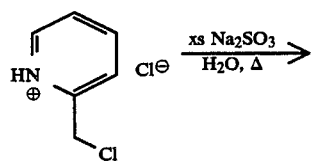

-continued

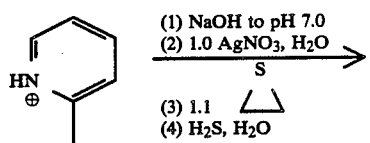

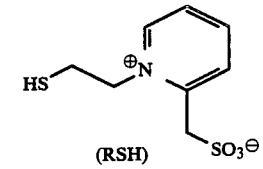

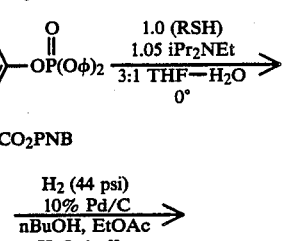

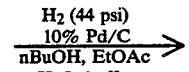

17% crude
17% after Dowex
12% after RPS

IR (Nujol) 3425(br), 1740, 1625, 1590, 1235, 1040 cm$^{-1}$.

UV (H$_2$O) λ max 274(ε 9170), 295(ε 7470)nm.

UV (H$_2$O+NH$_2$OH) λ max ext. 298(ε ext. 6430)nm.

NMR (D$_2$O) δ 1.14(d, 1-CH$_3$), 1.28(d, CH$_3$CHOH), 3.18(qd, H1), 3.33(td, SCHaHb), 3.42(dd, H6), 3.57(ddd, SCHaHb), 3.95(dd, H5), 4.22(p, CH$_3$CHOH), 4.79 and 4.95(d, CH$_2$SO$_3$), 5.0-5.2(m, CH$_2$N), 8.03(dt, pyridyl H5), 8.17(d, pyridyl H3), 8.60 (t, pyridyl H4), 8.86(d, pyridyl H6).

EXAMPLE 18

Sodium (1R,5S,6S)-2-[2-(3-sulfonatomethyl-1-pyridinium)ethylthio]-6-[1(R)-hydroxyethyl]-1-methylcarbapen-2-em-3-carboxylate

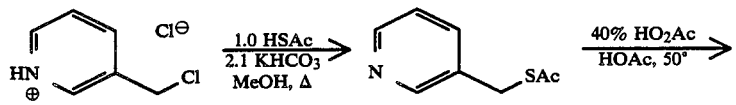

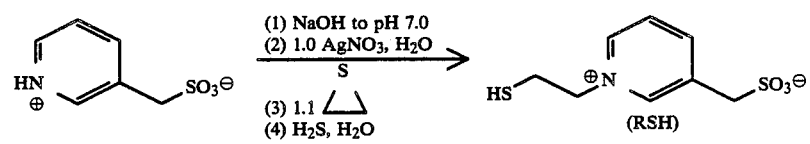

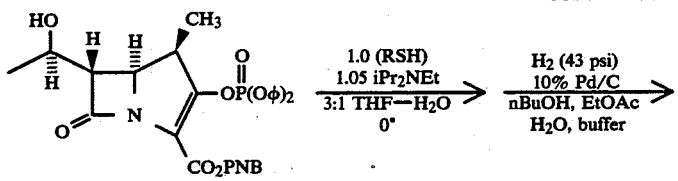

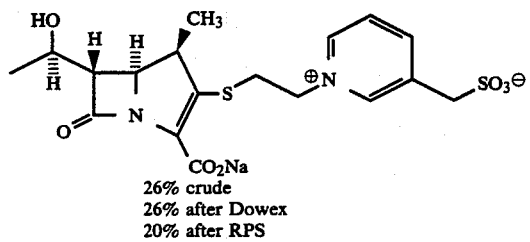

IR (Nujol) 3400(br), 1755, 1715, 1620, 1225, 1145, 1040 cm$^{-1}$.

UV (H$_2$O) λ max 273(ε 5900), 295(ε 6560)nm.

UV (H$_2$O+NH$_2$OH) λ max ext. 297(ε ext. 5970)nm.

NMR (D$_2$O) δ 1.13(d, 1-CH$_3$), 1.28(d, CH$_3$CHOH), 3.15(dq, H1), 3.32(td, SCH$_a$Hb), 3.41(dd, H6), 3.55(ddd, SCHaH$_b$), 3.95(dd, H5), 4.22(p, CH$_3$CHOH), 4.43(s, CH$_2$SO$_3$), 4.8–5.0(m, CH$_2$N), 8.09(dd, pyridyl H5), 8.66(d, pyridyl H4), 8.86(d, pyridyl H6), 8.95(s, pyridyl H2).

EXAMPLE 19

Sodium (1R,5S,6S)-6-[1(R)-hydroxyethyl]-2-[2-(2-hydroxymethylsulfonatomethyl-1-pyridinium)ethylthio]-1-methyl-carbapen-2-em-3-carboxylate

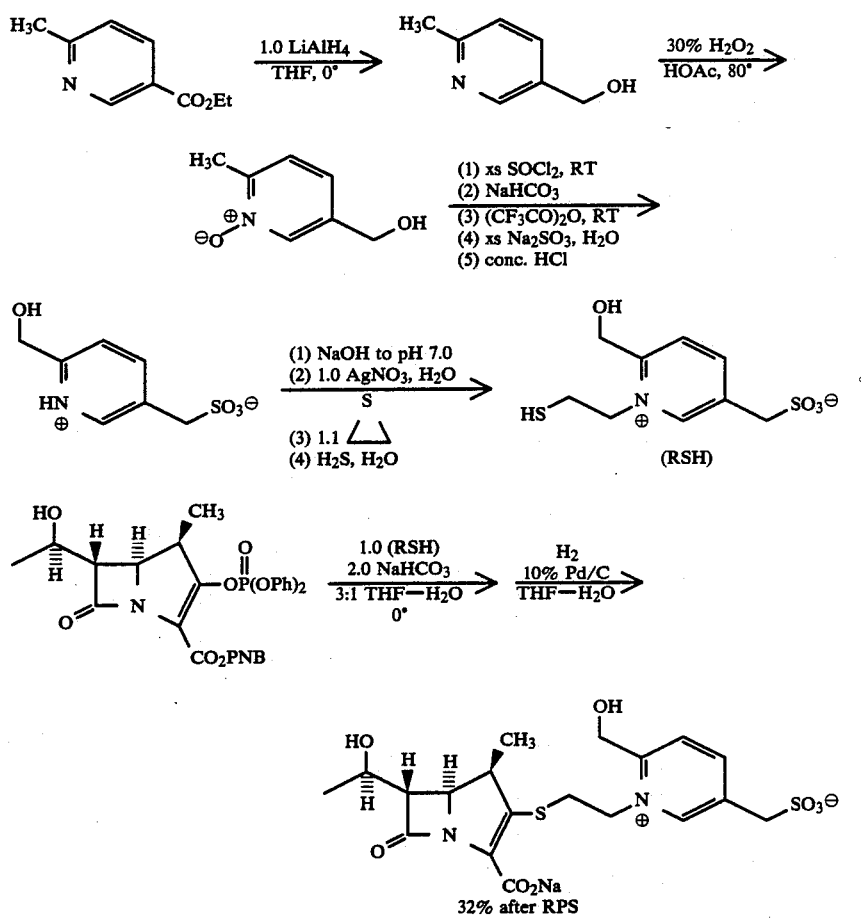

UV (H$_2$O) λ max 277(ε 10,300) 294(sh, ε 8300) nm.

UV (H$_2$O+H$_2$OH) λ max ext. 295(ε ext. 5880) nm.

NMR (D$_2$O) δ 1.18(d, 1-CH$_3$), 1.32(d, CH$_3$CHOH), 3.21(m, H1), 3.46(dd, H6), 3.3–3.72(m, SCH$_2$), 3.98(dd, H5), 4.27(p, CH$_3$CHOH), 4.45(s, CH$_2$SO$_3$), 4.84(HOD), 4.95(t, CH₂N), 5.21(s, C$\underline{H_2}$OH), 8.28(d, pyridyl H3), 8.68(d, pyridyl H4), 8.94(s, pyridyl H6).

EXAMPLE 20

Sodium (1R,5S,6S)-6-[1(R)-hydroxyethyl]-2-[2-[3-(2-sulfonatoethyl)-1-pyridinium]ethylthio]-1-methylcarbapen-2-em-3-carboxylate UV(buffer+NH₂OH) λ max ext. 297.5(ε ext. 6920)nm.

NMR(D₂O) δ 1.14(d, 1-CH₃), 1.28(d, C$\underline{H_3}$CHOH), 3.22(m, H1), 3.26-3.54(two m, SC$\underline{H_2}$), 3.33 (s, C$\underline{H_2}$CH₂SO₃), 3.42(dd, H6), 3.95(dd, H5), 4.23(m, CH₃C$\underline{H}$OH), 4.77(HOD), 4.87(m, CH₂N), 8.02(dd, pyridyl $\overline{H5}$), 8.56(d, pyridyl H4), 8.72(d, pyridyl H6), 8.83(s, pyridyl H2).

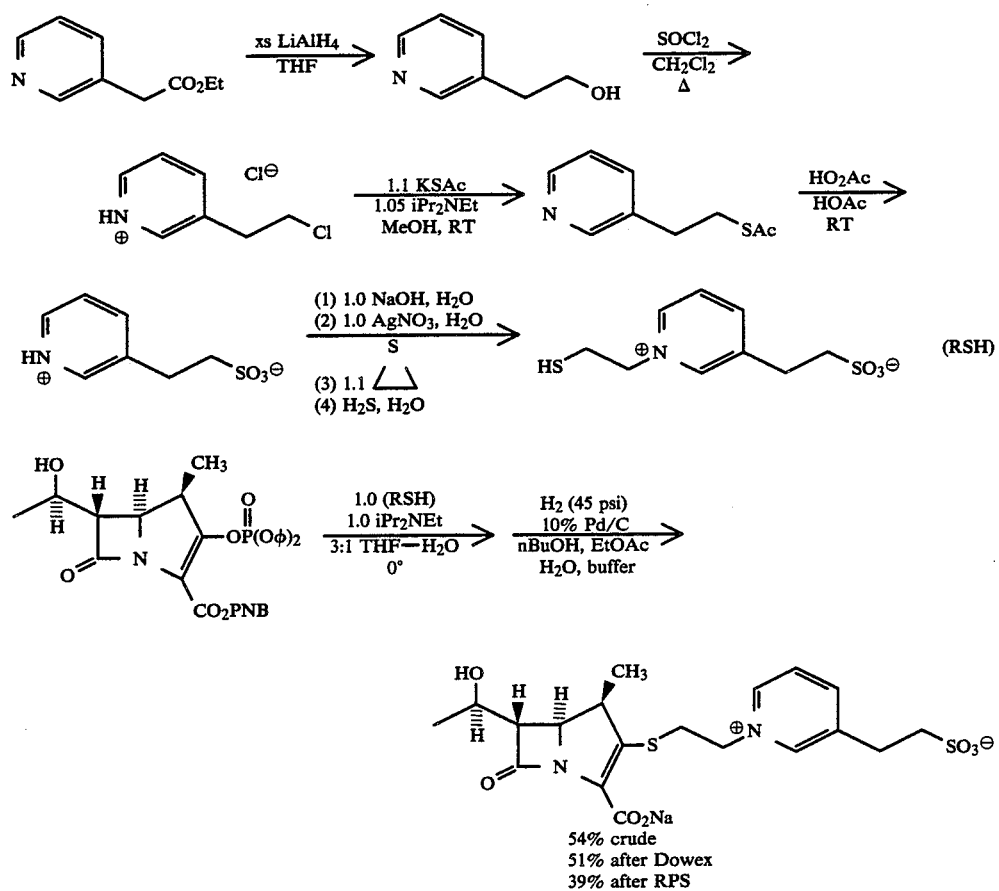

IR (Nujol) 3410(br), 1745, 1587, 1400, 1180, 1040 cm⁻¹.

UV (0.05M pH 7.0 MOPS buffer) λ max 295 (ε 7720), 272.5(ε 6990), 267.5(ε 6920)nm.

EXAMPLE 21

Sodium(1R,5S,6S)-2-[2-[4-(3-sulfonatopropyl)-1-pyridinium]-ethylthio]-6-[1(R)-hydroxyethyl]-1-methylcarbapen-2-em-3-carboxylate

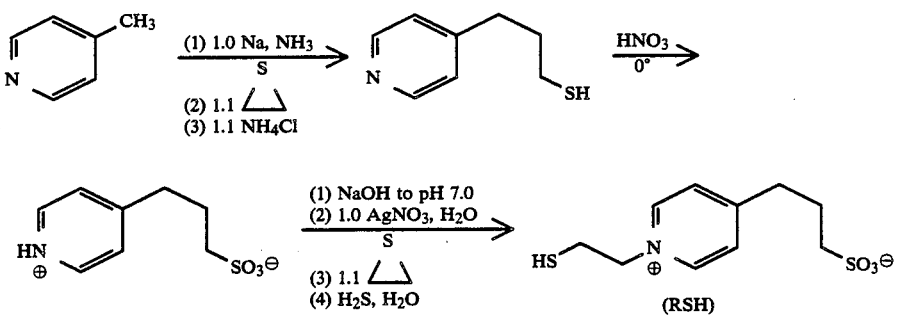

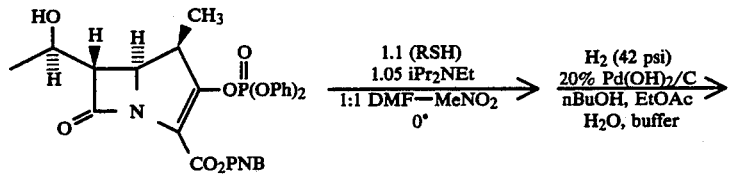

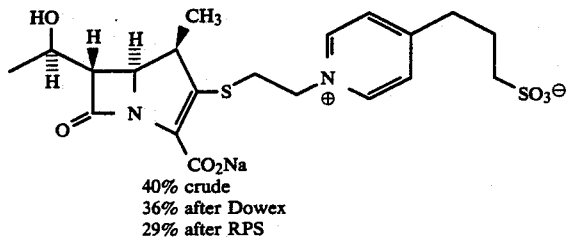

40% crude
36% after Dowex
29% after RPS

IR (Nujol) 3375 (br), 1742, 1638, 1590, 1175, 1038 cm$^{-1}$.

UV (H$_2$O) λ max 225 (ε 10000), 256(ε 5050), 296(ε 6720)nm.

UV (H$_2$O+NH$_2$OH) λ max ext. 297 (ε 6360)nm.

NMR (D$_2$O) δ 1.12(d, 1-CH$_3$), 1.28(d, CH$_3$CHOH), 2.21(p, CH$_2$CH$_2$CH$_2$), 3.00(t, pyridyl CH$_2$), 3.13(t, CH$_2$SO$_3$), 3.17(dq, H1), 3.29(td, SCHaHb), 3.39(dd, H6), 3.54(ddd, SCHaHb), 3.89(dd, H5), 4.23 (p, CH$_3$CHOH), 4.6–4.8(m, CH$_2$N), 7.97(d, pyridyl, H3,H5), 8.72(d, pyridyl H2,H6).

EXAMPLE 22

Sodium (5R,6S)-6-[1(R)-hydroxyethyl]-2-[2-[4-[1(R,S)-sulfonatoethyl]-1-pyridinium]ethylthio]carbapen-2-em-3-carboxylate

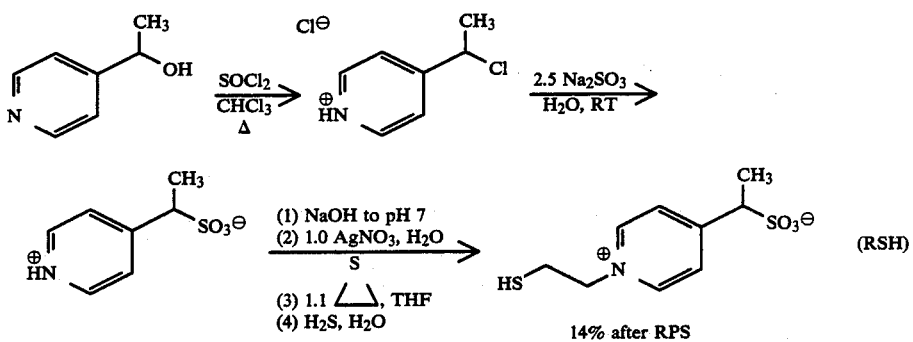

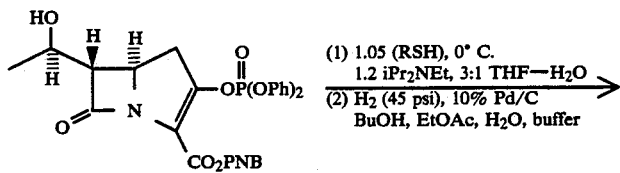

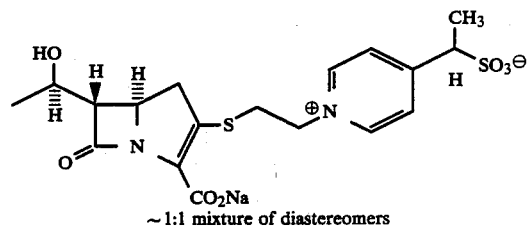

~1:1 mixture of diastereomers
36% crude
29% after Dowex
23% after RPS

UV (0.05M pH 7.0 MOPS buffer) λ max 295 (ε 6780)nm.

UV (buffer+NH$_2$OH) λ max ext 298 (ε ext 5840)nm

NMR (D$_2$O) δ 1.30(two d's, CH$_3$CH), 1.8(m, CH$_3$CHSO$_3$), 3.03(m, CH$_2$), 3.38(dd, H6), 3.32–3.61(m, SCH$_2$), 4.05(m, H5), 4.22(m, CH$_3$CHOH), 4.59(m, CH$_3$CHSO$_3$), 4.82(HOD), 4.87(m, CH$_2$N), 8.16(m, pyridyl H3,H5), 8.87(d, pyridyl H2, H6).

EXAMPLE 23

Sodium (1R,5S,6S)-6-[1(R)-hydroxyethyl]-2-[2-[4-[1(R,S)-sulfonatoethyl]-1-pyridinium]ethylthio]-1-methylcarbapen-2-em-3-carboxylate NMR (D$_2$O) δ 1.10(two d's, CH$_3$CH), 1.25(two d's, CH$_3$CHOH), 1.76(m, CH$_3$CHSO$_3^-$), 3.14(m, CH$_3$CH), 3.21–3.57(m, SCH$_2$), 3.37(dd, H6), 3.88(m, H5), 4.18(m, CH$_3$CHOH), 4.54(m, CH$_3$CHSO$_3$), 4.80(HOD), 4.85(m, CH$_2$N), 8.09(m, pyridyl H3,H5), 8.81(m, pyridyl H2,H6).

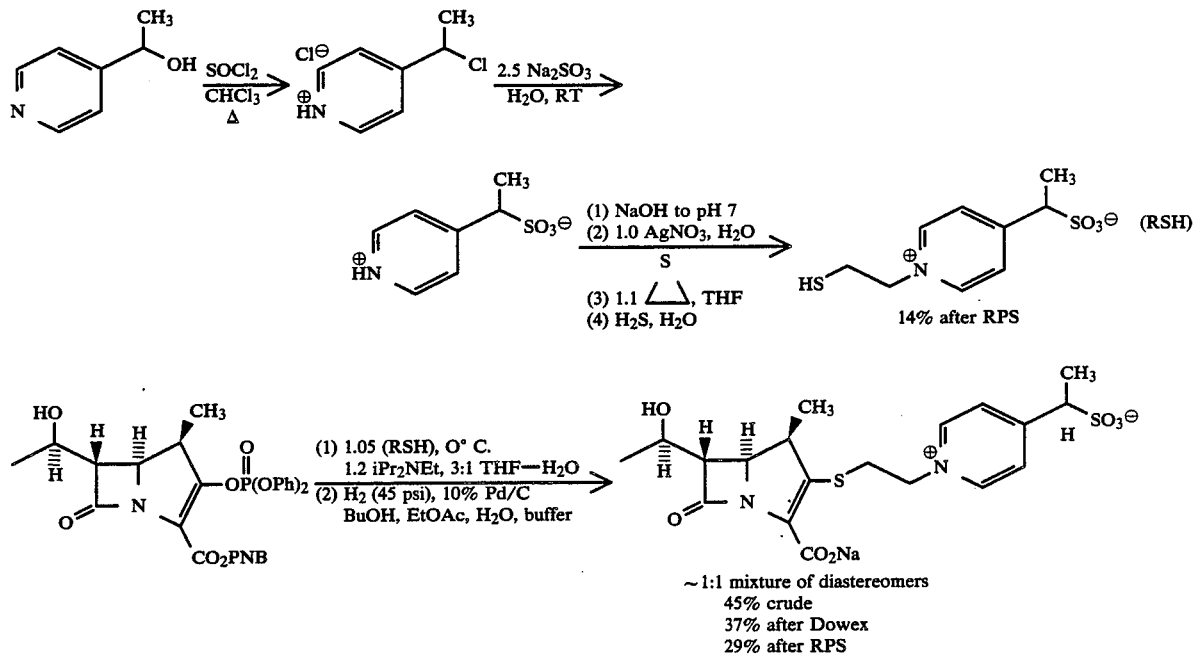

IR (Nujol) 3400(br), 1744, 1640, 1590, 1180 1027 cm$^{-1}$.

UV (0.05M pH 7.0 MOPS buffer) λ max 293 (ε 7870)nm.

UV (buffer+NH$_2$OH) λ max ext. 295.5(ε ext. 6730)nm.

EXAMPLE 24

Sodium (5R,6S)-2-[1(R)-hydroxyethyl]-2-[2-(2-methyl-4-sulfonatomethyl-1-pyridinium)ethylthio]carbapen-2-em-3-carboxylate

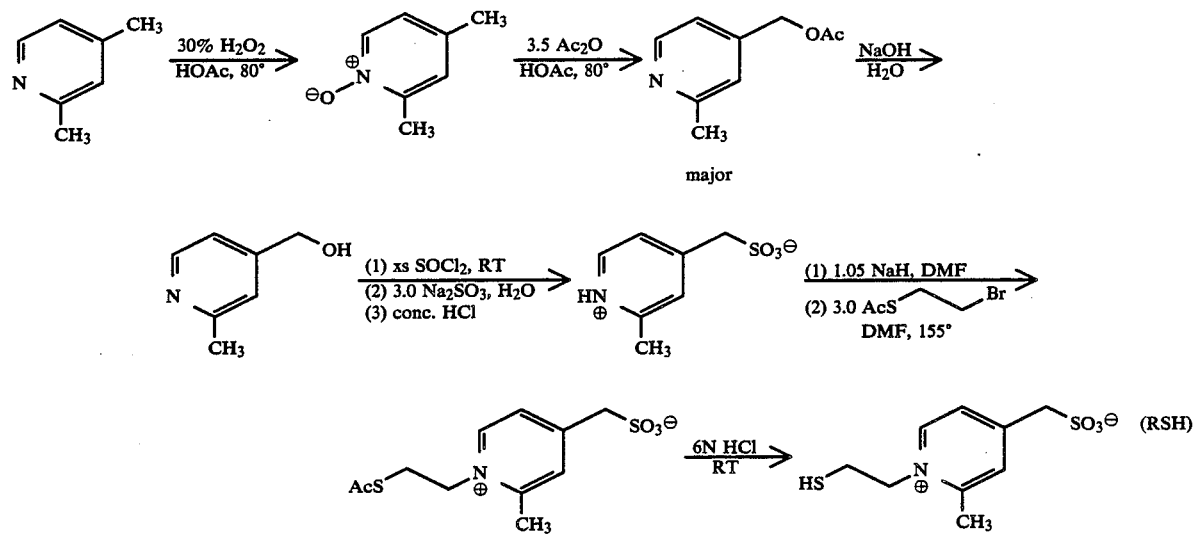

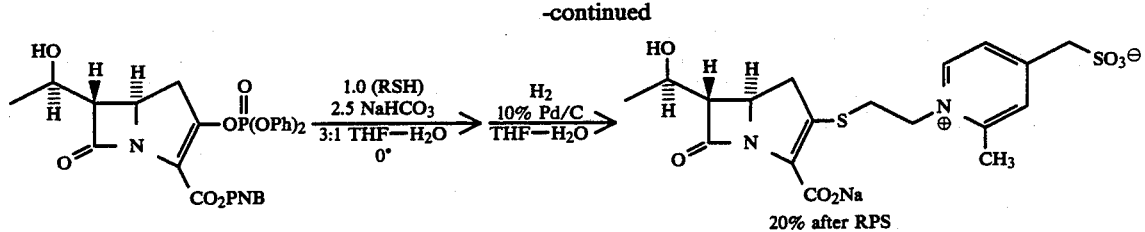

UV (H$_2$O) λ max 272(ε 8000), 295(ε 7110, 84% NH$_2$OH ext.) nm.

NMR (D$_2$O) δ 1.33(d, C$\underline{H}_3$CHOH), 2.97(s, CH$_3$), 3.03 and 3.15(two dd, CH$_2$), 3.43(dd, H6), 3.30–3.66(m, SCH$_2$), 4.13(dt, H5), 4.28(p, CH$_3$C$\underline{H}$OH), 4.51(s, CH$_2$SO$_3$), 4.85 (HOD), 4.89(m, CH$_2$N), 7.97(d, pyridyl H5), 8.03(s, pyridyl H3), 8.77(d, pyridyl H6).

UV (H$_2$O) λ max 272(ε 7600), 293(ε 7000) nm.
UV (H$_2$O+NH$_2$OH) λ max ext. 295(ε ext. 5770) nm.

NMR (D$_2$O) δ 1.32(d, C$\underline{H}_3$CHOH), 2.66(s, CH$_3$), 2.95 and 3.09(two dd, CH$_2$), 3.38(dd, H6), 3.30–3.66(m, SCH$_2$), 4.09(dt, H5), 4.26(p, CH$_3$C$\underline{H}$OH), 4.59(s, CH$_2$SO$_3$), 4.83(HOD), 8.09(d, pyridyl H5), 8.93(d, pyridyl H6), 8.97(s, pyridyl H2).

EXAMPLE 25

Sodium (5R,6S)-6-[1(R)-hydroxyethyl]-2-[2-(3-methyl-4-sulfonatomethyl-1-pyridinium)ethylthio]carbapen-2-em-3-carboxylate

EXAMPLE 26

Sodium (5R,6S)-2-[2-(3-ethyl-4-sulfonatomethyl-1-pyridinium)ethylthio]-6-[1(R)-hydroxyethyl]carbapen-2-em-3-carboxylate

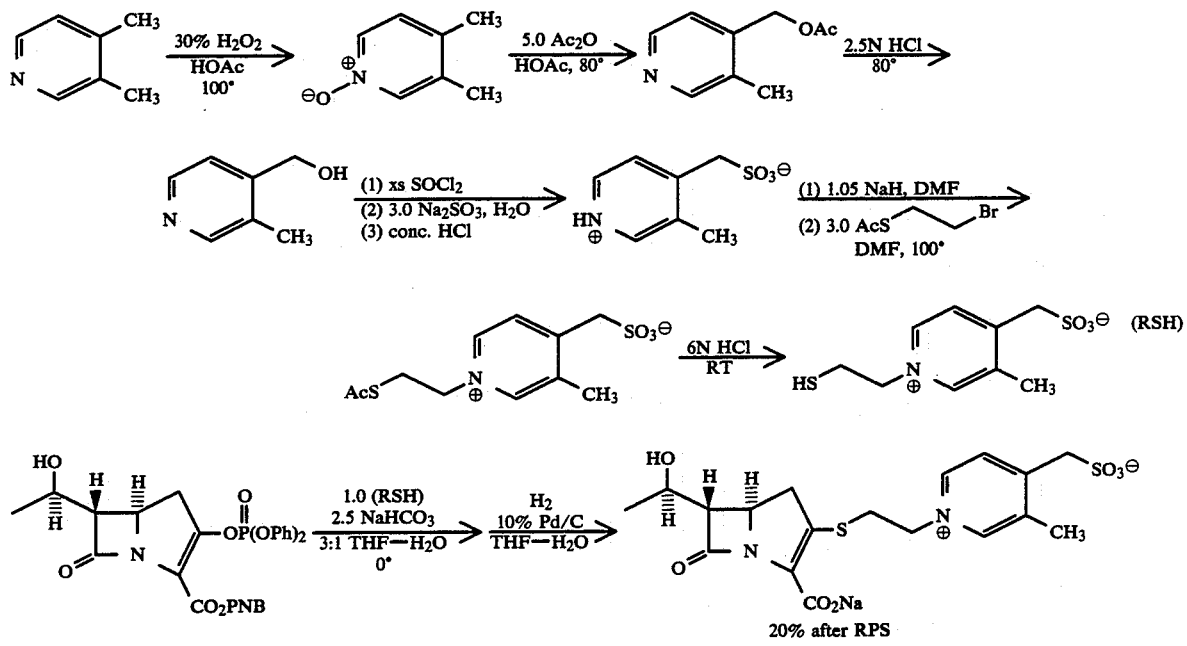

-continued

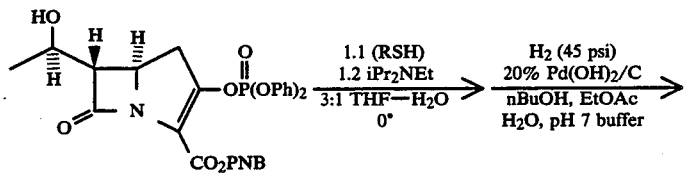

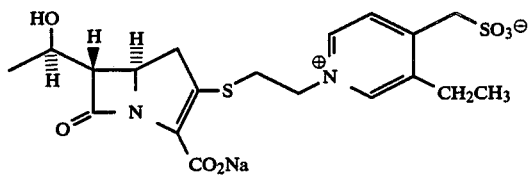

43% crude
38% after Dowex
28% after RPS-F

IR (Nujol) 3380(br), 1746, 1635, 1585, 1224, 1035 cm$^{-1}$.

UV (0.05M pH 7.0 MOPS) λ max 275 (ε 8420), 297 (ε 8060)nm.

UV (buffer+NH$_2$OH) λ max ext. 299 (ε ext. 6960) nm.

NMR (D$_2$O) δ 1.31(d, CH$_3$CH), 1.35(t, CH$_3$CH$_2$), 2.97(m, CH$_2$), 3.38(dd, H6), 3.4–3.67(m, SCH$_2$), 4.08(dt, H5), 4.25(p,CH$_3$CH), 4.61(s, CH$_2$SO$_3$), 4.83(HOD), 4.89(t, CH$_2$N), 8.13(d, pyridyl H5), 8.75(d, pyridyl H6), 8.78(s, pyridyl H2).

EXAMPLE 27

Sodium (5R,6S)-2-[2-(3-fluoro-4-sulfonatomethyl-1-pyridinium-)ethylthio]-6-[1(R)-hydroxyethyl]carbapen-2-em-3-carboxylate

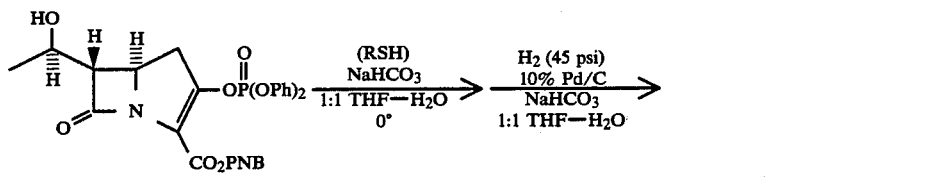

9% after XAD-2

UV (H$_2$O) λ max 232(ε 13120), 273(ε 9140), 295(ε 8280, 81% NH$_2$OH ext.) nm.

NMR (D$_2$O) δ 1.34(d, CH$_3$CHOH), 3.16(two dd, CH$_2$), 3.48(dd, H6), 3.3–3.7(m, SCH$_2$), 4.22(dt, H5), 4.3(p, CH$_3$CHOH), 4.64(s, CH$_2$SO$_3$), 4.96 (m, CH$_2$N), 8.3(t, pyridyl H5), 8.86(d, pyridyl H6), 9.16(d, pyridyl H2).

EXAMPLE 28
Sodium (1R,5S,6S)-2-[2-(3-fluoro-4-sulfonatomethyl-1-pyridinium)ethylthio]-6-[1(R)-hydroxyethyl]-1-methylcarbapen-2-em-3-carboxylate
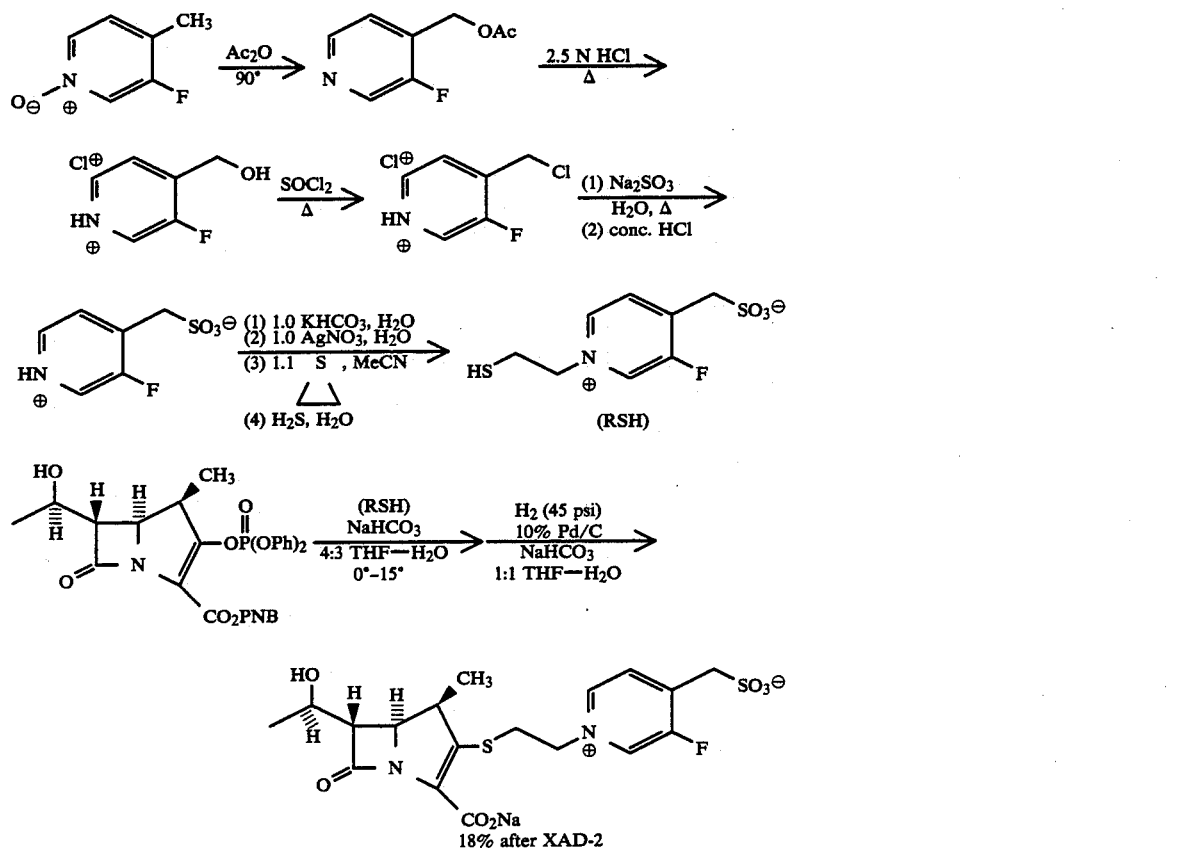
UV (H₂O) λ max 272(ε 7260), 293(ε 6470, 78% NH₂OH ext.) nm.
NMR (D₂O) ε 1.26(d, 1-CH₃), 1.39(d, CH₃CHOH), 3.3-3.7(m, SCH₂ and H1), 3.53(dd, H6), 4.18(dd, H5), 4.33(p, CH₃CHOH), 4.67(s, CH₂SO₃), 5.0(m, CH₂N), 8.33(t, pyridyl H5), 8.85(d, pyridyl H6), 9.16(d, pyridyl H2).
EXAMPLE 29
Sodium (1R,5S,6S)-2-[2-(3-chloro-4-sulfonatomethyl-1-pyridinium)ethylthio]-6-[1(R)-hydroxyethyl]-1-methylcarbapen-2-em-3-carboxylate
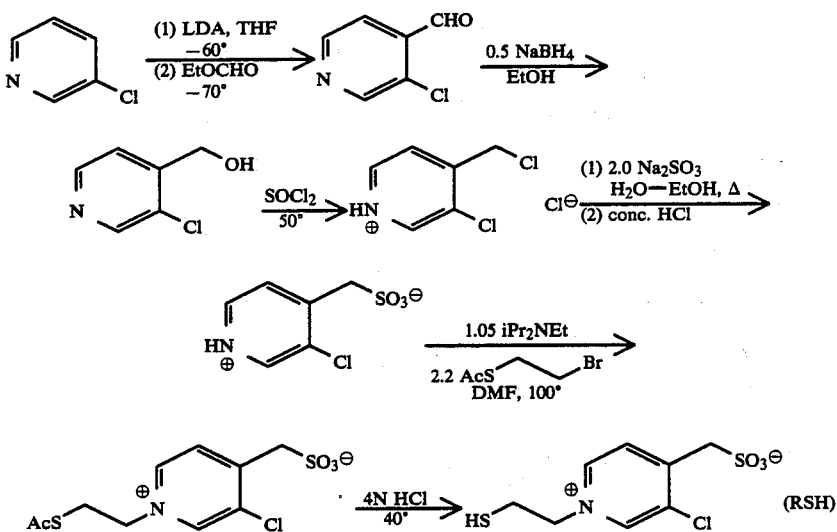

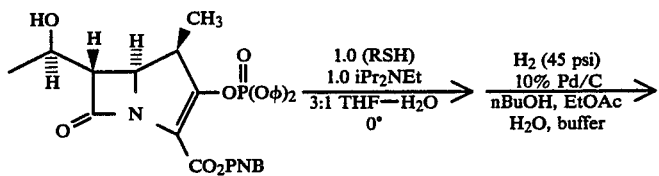

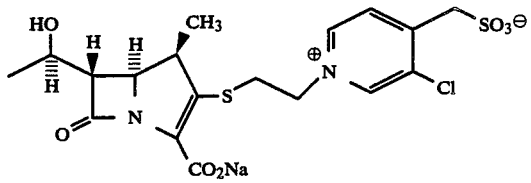

25% crude
22% after Dowex
19% after RPS

IR(Nujol) 3400(br), 1745, 1635, 1585, 1040 cm$^{-1}$.
UV (H$_2$O) λ max 241(ε 8170), 285(ε 8590)nm.
UV (H$_2$O+NH$_2$OH) λ max ext. 295(ε ext. 5830)nm.
NMR (D$_2$O) δ 1.15(d, CH$_3$CH), 1.28(d, CH$_3$CHOH), 3.25(dq, H1), 3.28 and 3.57(two td, SCH$_2$), 3.42(dd, H6), 4.03(dd, H5), 4.23(p, CH$_3$C$\underline{H}$OH), 4.68(s, CH$_2$SO$_3$), 4.7–4.9(m, CH$_2$N), 8.22(d, pyridyl H5), 8.81(d, pyridyl H6), 9.14(s, pyridyl H2).

EXAMPLE 30

Sodium (5R,6S)-2-[2-(3-bromo-4-sulfonatomethyl-1-pyridinium-)ethylthio]-6-[1(R)-hydroxyethyl]carbapen-2-em-3-carboxylate

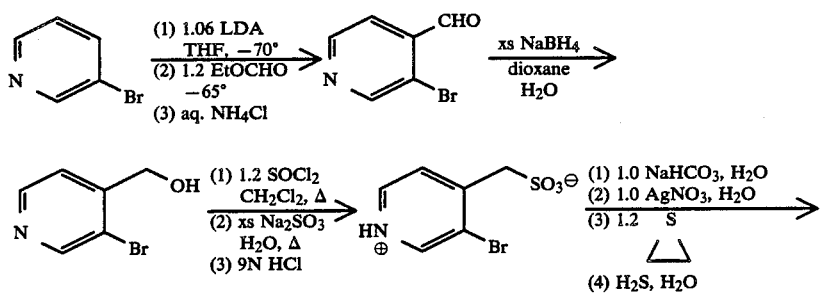

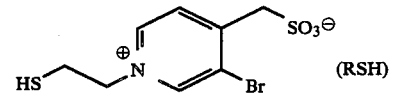

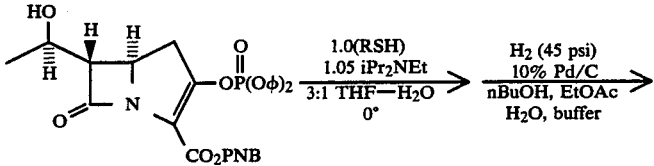

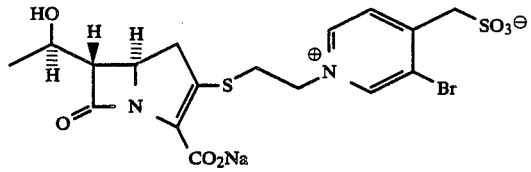

42% crude
41% after Dowex
29% after RPS

IR (Nujol) 3400 (br), 1745, 1630, 1585, 1235, 1195, 1038 cm$^{-1}$.
UV (H$_2$O) λ max 243(ε 7,270), 289(ε 9,430)nm.
UV (H$_2$O+NH$_2$OH) λ max ext. 295(ε ext 6,450)nm.

NMR (D₂O) δ 1.28(CH₃CH), 2.98 and 3.11(two dd, CH₂), 3.37(dd, H6), 3.36 and 3.55(two td, SCH₂), 4.11(dt, H5), 4.22(p, CH₃CH), 4.70(s, CH₂SO₃), 4.86–4.88(m, NCH₂), 8.21(d, pyridyl H5), 8.87(dd, pyridyl H6), 9.27(d, pyridyl H2).

EXAMPLE 31

Sodium (5R,6S)-2-[2-(3-amino-4-sulfonatomethyl-1-pyridinium-)ethylthio]-6-[1(R)-hydroxyethyl]carbapen-2-em-3-carboxylate UV (0.05M pH 7.0 MOPS buffer) λ max 257 (ε 7500), 300(ε 8970), 333(ε 3990)nm.

UV (buffer+NH₂OH) λ max ext. 297.5 nm (ε ext 7340).

NMR (D₂O) δ 1.30(d, CH₃CH), 2.90 and 3.02(two dd, CH₂), 3,34(dd, H6), 3.29–3.56(m, SCH₂), 4.07 (dt, H5), 4.23(p, CH₃CH), 4.44(s, CH₂SO₃), 4.72(t, CH₂N), 4.84(HOD), 7.77(d, pyridyl H5), 8.12(d, pyridyl H6), 8,25(s, pyridyl H2).

EXAMPLE 32

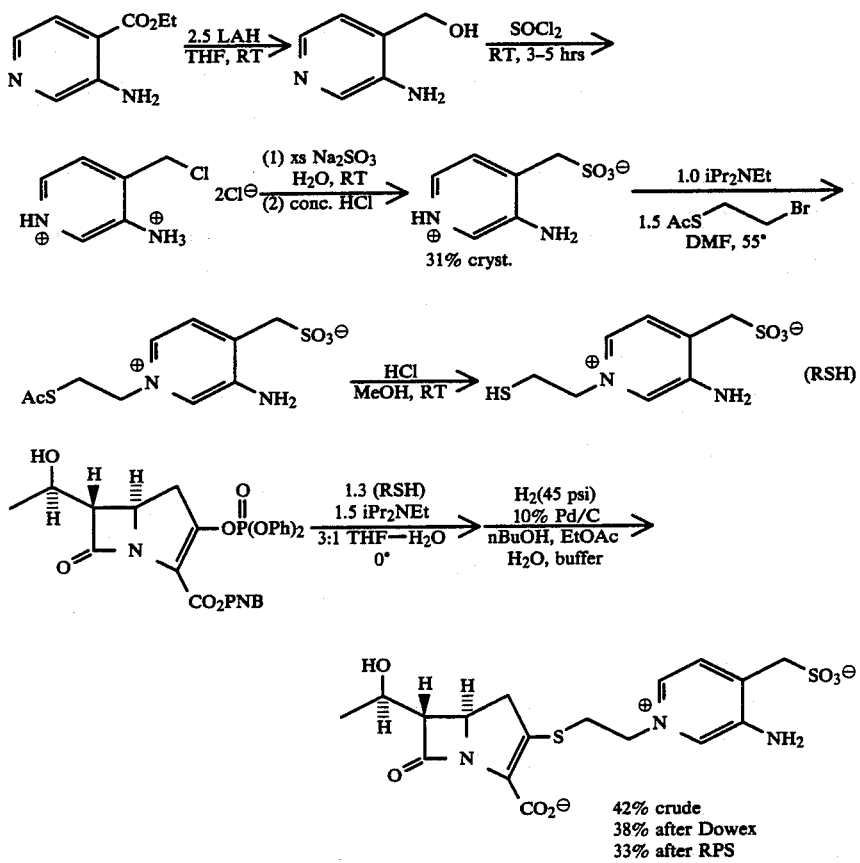

IR (nujol) 3350(br), 1742, 1640, 1580, 1520, 1225, 1180, 1030 cm⁻¹.

Sodium (5R,6S)-2-[2-(3-acetamido-4-sulfonatomethyl-1-pyridinium)ethylthio]-6-[1(R)-hydroxyethyl]carbapen-2-em-3-carboxylate

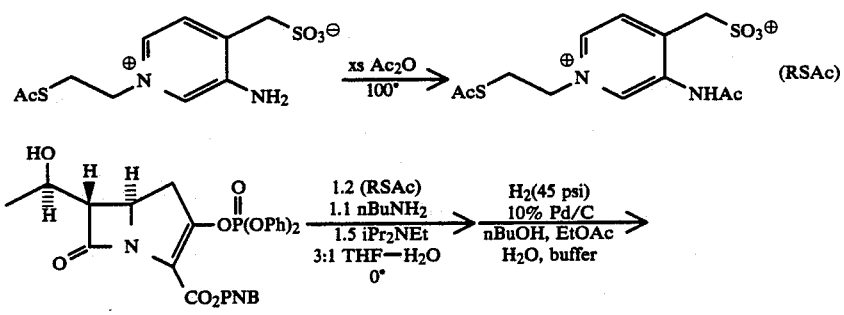

-continued

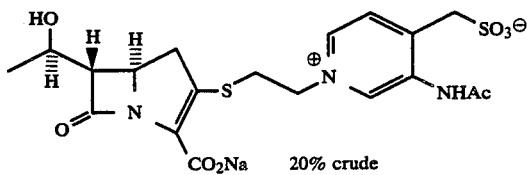

20% crude
16% after Dowex
14% after RPS

IR (nujol) 3380(br), 1745, 1690, 1630, 1585, 1225, 1035 cm$^{-1}$.

UV (0.05M pH 7.0 MOPS buffer) λ max 250 (ε 8190), 296(ε 9950)nm.

UV (buffer+NH$_2$OH) λ max ext 296.5 (ε ext 6300)nm.

NMR (D$_2$O) δ 1.29(d, CH$_3$CH), 2.35(s, COCH$_3$), 2.96 and 3.09(two dd's, CH$_2$), 3.35(dd, H6), 3.4–3.64(m, SCH$_2$), 4.03(dt, H5), 4.23(p, CH$_3$CH), 4.64(s, CH$_2$SO$_3$), 4.84(HOD), 4.91(t, CH$_2$N), 8.13(d, pyridyl H5), 8.72(d, pyridyl H6), 9.38(s, pyridyl H2).

EXAMPLE 33

Sodium (5R,6S)-6-[1(R)-hydroxyethyl]-2-[2-(3-methoxy-4-sulfonatomethyl-1-pyridinium)ethylthio]-carbapen-2-em-3-carboxylate UV (H$_2$O) λ max 294(ε 10570, 48% NH$_2$OH ext.) nm.

NMR (D$_2$O) δ 1.36(d, CH$_3$CHOH), 3.08(m, CH$_2$), 3.44(dd, H6), 3.3–3.7(m, SCH$_2$), 4.16(s, OCH$_3$), 4.3(m, H5 and CH$_3$CHOH), 4.62(s, CH$_2$SO$_3$), 4.95 (t, CH$_2$N), 8.14(d, pyridyl H5), 8.62(d, pyridyl H6), 8.66(s, pyridyl H2).

EXAMPLE 34

Sodium (5R,6S)-2-[2-(3-methylthio-4-sulfonatomethyl-1-pyridinium)ethylthio]-6-[1(R)-hydroxyethyl]carbapen-2-em-3-carboxylate

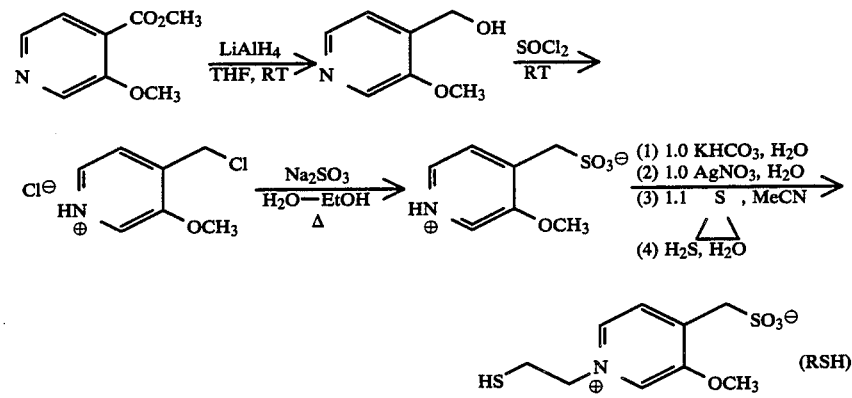

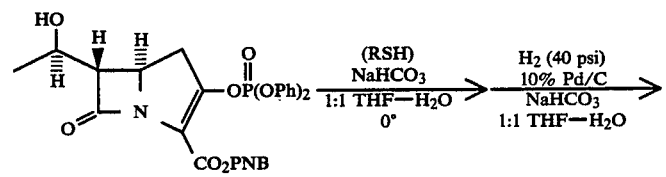

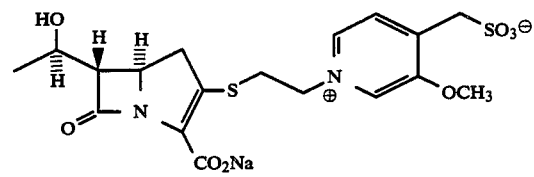

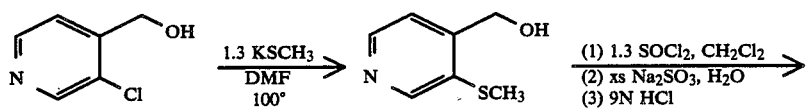

-continued

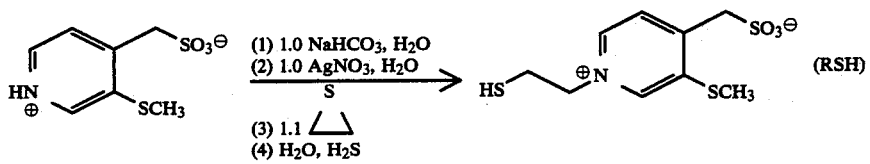

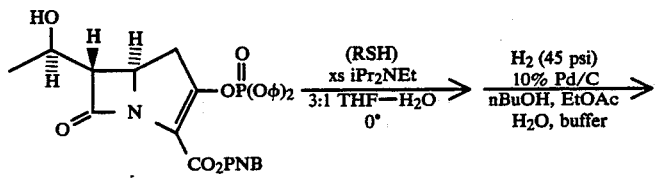

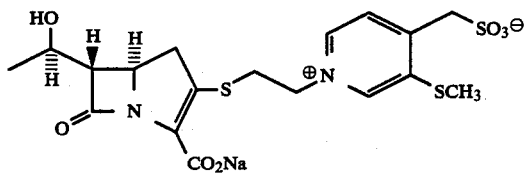

37% crude.
37% after Dowex
23% after RPS

IR (Nujol) 3400(br) 1740, 1590, 1230, 1190, 1035 cm$^{-1}$.

UV (H$_2$O) λ max 235(ε 10,700), 276(ε 7,480), 298(sh, ε 6,230)nm.

UV (H$_2$O+NH$_2$OH) δ max est. 299(ε ext. 5,050)nm.

NMR (D$_2$O) δ 1.28(d, CH$_3$CH), 2.66(s, SCH$_3$), 2.91 and 3.00 (two dd, CH$_2$), 3,32(dd, H6), 3.36 and 3.55(two td, SCH$_2$), 4.06(dt, H5), 4.20(p, CH$_3$C$\underline{H}$), 4.8–4.9(m, CH$_2$N), 8.03(d, pyridyl H5), 8.62(s, pyridyl H2), 8.63(d, pyridyl H6).

EXAMPLE 35

Sodium (5R,6S)-6-[1(R)-hydroxyethyl]-2-[2-(3-methoxycarbonyl-4-sulfonatomethyl-1-pyridinium)ethylthio]-carbapen-2-em-3-carboxylate

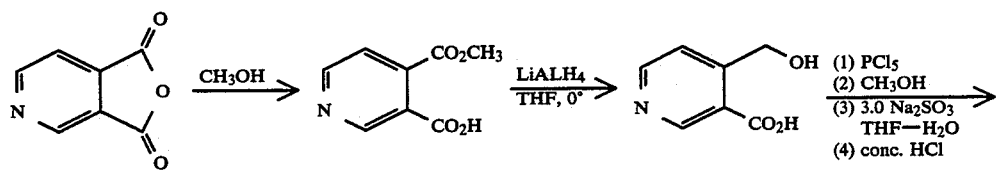

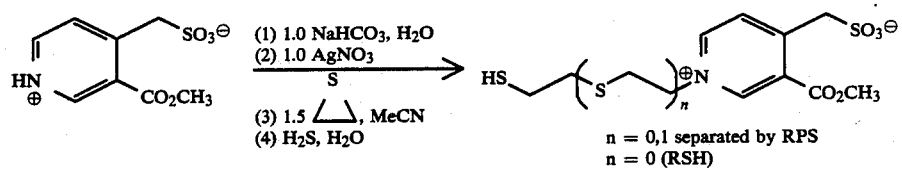

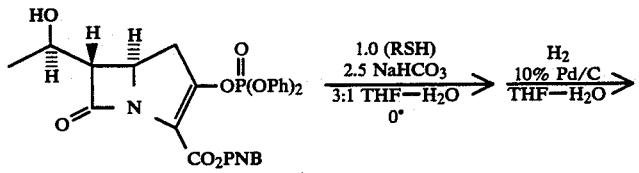

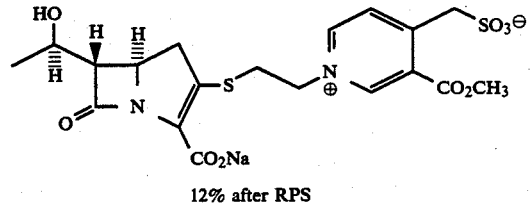

12% after RPS

UV ($H_2O$) λ max 268(ε 7350), 274(ε 7420), 295(ε 7270, 80% $NH_2OH$ ext.) nm.

NMR ($D_2O$) δ 1.31(d, C$\underline{H}_3$CHOH), 3.00 and 3.12(two dd, $CH_2$), 3.41(dd, H6), 3.36–3.70(m, $SCH_2$), 4.09(s, $CO_2CH_3$), 4.13(dt, H5), 4.25(p, $CH_3C\underline{H}OH$), 4.83(HOD), 4.98(m, $CH_2N$), 5.04(s, $CH_2SO_3$), 8.27(d, pyridyl H5), 9.04(d, pyridyl H6), 9.41 (s, pyridyl H2).

UV ($H_2O$) λ max 268(ε 6700), 274(ε 6700), 300(ε 8200, 82% $NH_2OH$ ext. nm.

NMR ($D_2O$) δ 1.35(d, C$\underline{H}_3$CHOH), 2.90–3.36(m, $SC\underline{H}_2C\underline{H}_2SC\underline{H}_2$), 3.10(m, C$\underline{H}_2$), 3,47(dd, H6), 4.11(s, $CO_2CH_3$), 4.28(m, H5 and $CH_3C\underline{H}OH$), 4.83(HOD), 4.95(t, $CH_2N$), 5.05(s, $CH_2SO_3$), 8.27(d, pyridyl H5), 9.04(d, pyridyl H6), 9.41(s, pyridyl H2).

EXAMPLE 36

Sodium (5R,6S)-6-[1(R)-hydroxyethyl]-2-[[5-(3-methoxycarbonyl-4-sulfonatomethyl-1-pyridinium)-3-thia-1-pentyl]-thio]carbapen-2-em-3-carboxylate

EXAMPLE 37

Sodium (5R,6S)-2-[2-(3-carbamoyl-4-sulfonatomethyl-1-pyridinium)ethylthio]-6-[1(R)-hydroxyethyl]carbapen-2-em-3-carboxylate

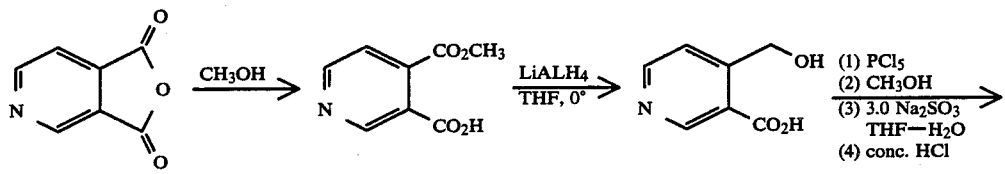

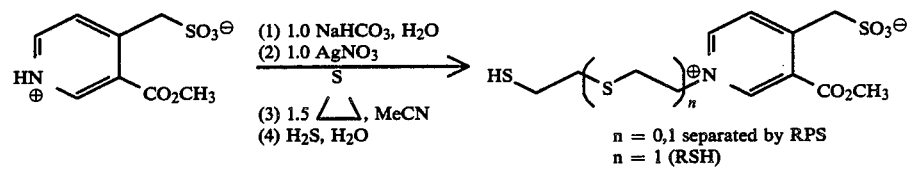

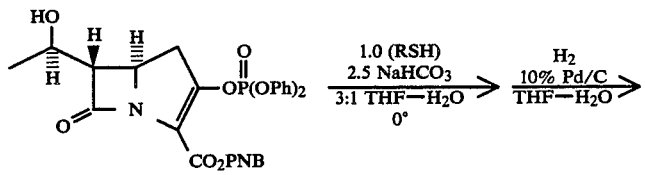

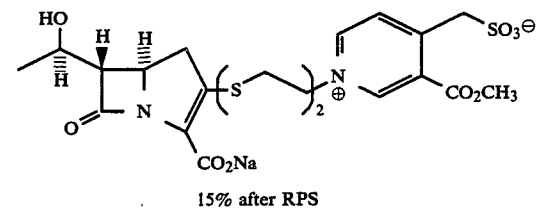

15% after RPS

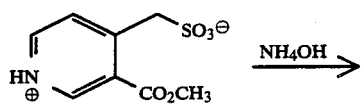

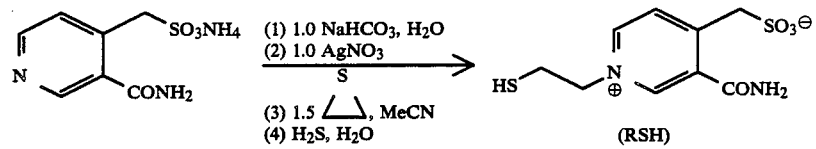

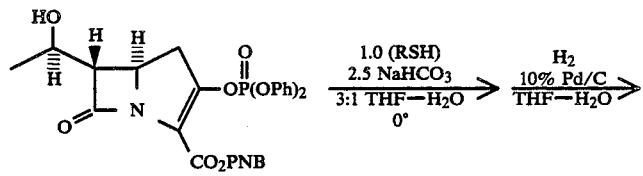

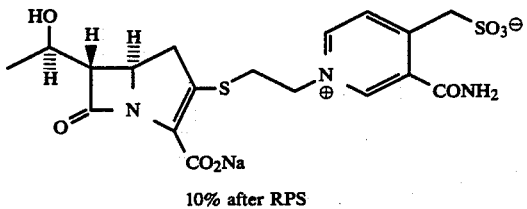

10% after RPS

UV (H$_2$O) λ max 268(ε 8000), 274(ε 8070), 295(ε 8500)nm.
UV (H$_2$O+NH$_2$OH) λ max ext. 300(ε ext. 7100) nm.
NMR (D$_2$O) δ 1.32(d, CH$_3$CHOH), 3.06 and 3.21(two dd, CH$_2$), 3.45(dd, H6), 3.38–3.70(m, SCH$_2$), 4.19(dt, H5), 4.25(p, CH$_3$CHOH), 4,81(HOD), 4.96(m, CH$_2$N), 8.27(d, pyridyl H5), 8.99(d, pyridyl H6), 9.21(s, pyridyl H2).

IR (Nujol) 3400 (br), 1745, 1635, 1585, 1230, 1040 cm$^{-1}$.
UV (H$_2$O) λ max 239 (ε 5,150), 270(ε 4,400), 296(ε 4,350)nm.
UV (H$_2$O+NH$_2$OH) λ max ext. 297(ε ext. 3,580)nm.
NMR (D$_2$O) δ 1.28(d, CH$_3$CH), 3.01 and 3.12(two dd, CH$_2$), 3.3–3.4(m, SCH$_a$H$_b$), 3.40(dd, H6), 3.60(td, SCH$_a$H$_b$), 4.13(dt, H5), 4.22(p, CH$_3$CH), 4.9–5.0 (m, CH$_2$N), 4.9(s, CH$_2$SO$_3$), 8.40(d, pyridyl H5), 9.06(d, pyridyl H6), 9.43(s, pyridyl H2).

EXAMPLE 38

Sodium (5R,6S)-2-[2-(3-aminosulfonyl-4-sulfonatomethyl-1-pyridinium)ethylthio]-6-[1(R)-hydroxyethyl]carbapen-2-em-3-carboxylate

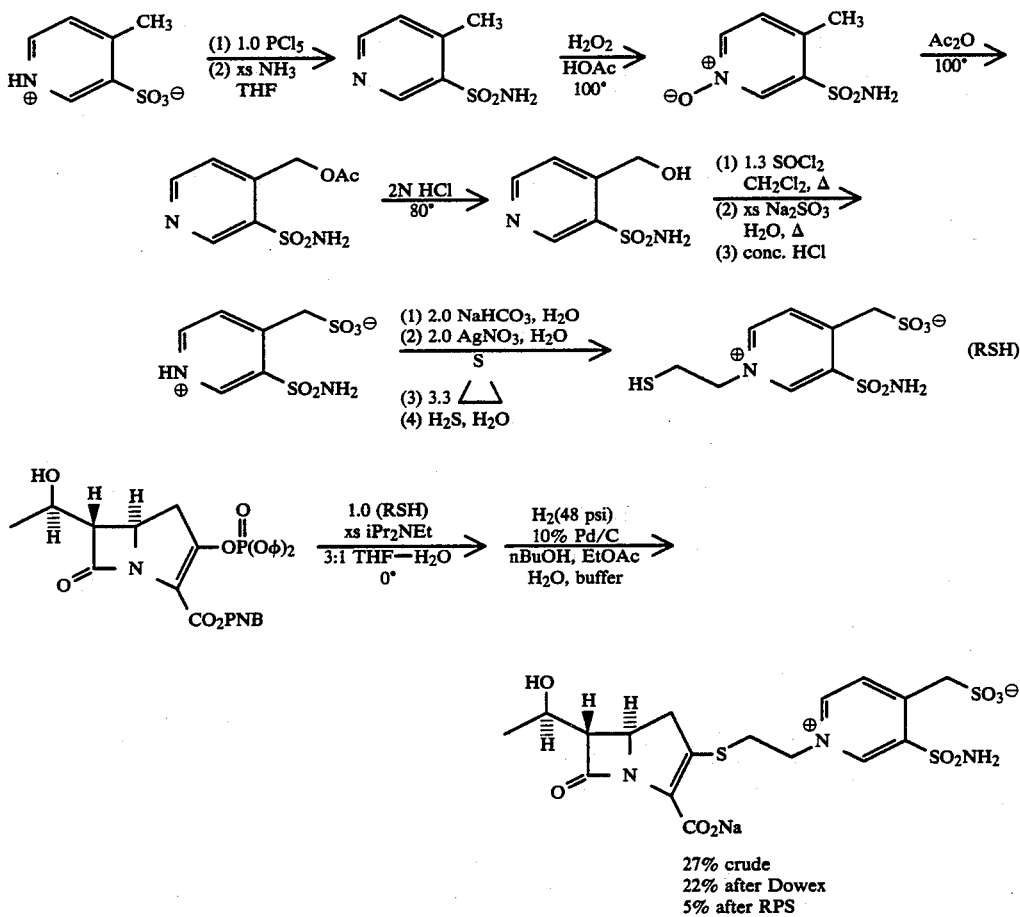

27% crude
22% after Dowex
5% after RPS

EXAMPLE 39

Sodium (5R,6S)-2-[2-[3-(N-methyl)aminosulfonyl-4-sulfonatomethyl-1-pyridinium]ethylthio]-6-[1(R)-hydroxyethyl]carbapen-2-em-3-carboxylate

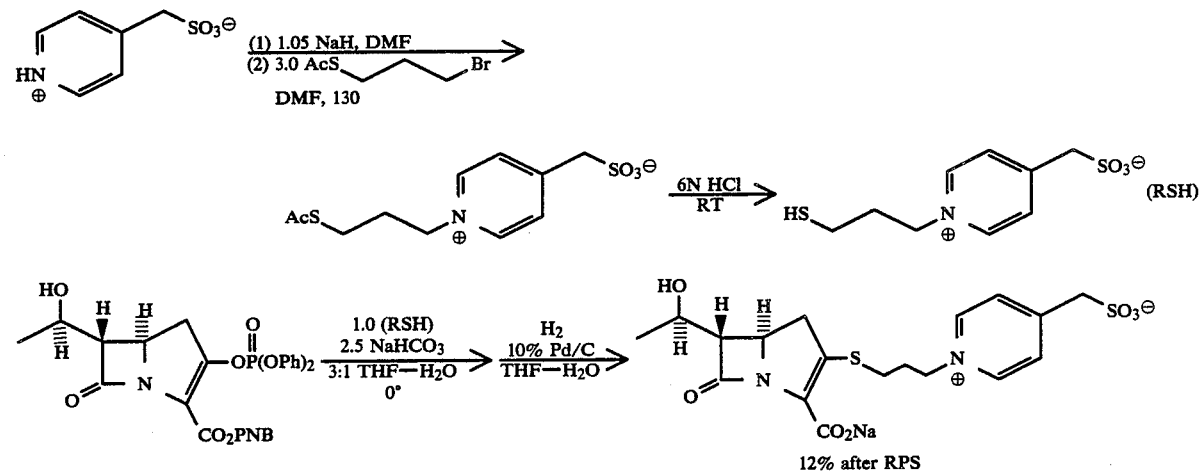

IR (Nujol) 3420 (br), 1745, 1635, 1585, 1228, 1155, 1038 cm$^{-1}$.

UV(H$_2$O) λ max 291 (ε 7,200)nm.

UV (H$_2$O+NH$_2$OH) λ max ext. 294(ε ext. 6,040)nm.

NMR (D$_2$O) δ 1.28(d, CH$_3$CH), 2.68(s, NCH$_3$), 3.01 and 3.12(two dd, CH$_2$), 3.40(dd, H6), 3.41 and 3.59(two td, SCH$_2$), 4.15(dt, H5), 4.22(p, H8), 4.9–5.1(m, CH$_2$N), 8.45(d, pyridyl H5), 9.10(d, pyridyl H6), 9.48(s, pyridyl H2).

EXAMPLE 40

Sodium (5R,6S)-6-[1(R)-hydroxyethyl]-2-[3-(4-sulfonatomethyl-1-pyridinium)propylthio]carbapen-2-em-3-carboxylate

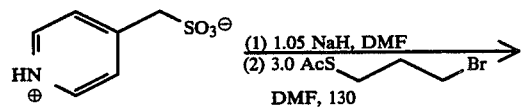

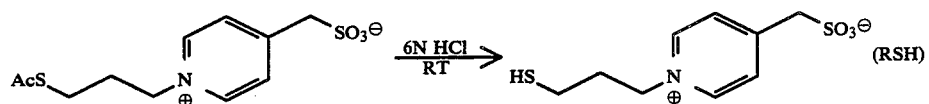

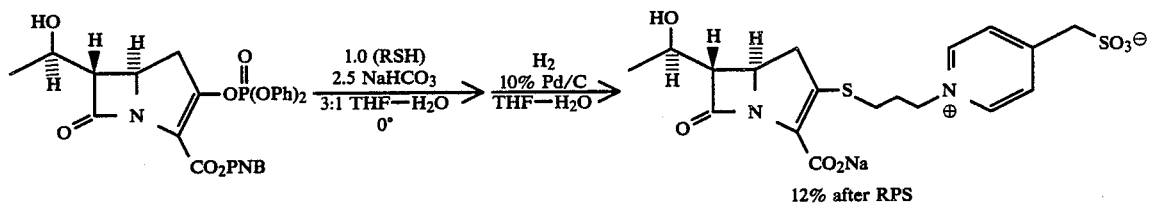

12% after RPS

UV (H$_2$O) λ max 254(ε 6,200), 266(ε 6100), 297 (ε 6850)nm.

UV (H$_2$O+NH$_2$OH) λ max ext. 298(ε 6370) nm.

NMR (D$_2$O) δ 1.33(D, CH$_3$CHOH), 2.41(m, SCH$_2$CH$_2$CH$_2$), 2.78–3.06(m, SCH$_2$), 3.11 and 3.30(two dd, CH$_2$), 3.44(dd, H6), 4.25(m, H5 and CH$_3$CHOH), 4.76(s, CH$_2$SO$_3$), 8.14(d, pyridyl H3,H5), 8.91 (d, pyridyl H2,H6).

EXAMPLE 41

Sodium
(5R,6S)-6-[1(R)-hydroxyethyl]-2-[2-(4-sulfonatomethyl-1-quinolinium)ethylthio]carbapen-2-em-3-carboxylate IR (Nujol) 3400(br), 1740, 1722, 1640, 1583, 1180, 1135, 1110 cm$^{-1}$.

UV (0.05M pH 7.0 MOPS buffer) λ max 265(ε 3830), 275(ε 3830), 278(ε 7110), 286(ε 7180), 293(ε 4810), 339(ε 3350)nm.

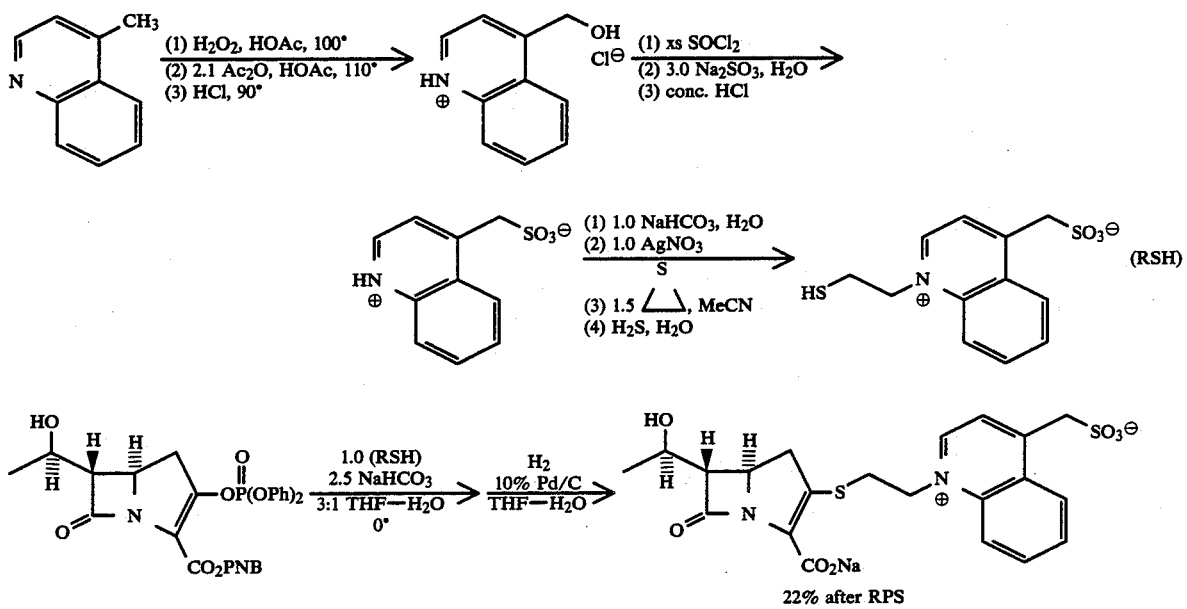

UV (H$_2$O) λ max 302(ε 8230), 320(ε 6220) nm.
UV (H$_2$O+NH$_2$OH) λ max ext. 295 (ε ext. 4950) nm.
nmr (D$_2$O) δ 1.23(d, CH$_3$CHOH), 2.55(m, CH$_2$), 3.02(dd, H6), 3.49(dt, H5), 3.50–3.80(m, SCH$_2$), 4.16(p, CH$_3$CHOH), 5.11(ABq, CH$_2$SO$_3$), 5.38(m, CH$_2$N), 8.12(d, quinolyl H3), 8.19 and 8.37(two dd, quinolyl H6,H7), 8.60 and 8.77(two d, quinolyl H5, H8), 9.28(d, quinolyl H2).

UV (buffer+NH$_2$OH) λ max ext. 293(ε ext. 4810)nm.
NMR (D$_2$O) δ 1.05(d, 1-CH$_3$), 1.22(d, CH$_3$CHOH), 2.98(dq, H1), 3.26(dd, H6), 3.34–3.74(m, SCH$_2$ and H5), 4.1(p, CH$_3$CHOH), 4.84(HOD), 4.94–5.28(m, CH$_2$N), 8.12(t, isoquinolyl H7), 8.54(d, isoquinolyl H8), 8.76(two overlapping d, isoquinolyl H4 and H6), 9.08(d, isoquinolyl H3), 9.84(s, isoquinolyl H1).

EXAMPLE 42

Sodium
(1R,5S,6S)-6-[1(R)-hydroxyethyl]-2-[2-(5-sulfonato-2-isoquinolinium)ethylthio]-1-methylcarbapen-2-em-3-carboxylate

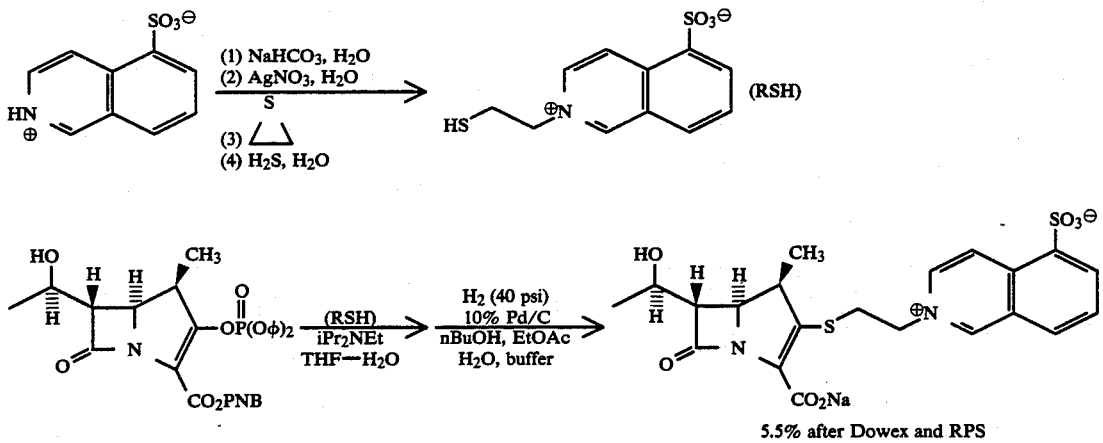

EXAMPLE 43

Sodium (1R,5S,6S)-6-[1(R)-hydroxyethyl]-2-[2-(3-sulfonatomethyl-1-pyridazinium])ethylthio)-1-methylcarbapen-2-em-3-carboxylate

EXAMPLE 44

Sodium (1R,5S,6S)-6-[1(R)-hydroxyethyl]-2-[2-(4-sulfonatomethyl-1-pyridazinium)ethylthio]-1-methylcarbapen-2-em-3-carboxylate (isomer A) and sodium

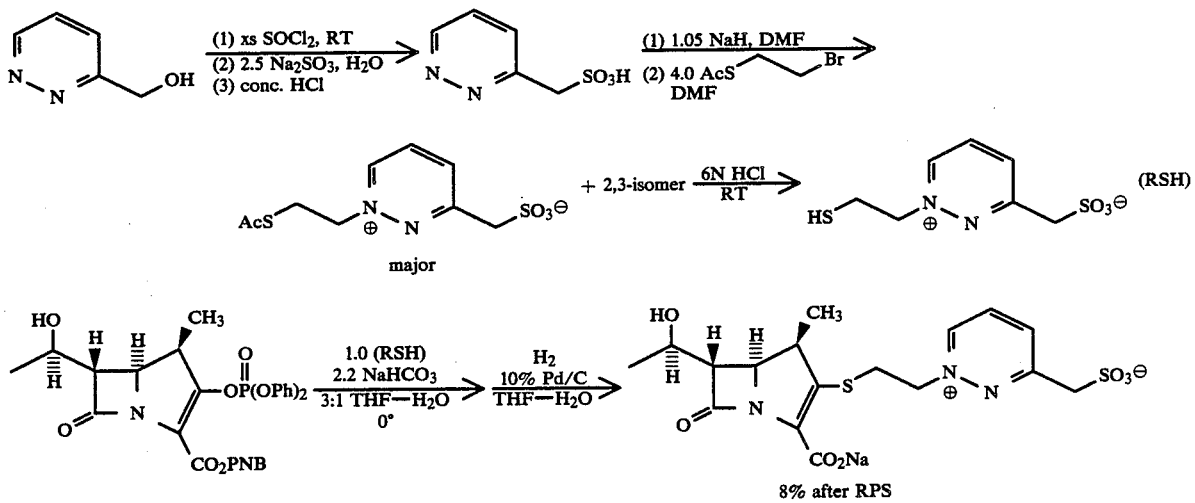

UV (H$_2$O) λ max 294(ε 6150, 85% NH$_2$OH ext.) nm.
NMR (D$_2$O) δ 1.16(d, 1-CH$_3$), 1.30(d, CH$_3$CHOH), 3.32(m, H1), 3.48(dd, H6), 3.35–3.70(m, SCH$_2$), 4.10(dd, (1R,5S,6S)-6-[1(R)hydroxy-ethyl]-2-[2-(5-sulfonatomethyl-1-pyridazinium)ethylthio]-1-methylcarbapen-2-em-3-carboxylate (isomer B)

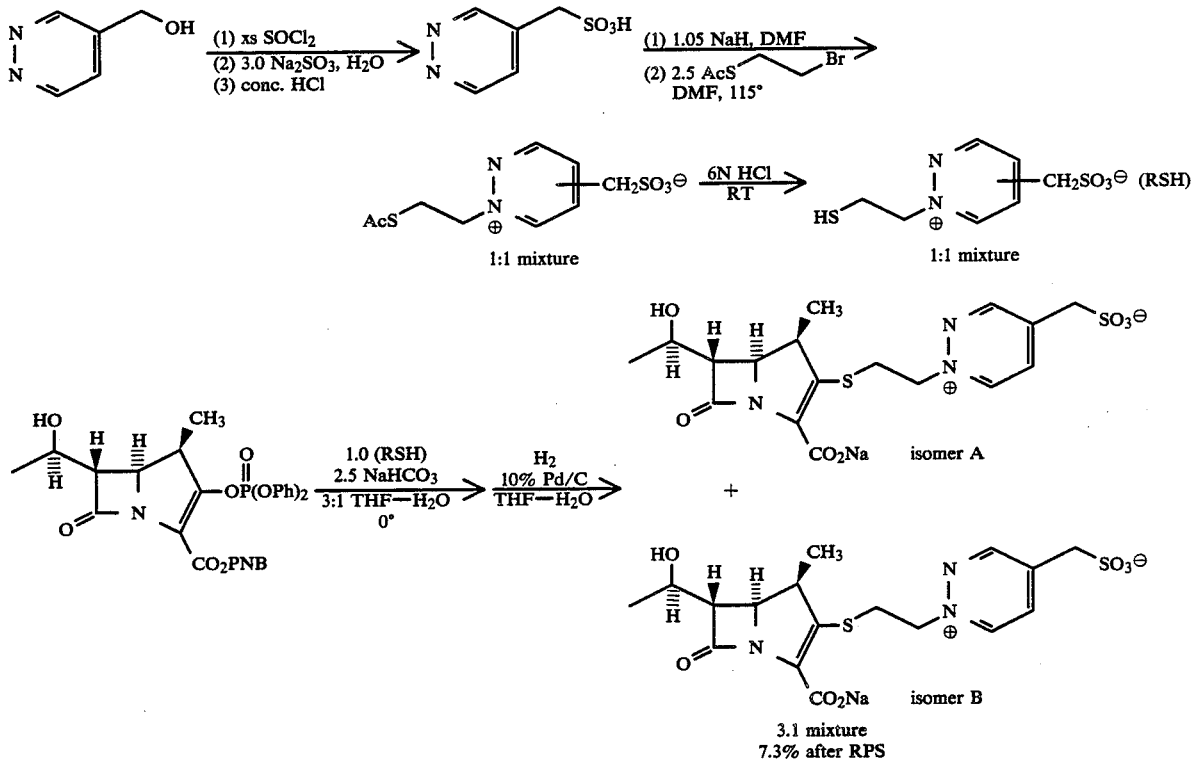

H5), 4.22(p, CH$_3$CHOH), 4.70(s, CH$_2$SO$_3$), 4.75(HOD), 5.12(t, CH$_2$N), 9.08(dd, pyridazinyl H5), 9.18(d, pyridazinyl H4), 9.67(d, pyridazinyl H6).

UV (H$_2$O) λ max 242(ε 9500), 293(ε 7500, 77% NH$_2$OH ext.) nm.
NMR (D$_2$O) Isomer A γ 1.21(d, 1-CH$_3$), 1.32(d, CH$_3$CHOH), 3.42(m, H1), 3.40–3.78(m, SCH$_2$), 3.48(dd, H6), 4.18(dd, H5), 4.28(p, CH$_3$CHOH), 4.64(s, CH2SO3), 4.85(HOD), 5.13(m, CH2N), 8.64(dd, pyridazinyl H5), 9.60(d, pyridazinyl H3), 9.64(d, pyridazinyl H6).

NMR(D2O) Isomer B δ 4.17(dd, H5), 4.57(s, CH2SO3), 8.64(dd, pyridazinyl H4), 9.57 (d, pyridazinyl H3), 9.82(s, pyridazinyl H6).

EXAMPLE 46

Sodium (1R,5S,6S)-6-[1(R)-hydroxyethyl]-2-[2-(3-methyl-4-sulfonatomethyl-1-imidazolium)ethylthio]-1-methylcarbapen-2-em-3-carboxylate

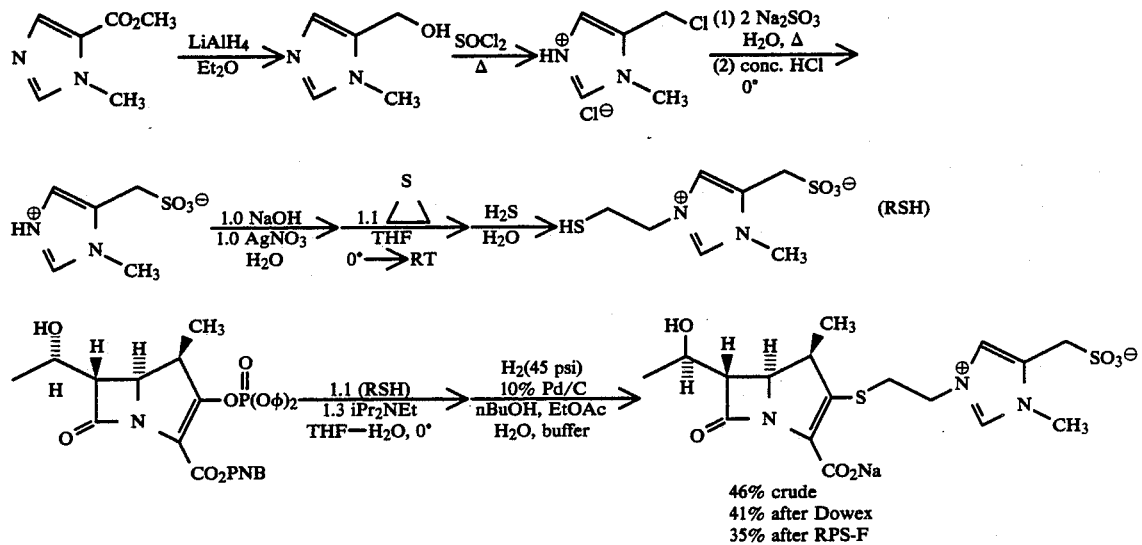

46% crude
41% after Dowex
35% after RPS-F

IR (Nujol) 3430(br), 1740, 1590, 1228, 1043 cm$^{-1}$.

UV (0.05pH 7.0 MOPS buffer) λ max 297.5 (97% NH2OH ext., ε ext. 7240) nm.

NMR (D2O) δ 1.15(d, CH3CH), 1.29(d, CH3CHOH), 3.12 and 3.39( two m's, SCH2), 3.28(m, H1̄), 3.43(dd,

EXAMPLE 45

Sodium (5R,6S)-6-[1(R)-hydroxyethyl]-2-[2-4-sulfonatomethyl-1-pyrimidinum)ethylthio]carbapen-2-em-3-carboxylate

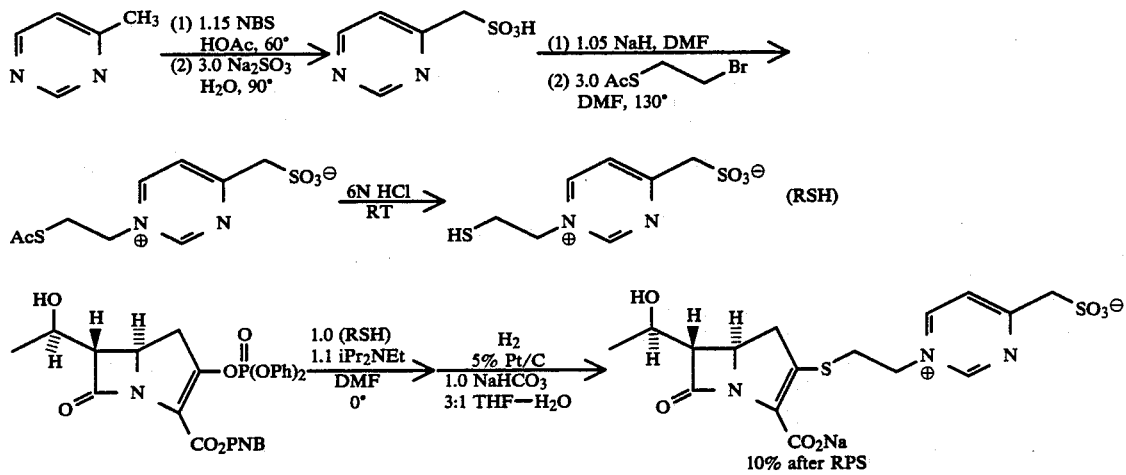

10% after RPS

UV (H2O) λ max 253(ε 7520), 295(ε 6630, 77% NH2OH ext.) nm.

NMR (D2O) δ 1.32(d, CH3CHOH), 3.12 and 3.28 (two dd, CH2), 3.30-3.70(m, SCH2), 3.48(dd, H6), 4.26(m, H5 and CH3CHOH), 4.44(s, CH2SO3), 4.83(HOD), 4.94(m, CH2N̄), 8.37(d, pyrimidyl H5), 9.28(d, pyrimidyl H6), 9.69(s, pyrimidyl H2).

H6), 3.91(s, NCH3), 4.08(dd, H5), 4.23(p, CH3CHOH), 4.39(s, CH2SO3), 4.47(m, CH2N), 4.80(HOD), 7.65(d, imidazolyl H5), 8.79(d, imidazolyl H2).

EXAMPLE 47

Sodium (1R,5S,6S)-6-[1(R)-hydroxyethyl]-2-[2-(3-(2-sulfonatoethyl)-1-imidazolium)ethylthio]-1-methylcarbapen-2-em-3-carboxylate

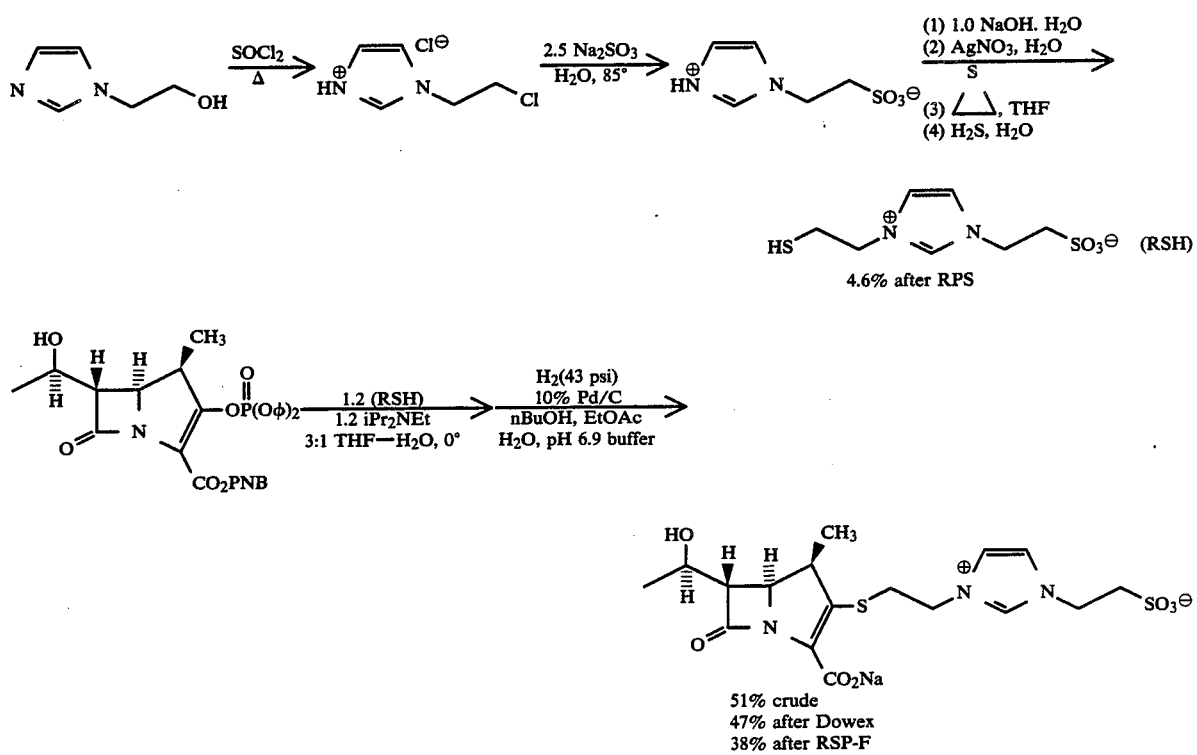

IR (Nujol) 3420(br), 1743, 1580, 1408, 1184, 1043 cm$^{-1}$.

UV (0.05M pH 7.0 MOPS buffer) λ max 297.5 (97% NH$_2$OH ext., ε ext 7310)nm.

NMR (D$_2$O) δ 1.22(d, CH$_3$CH), 1.35(d, CH$_3$CHOH), 3.20 and 3.46(two m's, SCH$_2$), 3.37(m, CH$_3$CH), 3.50(dd, H6), 3.51(t, CH$_2$SO$_3$), 4.15(dd, H5), 4.31(p, CH$_3$CHOH), 4.55 and 4.70(two t's, two CH$_2$N), 4.87(HOD), 7.63 and 7.71(two t's, imidazolyl H4, H5), 8.98(t, imidazolyl H2),

EXAMPLE 48

Sodium (1R,5S,6S)-6-[1(R)-hydroxyethyl]-2-[2-(2-sulfonatomethyl-3-thiazolium)ethylthio]-1-methylcarbapen-2-em-3-carboxylate

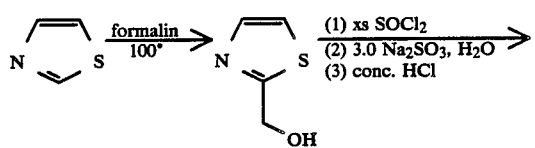

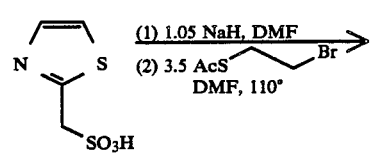

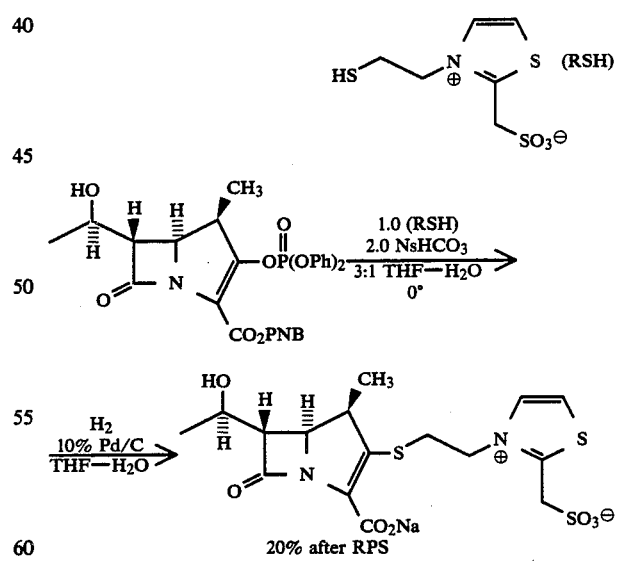

UV (H$_2$O) λ max 254(ε 8200), 294(ε 7000, 87% NH$_2$OH ext.) nm.

NMR (D$_2$O) δ 1.17(d, 1-CH$_3$), 1.30(d, CH$_3$CHOH), 3.30(m, H1), 3.30–3.62(m, SCH$_2$), 3.46(dd, H6), 4.06(dd, H5), 4.26(p, CH$_3$CHOH), 4.82(HOD), 4.93 (t, CH$_2$N), 5.06(ADq, CH$_2$SO$_3$), 8.25(d, thiazolyl H5), 8.29(d, thiazolyl H4).

EXAMPLE 49

Sodium (1R,5S,6S)-6-[1(R)-hydroxyethyl]-2-[2-(5-sulfonatomethyl-3-thiazolium)ethylthio]-1-methylcarbapen-2-em-3-carboxylate

EXAMPLE 50

Sodium (1R,5S,6S)-6-[1(R)-hydroxymethyl]-2-[2-[4-(N-methyl)-sulfonatoaminomethyl)-1-pyridinium]ethylthio]-1-methylcarbapen-2-em-3-carboxylate

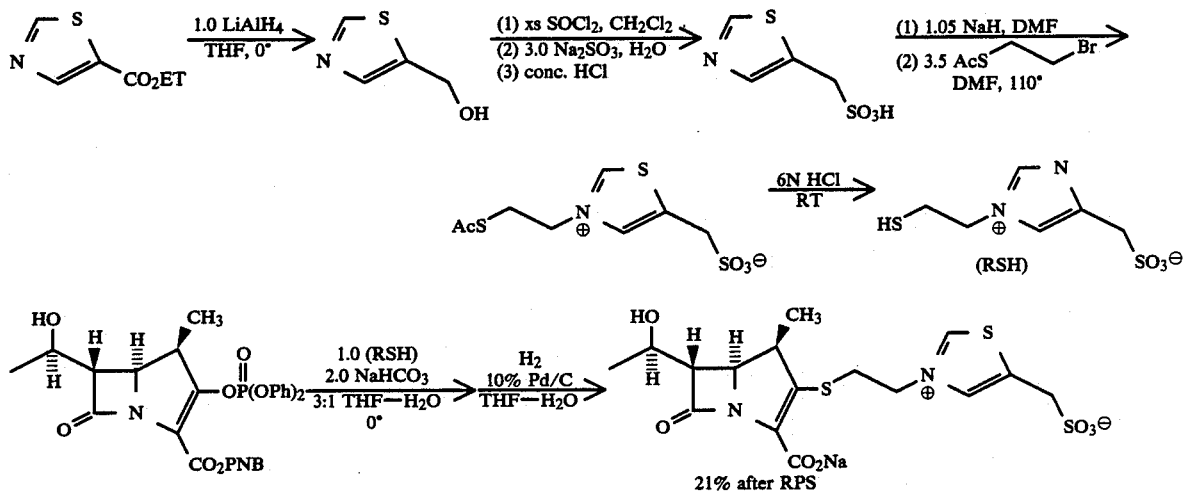

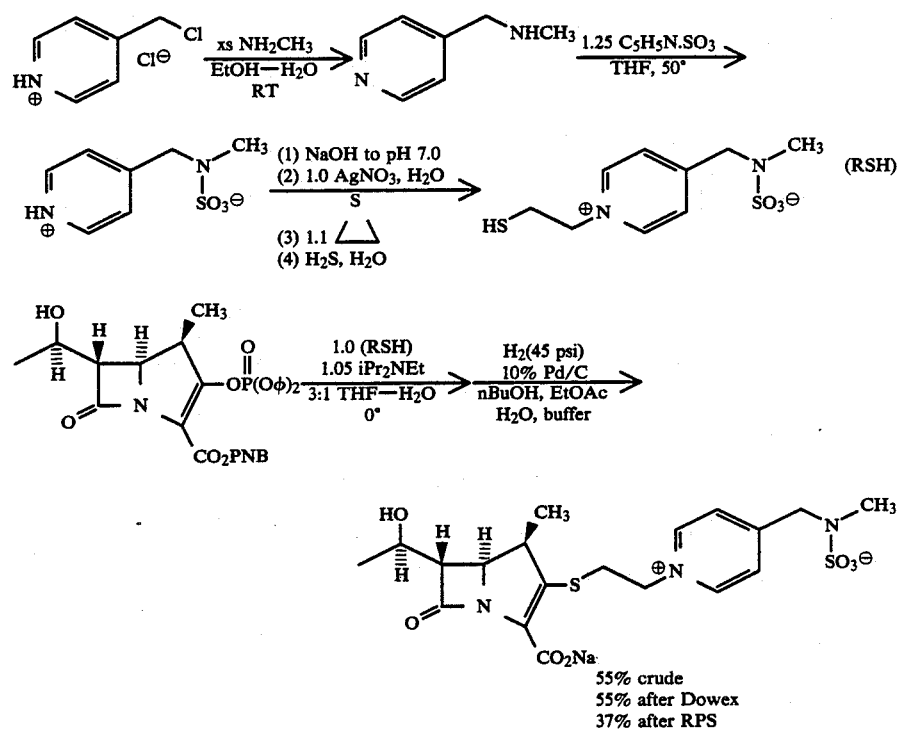

55% crude
55% after Dowex
37% after RPS

UV (H$_2$O) λ max 248(ε 7800), 294(ε 8300), 86% NH$_2$OH ext.) nm.

NMR (D$_2$O) δ 1.22(d, 1-CH$_3$), 1.35(d, CH$_3$CHOH), 3.30(m, H1), 3.30–3.64(m, SCH$_2$), 3.51(dd, H6), 4.16(dd, H5), 4.31(p, CH$_3$CHOH), 4.66(s, CH$_2$SO$_3$), 4.85(HOD), 8.47(s, thiazolyl H4).

IR (Nujol) 3400(br), 1740, 1640, 1590, 1240, 1180, 1035 cm$^{-1}$.

UV (H$_2$O) λ max 220(ε 9730), 257(ε 5750), 296(ε 7420)nm.

UV (H$_2$O+NH$_2$OH) ε max. ext. 297(ε ext. 6670) nm.

NMR (D$_2$O) δ 1.13(d, 1-CH$_3$), 1.27(d, CH$_3$CHOH), 2.77(s, NCH$_3$), 3.20(qd, H1), 3.29(td, SCH$_a$H$_b$), 3.40(dd, H6), 3.54(ddd, SCH$_a$H$_b$), 3.93(dd, H5), 4.21(p, CH$_3$CHOH), 4.46(s, pyridyl-CH$_2$), 4.7–4.9 (m, CH$_2$N), 8.07(d, pyridyl H3,H5), 8.77(d, pyridyl H2,H6).

EXAMPLE 51

Sodium (1R,5S,6S)-6-[1(R)-hydroxyethyl]-2-[2-(4-sulfonatomethylamino-1-pyridinium)ethylthio]-1-methylcarbapen-2-em-3-carboxylate

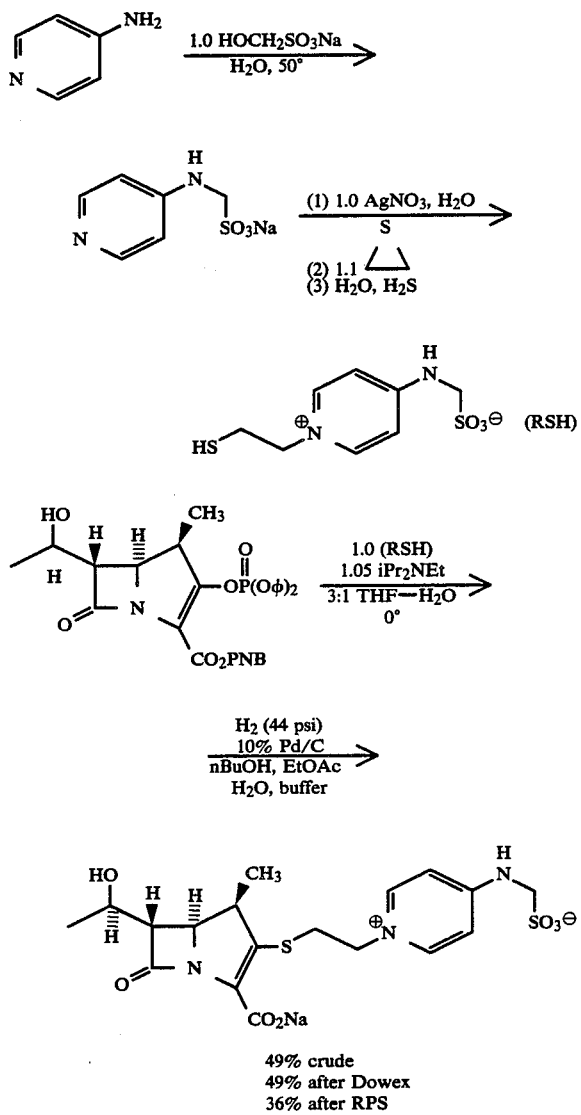

49% crude
49% after Dowex
36% after RPS

IR (Nujol) 3350(br), 1748, 1648, 1590, 1855, 1180, 1035 cm$^{-1}$.

UV (H$_2$O) λ max 213(ε 9420), 283(ε 20000)nm.

UV (H$_2$O+NH$_2$OH) λ max. ext. 304(ε ext. 7220)nm.

NMR (D$_2$O) λ 1.11(d, 1-CH$_3$), 1.28(d, CH$_3$CHOH), 3.10(qd, H1), 3.17(td, SCH$_a$Hb), 3.38(dd, H6), 3.41(ddd, SCHaH$_b$), 3.89(dd, H5), 4.22(p, CH$_3$CHOH), 4.33(ddd, NCH$_a$Hb), 4.56(td, NCHaH$_b$), 4.62 and 4.63 (two d, CH$_2$SO$_3$), 7.0–7.2(m, pyridyl H3,H5), 8.0–8.2(m, pyridyl H2,H6).

EXAMPLE 52

Sodium (1R,5S,6S)-6-[1(R)-hydroxyethyl]-2-[2-[4-(N-sulfonatocarbamoyl)-1-pyridium]ethylthio]-1-methylcarbapen-2-em-3-carboxylate

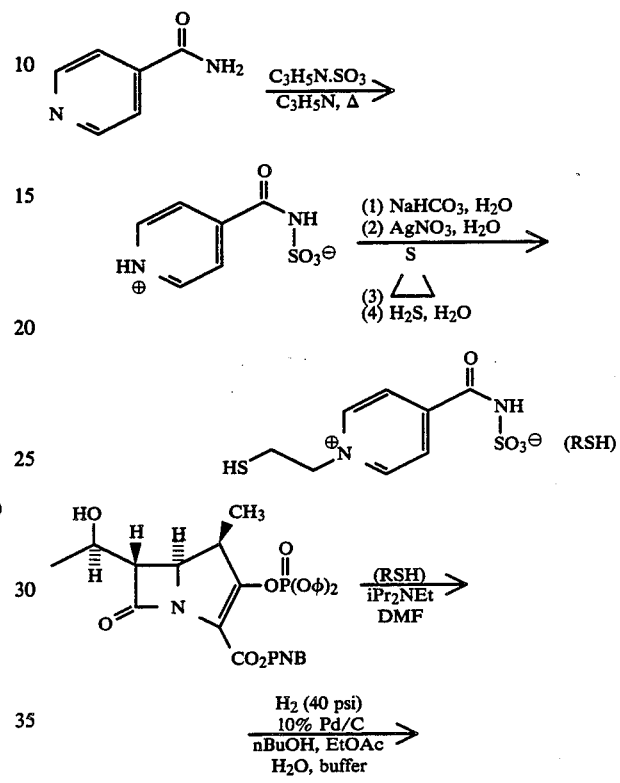

12.6% after Dowex and RPS

IR (Nujol) 3400(br), 1748, 1680, 1588, 1040 cm$^{-1}$.
UV (H$_2$O+NH$_2$OH) λ max. ext. 295 nm.
NMR (D$_2$O) δ 1.18(d, 1-CH$_3$), 1.31(d, CH$_3$CHOH), 3.2–3.42(m, SCHaH$_b$ and H1), 3.47(dd, H6), 3.62(dt, SCH$_a$Hb), 4.06(dd, H5), 4.26(p, CH$_3$CHOH), 4.82(HOD), 4.95(m, CH$_2$N), 8.39(d, pyridyl H3 and H5), 9.0(d, pyridyl H2 and H6).

EXAMPLE 53

Sodium (1R5S,6S)-2-[2-[4-[(ethoxy)oxidophosphinyl]-1-pyridinium]ethylthio]-6-[1(R)-hydroxyethyl]-1-methyl-carbapen-2-em-3-carboxylate

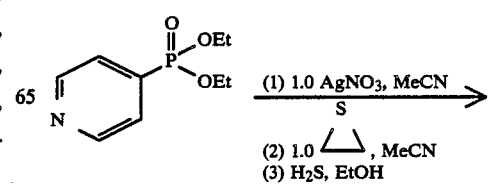

-continued

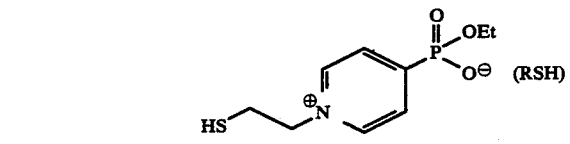

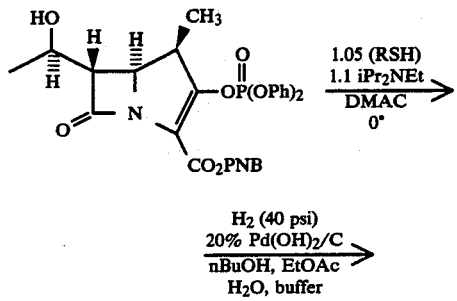

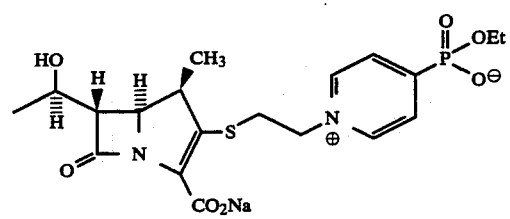

UV (H₂O) λ max 278, 293(85% NH₂₀H ext.) nm.
NMR (D₂O) δ 1.18(d, 1-CH₃), 1.31(d, C$\underline{H_3}$CHOH), 1.42(t, C₂C$\underline{H_3}$), 3.18–3.40(m, SCHaHb and H1), 3.46(dd, H6), 3.54–3.74(dt, SCHaHb, 4.04(dd, H5), 4.9–5.14(m, CH₂N), 8.50(dd, pyridyl H3, H5), 9.12(dd, pyridyl H2,H6).

EXAMPLE 54

Sodium (1R5S,6S)-2-[2-[4-[(ethoxy)oxidophosphinyl-methyl]-1pyridinumethylthio]-6-[I(R)-hydroxyethyl]-1-methylcarbapen-2-em-3-carboxylate

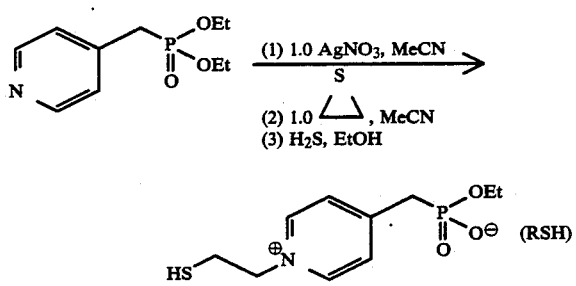

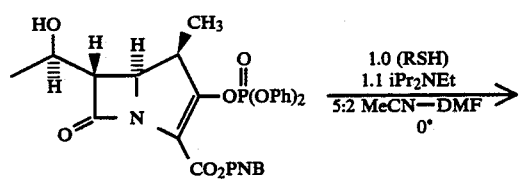

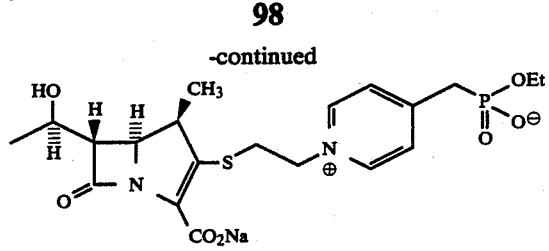

UV (H₂O) λ max 265, 295 (84% NHOH ext.) nm.
NMR (D₂O) δ 1.9(d, 1-CH₃), 1.36(d, C$\underline{H_3}$CHOH), 1.36(t. CH₃CH₂), 3.1–3.42(m, SCHaHb and H1), 3.49(dd, H6), 3.52–3.72(m, SCHaHb), 4.06(dd, H5), 4.14–4.4(m, CH₃CHOH and CH₃C$\underline{H_2}$), 4.82(HOD), 4.8–5.0(m, CH₂N), 8.l(dd, pyridyl H3, $\overline{H}$5), 8.86(d, pyridyl H2,H6).

EXAMPLE 55

Sodium(1R,5S,6S)-2-[2-[2-[4-[(amino)oxidophosphinylmethyl]-1pyridinium]ethylthio]-6-[1(R)-hydroxyethyl]-1-methylcarbapen-2-em-3carboxylate

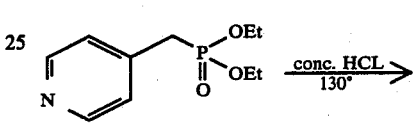

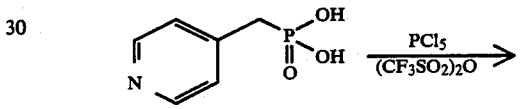

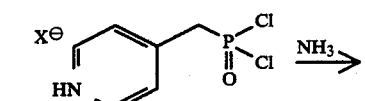

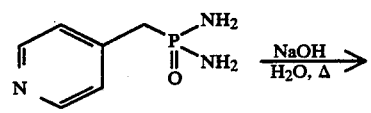

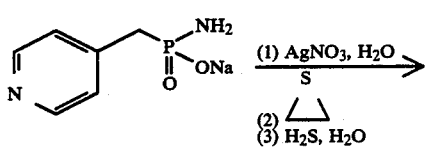

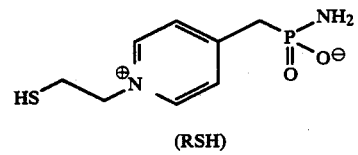

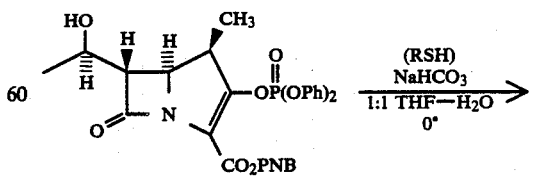

-continued

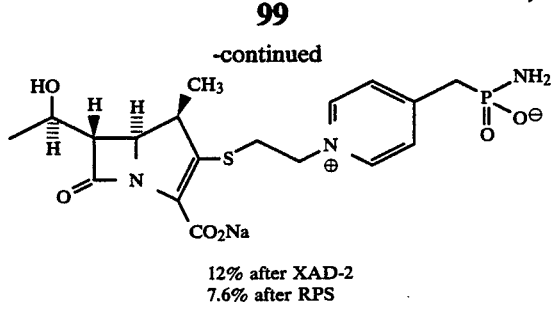

12% after XAD-2
7.6% after RPS

UV H₂O) λ max 242( 8520), 292( 5050, 75% NH₂OH ext.)nm.

NMR (D₂O) 1.18(d, 1-CH₃), b 1.32(d, CH₃CHOH), 3.1–3.7(m, SCH₂ and H1), 3.43(d, CH₂P), 3.44(dd, H6), 4.04(dd, H5), 4.28(p, CH₃CHOH), 7.96(dd, pyridyl H3,H5), 8.70(d, pyridyl H2,H6).

EXAMPLE 56

Sodium(1R,5S,6S)-2-[2-[4-[(hydroxy)oxidophosphinylmethyl]-1pyidinium]ethylthio]-6-[1(R)-hydroxyethyl]-1-methylcarbapen-2-em-3-carboxylate

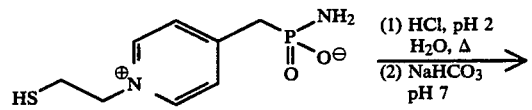

-continued

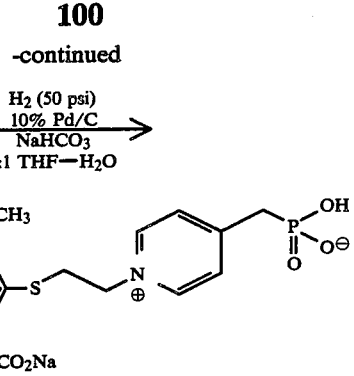

13% after XAD-2
7% after RPS

UV (H₂O) λ max 248 ( 6480), 292(ε3930) nm.
UV (H₂O+NH₂OH) λ max ext. 296(ε ext. 3360) nm.
NMR (D₂O) 1.17(d, 1-CH₃), 1.31(d, CH₃CHOH), 3.2–3.7(m, SCH₂ and H1), 3.31(d, CH₂P), 3.44(dd, H6), 4.01(dd, H5), 4.25(p, CH₃CHOH), 7.91(dd, pyridyl H3,H5), 8.62(d, pyridyl H2,H6).

EXAMPLE 57

Sodium (1R,5S-6S)-2-[-2-[4-[(ethoxy)oxidophosphinyloxymethyl]-1pyridinium]ethylthio]-6-[1(R)-hydroxyethyl]-1-methylcarbapen-2-em-3carboxylate

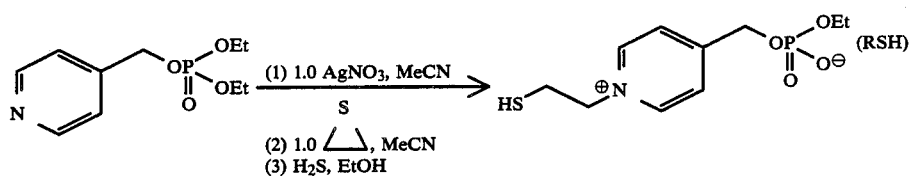

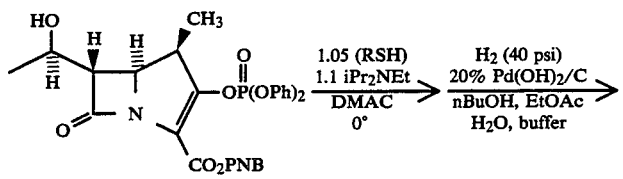

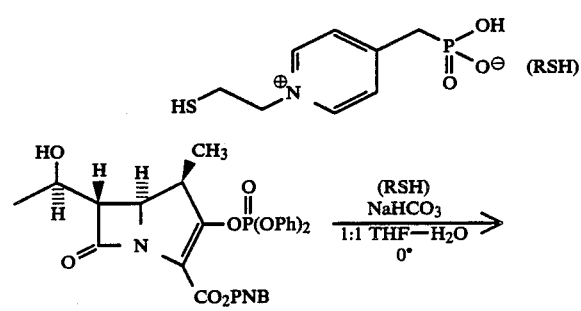

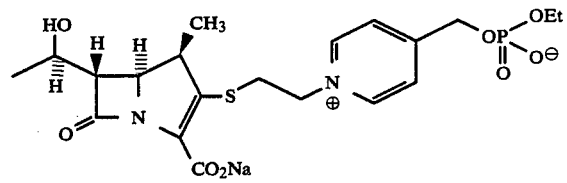

UV (H₂O) λ max 295 nm.
UV (H₂O+NH₂OH) λ max ext 297 (85% ext.) nm.
NMR (D₂O) δ 1.16(d, I-CH₃), 1.30(d, CH₃CHOH), 1.40(t, CH₃CH₂), 3.1–3.7(m, SCH₂, H1 and H6), 4.00(dd, H5), 4.8(HOD), 4.7–5.09(m, CH₂N), 5.53(d,pyridyl-CH₂), 8.11(d, pyridyl H3,H5), 8.89(pyridyl H2, H6).

EXAMPLE 58

Potassium (1R5S,6S)-6-[1(R)-hydroxyethyl]-2-[2-[4-(5-tetrazolatomethy -1-pyridinium]ethylthio]-1-methylcarbapen-2-em-1-carboxylate

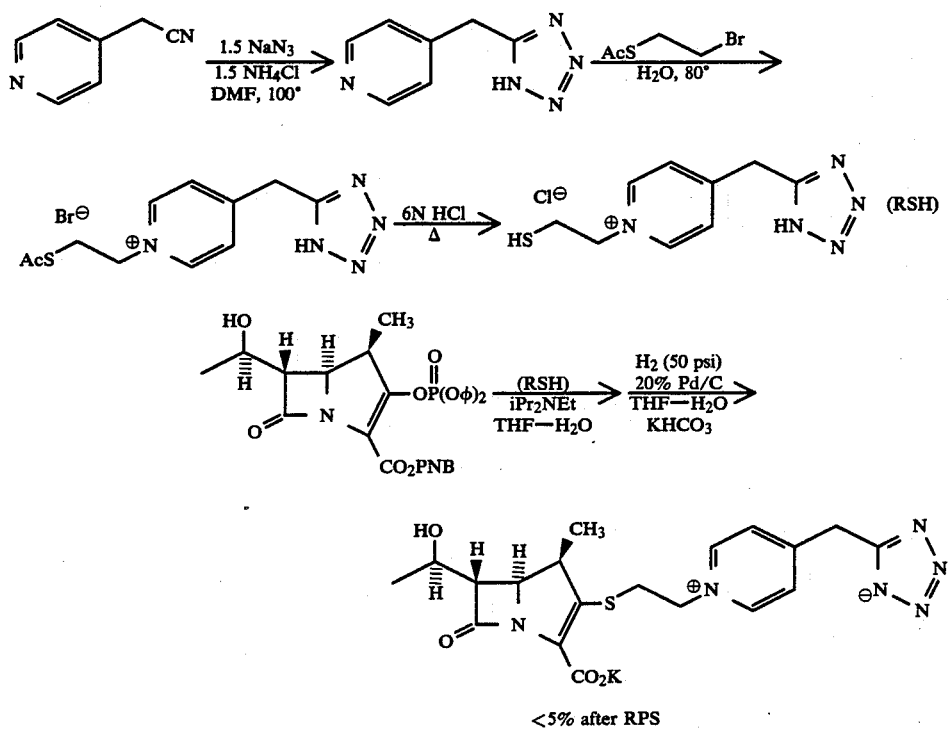
UV (H₂O) λ max 256.5, 295 (88% NH₂OH ext.) nm.
NMR (D₂O) δ1.06(d, CH₃CH), 1.28(d, CH₃CHOH), 3.09(dq, HI), 3.15–3.58(m, SCH₂), 3.37(dd, H6), 3.76(dd, H5), 4.20(p, CH₃CHOH), 4.80(m, CH₂N), 4.84(HOD), 7.87(d, pyridyl H̄3,H5), 8.71(d, pyridyl H2,H6).
EXAMPLE 59
Sodium (1R5S,6S)-2-[2-[4-[1,1-dioxo-3-keto-4-oxido-2,3-dihydro(2H)-1,2,5-thiadiazol-2-ylmethyl]-1-pyridinium]ethylthio]-6-[1(R)-hydroxyethyl]-1-methyl-carbapen-2-em-3-carboxylate
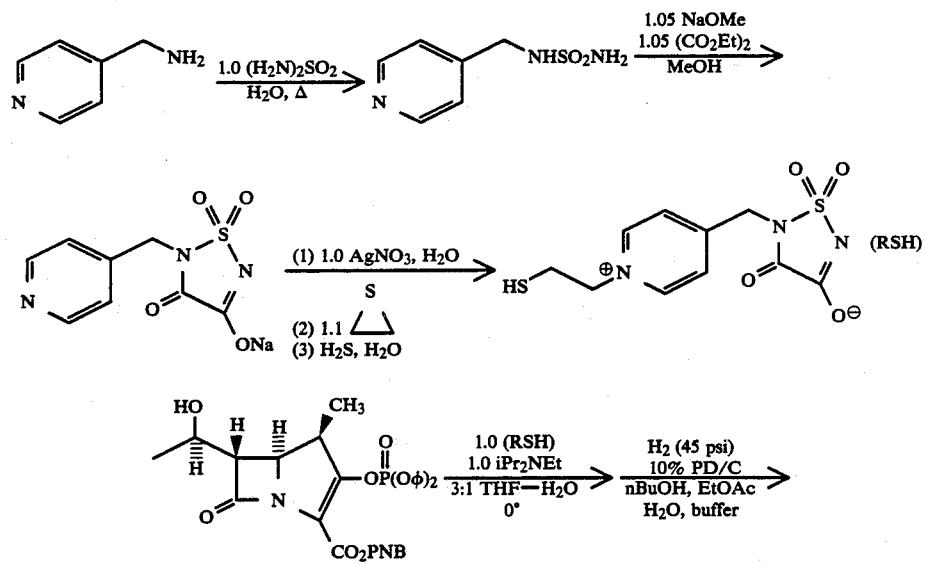

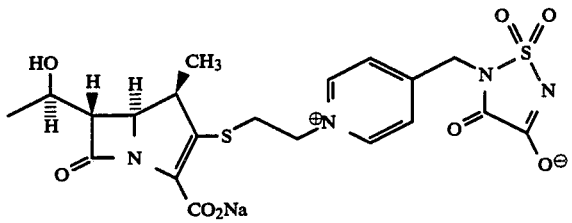

18% crude
16% after Dowex
12% after RPS

IR (Nujol) 3400(br), 1740, 1675, 1640, 1590 1170 cm$^{-1}$.

UV (H$_2$O) λ max 210(ε13600), 258(ε5920), 295(ε6470) nm.

UV (H$_2$O+NH$_2$OH) λ max ext 297(εext. 5670) nm.

NMR (D$_2$O) δ1.12(d, 1-CH$_3$), 1.29(d, CH$_3$CHOH), 3.18(qd, H1), 3.28 and 3.53(two td, SCH$_2$), 3.39(dd, H6), 3.95(dd, H5), 4.24(p, CH$_3$CHOH), 4.7–4.9 (m, CH$_2$N), 5.24(s, pyridiyl CH$_2$), 8.08(d, pyridyl H3,H5), 8.83(d, pyridyl H2,H6).

EXAMPLE 60

Sodium (1R5S,6S)-2-[2-[4-[(N-acetyl)sulfamoylatomethyl]-1-pyridinium]ethylthio]-6-[1(R)-hydroxyethyl]-1-methylcarba-pen-2-em-3-carboxylate UV (H$_2$O) λ max 233(ε7990), 292(ε5023, 80% NH$_2$OH ext.) nm.

NMR (D$_2$O) δ1.17(d, 1-CH$_3$), 1.32(d,CH$_3$CHOH), 3.16–3.41(m, SCHaHb and H1), 3.45(dd, H6), 3.60(td, SCHaHb), 4.04(d, H5), 4.27(p,CH$_3$CHOH), 4.83(HOD), 4.87(m, CH$_2$N), 8.08(d, pyridyl H3,H5), 8.86(d, pyridyl H2,H6).

EXAMPLE 61

Sodium (1R5S,6S)-6-[1(R)-hydroxyethyl]-2-[2-[4-(N-methyl-carbamoyl) sulfamoylatomethyl-1-pyridinium-]ethylthio]-1-methylcarbapen-2-em-3-carboxylate

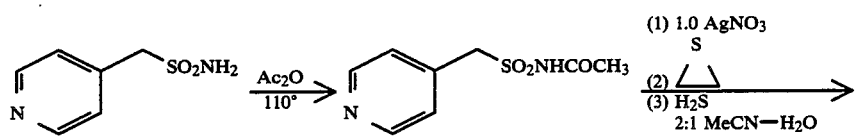

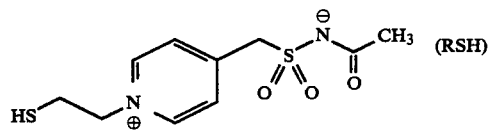

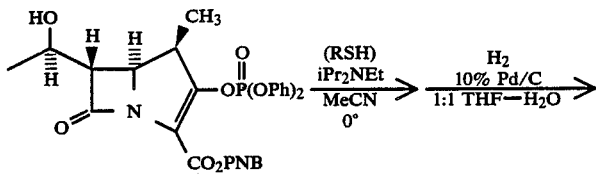

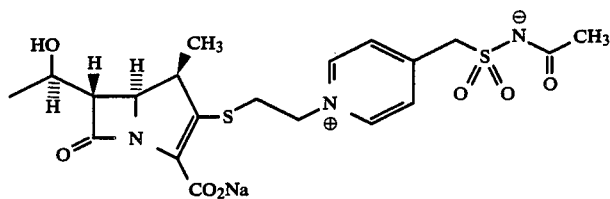

14% after Dowex

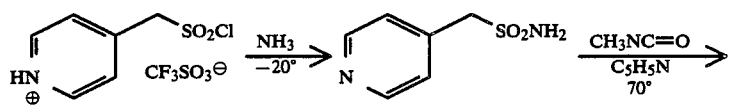

-continued

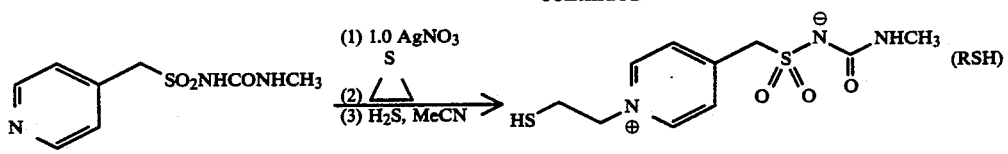

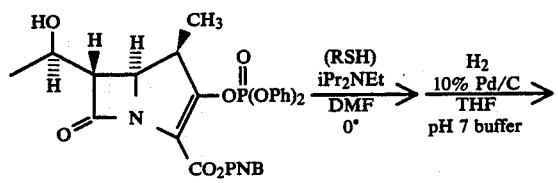

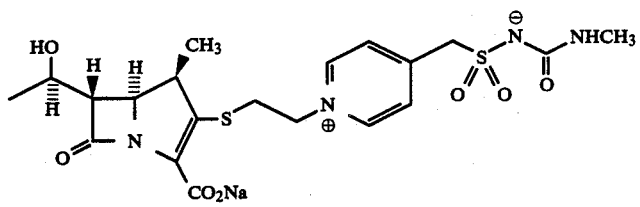

7% after Dowex and RPS

UV (pH 7 buffer) λ max 292 (ε7400) nm.
UV (buffer+NH₂OH) λ max ext. 297(εext. 6430)nm.
NMR (D₂O) δ1.20(d, 1-CH₃), 1.34(d,CH₃CHOH), 2.74(s, SCH₃), 3.2–3.45(m, SCHaMb and M$\overline{l}$), 3.49(OD H6), 3.64(td, SCHaHb), 4.09(d, H5), 4.29(p, CH₃CHOH), 4.87(HOD), 4.94(m, CH₂N), 8.14(d, pyridyl H3,H5), 8.92(d, pyridyl H2,H6).

UV (H₂O) λ max 295(ε7380, 66% NH₂OH ext.) nm.
NMR (D₂O) δ1.32(d,CH₃CHOH), 3.09(m, CH₂), 3.38(m, SCHaHb), 3.42(dd, H6), 3.57(td, SCHaHb), 4.15(dt, H5), 4.26(p,CH₃CHOH), 4.84(HOD masking CH₂N), 7.15 and 7.39(two m, phenyl, 8.05(d, pyridyl H3,H5), 8.82(d, pyridyl H2,H6).

EXAMPLE 62
Sodium (5R,6S)-6-[I(R)-hydroxyethyl]-1-[2-[4-(N-phenyl)sulfamoylmethyl-1-pyridinium]ethylthio]-carbapen-2-em-3-carboxylate

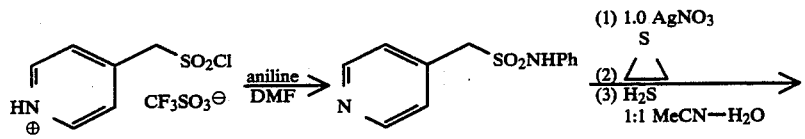

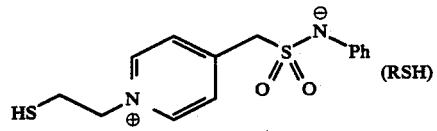

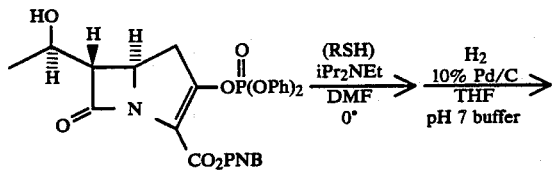

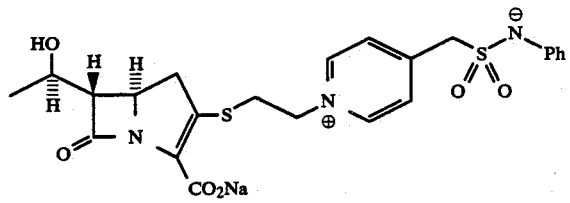

EXAMPLE 63

Sodium (1R5S,6S)-6-[1(R)-hydroxyethyl]-2-[2-[4-(N-methylsulfonyl)carbamoylato-1-pyridinium]ethylthio]-1-methyl-carbapen-2-em-3-carboxylate NMR (D$_2$O) δ1.21(d, CH$_3$CH), 1.35(d,CH$_3$CHOH), 3.27(s, SO$_2$CH$_3$), 3.28(m, $\overline{\text{CH}_3\text{CH}}$), 3.34 and 3.64(two m's SCH$_2$, 3.49(dd, H6), 4.04(dd, H5), 4.28(p,CH$_3$CHOH), 4.87(HOD), 4.98(m, CH$_2$), 8.50(d, pyridyl H3,H$\overline{5}$), 9.00(d, pyridyl H2,H6).

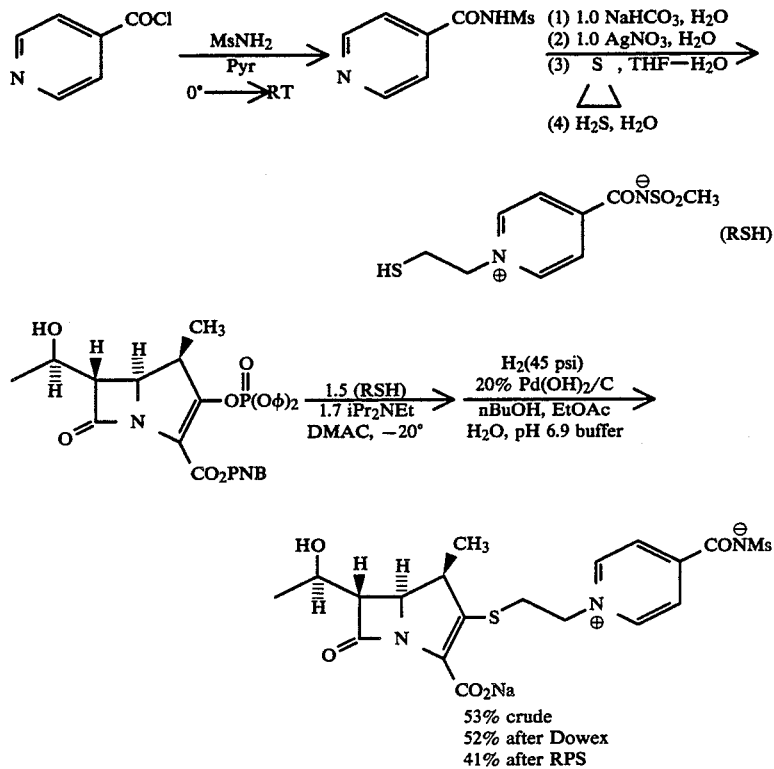

IR (Nujol) 3410(br, 1744, 1597, 1560, 1260, 1145, 1115 cm$^{-1}$.

UV (0.05M pH 7.0 MOPS buffer) λ max 275(ε10,550), 290(sh, ε 10,310)nm

UV (buffer+NH$_2$OH) λ max ext. 295(εext. 6830)nm.

EXAMPLE 64

Sodium (1R5S,6S)-6-[1(R)-hydroxyethyl]-2-[2-[4-[N-(p-toluylsulfonyl)carbamoylato]-1-pyridinium)ethylthio)-1-methylcarbapen-2-em-3-carboxylate

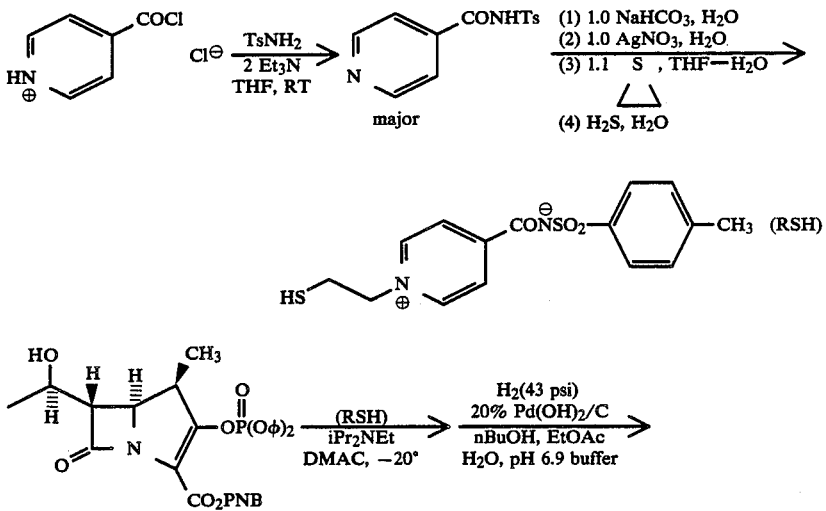

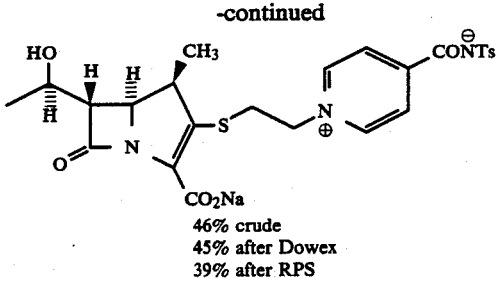

46% crude
45% after Dowex
39% after RPS

IR (Nujol) 3380 (br), 1750, 1726, 1638, 1602, 1560, 1263, 1134, 1080 cm$^{-1}$.

UV (0.05 pH 7.0 MOPS buffer) λ max 275(sh, ε11,500), 292(ε 11,830)nm.

UV(buffer+NH2OH) λ max ext. 295(εext. 6740)nm.

NMR (D$_2$O) δ 1.17(d, CH$_3$CH), 1.31(d,CH$_3$CHOH), 3.20(m, H1), 3.42(dd, H6), 3.36 and 3.61(two m's, SCH$_2$), 3.91(dd, H5), 4.12(p,CH$_3$CHOH), 4.87(HOD), 4.95(t, CH$_2$N), 7.48 and 7.91 (two d's, aryl H's), 8.44(d, pyridyl H3,H5), 8.97(d, pyridyl H2,H6).

EXAMPLE 65

Sodium (5R,6S)-6-[I(R)-hydroxyethyl]-2-[2-[4-[(N-cyano) sulfamoylatomethyl]-1-pyridinium]ethylthio]carbapen-2-em-3-carboxylate resulting solution was heated to 95° C. for an additional hour then cooled and the excess sodium sulfite decomposed by the slow addition of conc. HCl (375 ml). The solution was concentrated to a wet cake and ethanol (500 ml) was added. The solid was collected and washed with additional ethanol (300 ml). The partially dried cake was suspended in conc. HCl (350 ml) and the NaCl filtered off and washed with more conc. HCl (100 ml). Ethanol (1.5 l) was slowly added to the combined filtrates causing the product to crystallize. After aging at 0° C. for 2 hrs, the product was collected, washed with ethanol (200 ml) and dried to give a white solid (235 g, 74% yield). A 200 MHz NMR spectrum of the product showed about 6% of the dimeric impurity 1-(4-pyridylmethyl)-4-(sulfomethyl)pyridinium chloride.

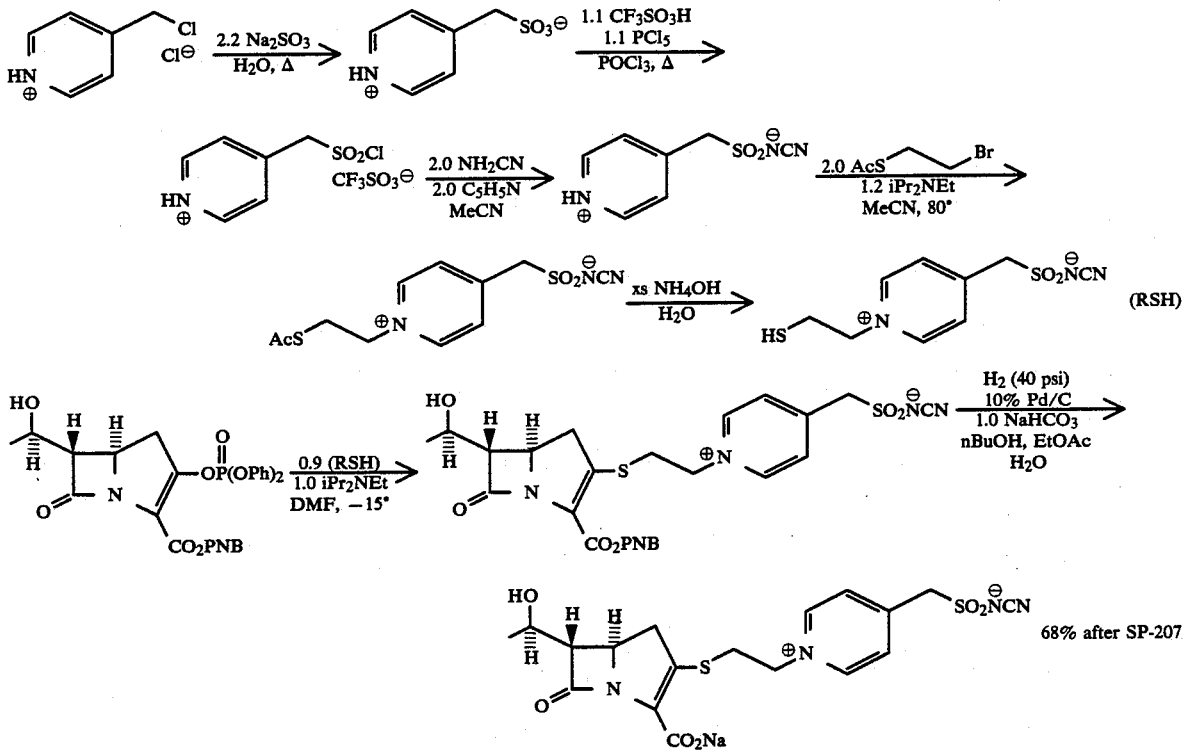

Detailed procedures and physical data follow:

STEP 1

4-Pyridylmethanesulfonic acid

To a stirred solution of sodium sulfite (500 g, 3.97 mol) in water (1.2 l) heated to 60° C. was added a solution of 4-picolyl chloride hydrochloride (300 g, 1.83 mol) in water (300 ml) during a period of 1 hr. The

STEP 2

4-Pyridylmethanesulfonyl chloride triflate

Trifluoromethanesulfonic acid (100 g, 0.67 mol) was rapidly added to a suspension of 4-pyridylmethanesulfonic acid (103 g, 0.6 mol) in phosphorous oxychloride (300 ml). The pyridylmethanesulfonic acid dissolved and reprecipitated as the triflate salt. The resulting suspension was cooled in ice for 30 min, then treated with phosphorous pentachloride (139 g, 0.67 mol) in Portions during 10 minutes. The mixture was allowed to warm to room temperature over 30 min and was then cautiously heated to reflux over a period of 1.5 hrs during which time extensive gas evolution occurred. After refluxing for 1 hr, the excess phosphorous oxychloride was distilled off under vacuum while maintaining the pot temperature below 80° C. The residual solid was dissolved in acetonitrile (200 ml), filtered and crystallized by the gradual addition of ether (400 ml). The product was recovered by filtration and washed with ether to afford a white solid (170 g, 84%).

mp 116°–118° C.

NMR (CD$_3$CN) δ 2.51 (CH$_3$CN), 6.05 (s, CH$_2$SO$_2$), 8.79 (d, J=6.3 Hz, H3, H5), 9.39(d, J=6.3 Hz, H2, H6).

STEP 3

N-Cyano-4-pyridylmethanesulfonamide

Anhydrous cyanamide (32 g, 0.76 mol) was dissolved in acetonitrile (600 ml) in a 2 l, 3-necked flask equipped with a mechanical stirrer, drying tube, and two dropping funnels. The solution was cooled in a 1:1 ethanol-water bath that was maintained at −20° C. by the addition of dry ice. Solutions of pyridine (57 g, 0.72 mol) in acetonitrile (70 ml) and of 4-pyridylmethanesulfonyl chloride triflate (130 g, 0.38 mol) in acetonitrile (200 ml) were added simultaneously at such a rate that the additions of both solutions were completed in 3 hrs. The resulting suspension was stirred at −10° C. for 1 hr and then filtered and the solids washed with cold acetonitrile (50 ml). The solid portion was recrystallized by adding it to ice-cold water (100 ml). The product was filtered off and washed with ice-water (100 ml) to give a light yellow solid (49.5 g). The mother liquors were refrigerated overnight to give additional product (5 g, 73% total yield).

mp>250° C. (dec).

IR (Nujol) 2165 cm$^{-1}$.

NMR (D$_2$O+NaHCO$_3$) δ4.28 (s, CH$_2$SO$_2$), 4.71 (HOD), 7.49 (d, J=6.1 Hz, H3, H5), 8.50 (d, J=6.1 Hz, H2, H6).

Microanalytical: Calc'd C, 42.63; H, 3.58; N, 21.31; Found C, 42.63; H, 3.68; N, 21.14.

STEP 4

1-[2-(Acetylthio)ethyl]-4-[(N-cyano)sulfamoylmethyl]-pyridinium hydroxide, inner salt A solution of N-cyano-4-pyridylmethanesulfonamide (51.7 g, 0.26 mol), 2-bromoethyl thiolacetate (95.8 g, 0.52 mol), and N,N-diisopropylethylamine (40.8 g, 0.32 mol) in acetonitrile (500 ml) was heated at 80° C. for 24 hrs. The resulting suspension was filtered and the Precipitate washed with acetonitrile (500 ml) to afford the Product as a light yellow solid (39.5 g). The filtrate was evaporated and the residue slurried with methylene chloride (100 ml) to give additional product (2.8 g) after filtration. The filtrate was reevaporated and the residue dissolved in water (200 ml) and applied to a 5×30 cm Dowex 50W-X4 column (sodium form, 200–400 mesh). The column was eluted with water (1.2 l) and the eluate was treated with activated carbon at room temperature, filtered and evaporated to 100 ml. The resulting slurry was cooled in ice and the product (7.5 g) recovered by filtration. The total yield of product was 49.8 g (63.5%).

mp 215° C. (dec).

IR (Nujol) 2165, 1645 cm$^{-1}$.

NMR (DMSO-d$_6$) δ 2.31 (s, SCOCH$_3$), 2.51 (DMSO-d$_5$ J=6.0 Hz, SCH$_2$), 4.57 (s, CH$_2$SO$_2$), 4.75 (t, J=6.0 Hz, CH$_2$N), 8.10 (d, J=6.0 Hz, H3, H5), 9.01 (d, J=6.0 Hz, H2, H6).

UV (H$_2$O) λ $_{max}$ 260 (ε 6,700), 230 (ε 11,000) nm.

Microanalytical: Calc'd C, 44.13; H, 4.38; N, 14.04; S, 21.42; Found C, 43.96; H, 4.40; N, 14.09; S, 21.47.

STEP 5

1-[2-Mercaptoethyl]-4-[(N-cyano)sulfamoylmethyl]-pyridinium hydroxide, inner salt The N-acetylthioethyl pyridinium derivative of step 4 (42.7 g, 0.14 mol) was added to a stirred, 10% aqueous ammonium hydroxide solution (450 ml) which had been purged with nitrogen. Immediately after the solution cleared, it was evaporated under vacuum to an oil. This material was diluted with water (500 ml), seeded and reevaporated to 150 ml. The resulting crystalline slurry was chilled in ice for 30 min, then filtered and the cake washed with cold water to afford the product as an off-white solid (61 g, 94%).

mp 124°–127° C. (eff).

IR (Nujol) 2165 cm$^{-1}$.

NMR (DMSO-d$_6$) δ2.51 (DMSO-d$_5$), 2.71 (t, CH$_2$SH), 3.12 (dt, CH$_2$SH), 4.58 (s, CH$_2$SO$_2$), 4.71 (t, CH$_2$N), 8.13 (d, J=6.1 Hz, H3, H5), 9.00 (d, J=6.1 Hz, H2, H6).

STEP 6 p-Nitrobenzyl (5R,6S)-6-[1(R)-hydroxyethyl]-2-[2-[4-[(N-cyano)sulfamoylatomethyl]-1-pyridinium]ethylthio]-carbapen-2-em-3-carboxylate A suspension of p-nitrobenzyl (5R,6S)-2-(diphenylphosphono)oxy-6-[1(R)-hydroxyethyl]carbapen-2-em-3-carboxylate (75.4 g, 0.13 mol) and the mercaptan of step 5 (30.9 g, 0.12 mol) in DMF (300 ml) was cooled to −15° C. under a nitrogen atmosphere. N,N-Diisopropylethylamine (16.8 g, 0.13 mol) was added via syringe to the stirred solution during 20 minutes. After an additional 40 min, the DMF was partially evaporated (200 ml) and ethanol (1 l) was slowly added. After stirring for 30 min at room temperature, the precipitate was filtered and washed with ethanol (200 ml). The resulting amorphous solid was crystallized by adding it in small portions over a period of 1 hr to a stirred solution of acetonitrile (600 ml) and water (30 ml) (Note: after 15 g had been added the solution was seeded with 1 g of finely ground Product derived from a previous run). The resulting mixture was stirred for 30 min at room temperature and for 1 hr in an ice bath, then filtered and the cake washed with 95% acetonitrile to give the Product as a cream colored powder (63.1 g, 85%). This material was found by NMR to be a solvate containing one-half mole of acetonitrile.

mp 140°–145° C. (dec).

IR (Nujol) 2165, 1775 cm$^{-1}$.

NMR (DMSO-d$_6$) δ 1.23 (d, CH$_3$CHOH), 2.06 (s, CH$_3$CN), 2.49 (DMSO-d$_5$), 3.2–3.6 (m, carbapenem CH$_2$), 3.40 (dd, H6), 3.54 (t, SCH$_2$), 3.97 (m, CH$_3$CHOH), 4.19 (m, H5), 4.57 (s, CH$_2$SO$_2$), 4.83 (t, CH$_2$N), 5.13 (d, OH), 5.37 (ABq, CH$_2$Ar), 7.69 and 8.23 (two d, ArH), 8.13 (d, pyridyl H3, H5), 9.03 (d, pyridyl H2, H6).

STEP 7

Sodium (5R,6S)-6-[1(R)-hydroxyethyl]2-2-2-[4-[(N-cyano)sulfamoylatomethyl]--pyridinium]ethylthiol-carbapen-2-em-3-carboxylate The ester of step 6 (12.3 g, 0.02 mol) was ground in a mortar with a portion of butanol then transferred to a 2.3 1 hydrogenation vessel containing the remaining butanol (360 ml total), ethyl acetate (180 ml), water (720 ml), sodium bicarbonate (1.58 g, 0.019 mol), and 10% palladium on carbon (4.5 g). The mixture was hydrogenated at 40 psi for 40 min then vented, flushed, repressurized and shaken for an additional 80 min. The aqueous layer was filtered through prewashed Solka-Floc to remove catalyst. The organic layer was washed with water (120 ml) and the aqueous layer used to wash the filter cake. The PH of the combined aqueous layers was adjusted to 7.0 with dilute HCl. The solution was evaporated under vacuum to a volume of 150 ml then applied to an ice-water jacketed column of SP-207 resin (5×25 cm, 500 ml). The column was initially eluted with DI water followed by elution with 5% methanol in water, and the Progress of the separation was followed by UV measurement of the absorbance ratio at 295/262nm. The main fraction was collected when this ratio was greater than 0.92. In a typical chromatography, a forerun was collected between elution volumes of 700 and 1300 ml, the solvent was changed to 5% methanol in water, the main fraction was collected between 1300 and 3000 ml, and the tails between 3000 and 3600 ml. The main fraction was concentrated under vacuum to a volume of 150 ml and freeze-dried to give the product as a light yellow powder (6.3 g) having a $NH_2OH$ extinguished UV absorbance at $\lambda_{max}$ 297 nm ($\epsilon_{ext}$7000). The combined tails and forerun yielded slightly less pure product (1.2g) having $\epsilon_{ext}$6000. The total isolated yield based on an assumed $\epsilon_{ext}$ of 8000 was 68%.

IR (Nujol) 2165, 1745 (br) $cm^{-1}$.

NMR ($D_2O$) δ 1.25 (d, $CH_3CH$), 2.92 and 3.07 (two dd, carbapenem $CH_2$), 3.36 $\overline{H}$6), 3.34 and 3.52 (two td, $SCH_2$), 4.06 (dt, H5), 4.19 (dq, $CH_3CH$), 4.74 (HOD), 4.84 (s, $CH_2SO_2$), 4.86 (m, $CH_2N$), 8.17 (d, pyridyl H3, H5), 8.88 (d, pyridyl H2, H6).

EXAMPLE 66

Sodium (1R,5S,6S)-6-[I(R)-hydroxyethyl]-2-[2-[4-[(N-cyano)-sulfamoylatomethyl]-1-pyridinium]ethylthio]-1-methyl-carbapen-2-em-3carboxylate

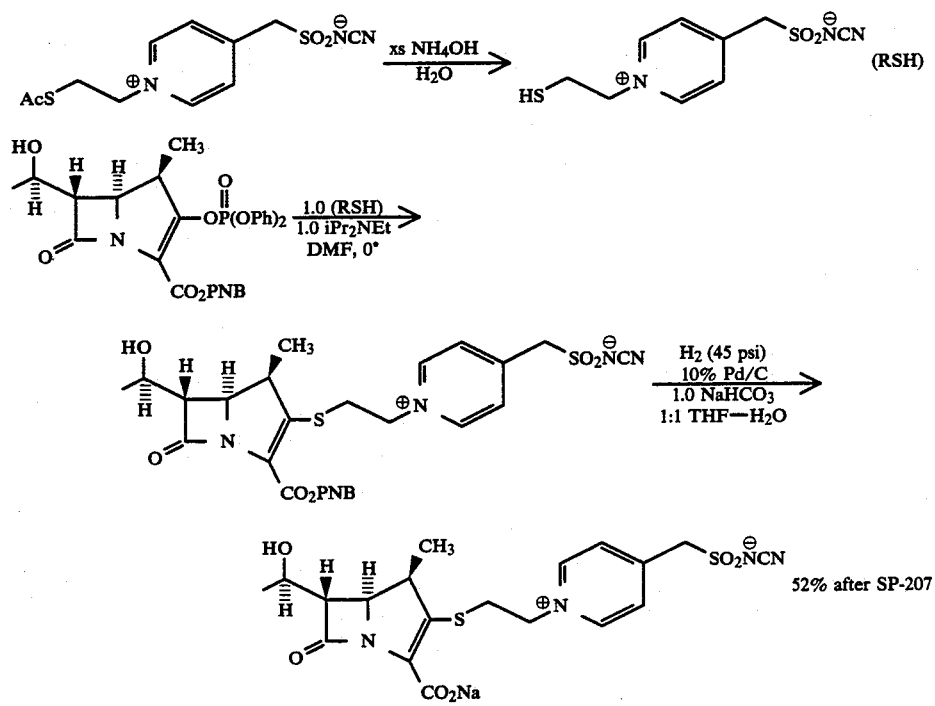

Detailed procedures and physical data follow:

STEP 1

1-[2-Mercaptoethyl]-4-[(N-cyano)sulfamoylmethyl]-pyridinium hydroxide, inner salt Solid 1-[2-(acetylthio)ethyl]-4-[(N-cyano)-sulfamoylmethyl]pyridinium hydroxide inner salt (1.5 g, 5.01 mmol) was dissolved in an aqueous ammonium hydroxide solution (35 ml) which had been purged with nitrogen. After 1 min, the solution was evaporated under vacuum to remove excess ammonia and water. The residue was twice diluted with water and evaporated under vacuum and then diluted with ethanol and pumped dry to afford the crude mercaptan in 100% yield. This material was used in the next step without further purification.

STEP 2 p-Nitrobenzyl (1R,5S,6S)-6-[1(R)-hydroxyethyl]-2-[2-[4-[(N-cyano)-sulfamoylatomethyl]-1-pyridinium]ethylthio]-1-methyl-carbapen-2-em-3-carboxylate The mercaptan from step 1 (5.01 mmol) was dissolved in DMF (15 ml) and the solution was cooled in an ice bath and stirred under a nitrogen atmosphere. p-Nitrobenzyl (1R,5R,6S)-2-(diphenylphosphono)oxy-6-[1(R)-hydroxyethyl]-1-methyl-carbapen-2-em-3-carboxylate (3.0 g, 5.05 mmol) was added in one portion followed by the dropwise addition of N,N-diisopropylethylamine (0.9 ml, 5.17 mmol) over 5 min. The resulting solution was stirred in the cold for 40 min then evaporated under vacuum to remove the DMF. The syrupy residue was triturated with ethanol to afford the product (2.88 g, 95%) as an amorphous solid. This material was immediately ester deblocked a described in the following step.

STEP 3

Sodium (1R,5S,6S)-6-[1(R)-hydroxyethyl]-2-[2-[4-[(N-cyano)-sulfamoylatomethyl]-1-pyridinium]ethylthio]-1-methyl-carbapen-2-em-3-carboxylate The crude ester (2.88 g, 4.79 mmol) from step 2 was dissolved in 1:1 THF-$H_2O$ (300 ml) and treated with $NaHCO_3$ (0.41 g, 4.88 mmol). The resulting solution was divided into two equal parts and each portion was treated with 10% palladium on powdered charcoal (0.75 g) and hydrogenated at 45 psi for 2 hr. The two mixtures were combined and filtered to remove the catalyst which was washed with water containing a few drops of saturated brine. The aqueous filtrate was extracted with ether, acidified from pH 7.35 to pH 6.65 with dilute HCl, and carefully concentrated under reduced pressure (foaming) to ca. 20 ml. This solution was added to an ice-water jacketed column of SP-207 resin (2.5×32 cm, 160 ml) that was eluted first with DI $H_2O$ (375 ml), then with 5% MeOH/$H_2O$ (875 ml), and finally with 10% MeOH/$H_2O$; 25 ml fractions were collected approximately every 6 min. The progress of the separation was followed by UV measurement of the absorbance ratio at 293/258 nm. Fractions 23–60 (absorbance ratio ≥0.96) were combined, concentrated under vacuum, and freeze-dried to give the product (1.42 g) as a light yellow powder having a $NH_2OH$ extinguished UV absorbance at $\lambda_{max}$ 297 nm ($\epsilon_{ext}$ 6800). Fractions 20–22 and fractions 61–75 were separately concentrated and freeze-dried to provide slightly less pure product. The isolated yield of center cut material was 52% based on an assumed $\epsilon_{ext}$ of 8000 for 100% purity.

NMR ($D_2O$)δ1.10 (d, 1-$CH_3$), 1.23 (d, $CH_3CHOH$), 3.20 (m, H1), 3.26 (td, SCHaHb), 3.40 (dd, H6), 3.53(td, SCHa b), 3.98(dd, H5), 4.20 (dq, $CH_3CHOH$), 4.74 (HOD), 4.83 (s, $CH_2SO_2$), 4.86 (t, $CH_2N$), 8.16 (d, pyridyl H3, H5), 8.85 (d, pyridyl H2, H6).

EXAMPLE 67

Sodium (5R,6S)-2-[2-[3-chloro-4-[(N-cyano) sulfamoylatomethyl]-1-pyridinium]ethylthio]-6-[1(R)-hydroxyethyl]carbapen-2-em-3-carboxylate

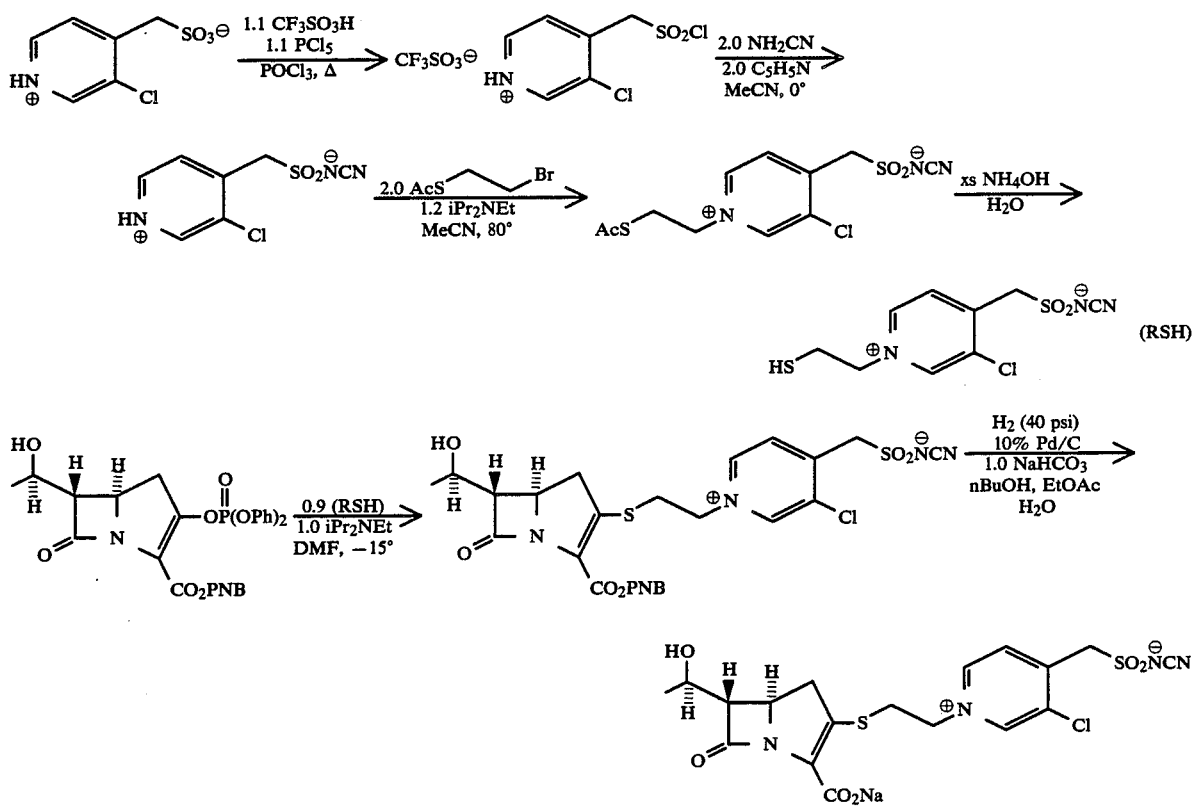

UV ($H_2O$+$NH_2OH$) λmax ext. 298 (ε ext 4,130)nm. NMR ($D_2O$)δ1.24(d, $CH_3CHOH$), 3.04(two dd, $CH_2$) 3.36(dd, H6), 3.2–3.6(m, $\overline{SCH_2}$), 4.09(dt, H5), 4.19(dq, $CH_3CHOH$ ), 4.75(HOD), 4.86(m, $CH_2N$), 8.27(d, pyridyl $\overline{H5}$), 8.85(d, pyridyl H6), 9.20(s, pyridyl H2).

EXAMPLE 68

Sodium (5R,6S)-2-[2-[3-fluoro-4-[(N-cyano)sulfamoylatomethyl]-1-pyridinium]ethylthio-6-[1(R)-hydroxyethyl]carbapen-2-em-3carboxylate Uv (H₂O+NH₂OH) λ max ext. 297(εext 4,840)nm.
NMR (D₂O) δ1.27(d, CH₃CHOH), 3.08(two dd, CH₂), 3.39(dd, H6), 3.2–3.6(m, SCH₂), 4.16(dt, H5), 4.2(dq, CH₃C$\underline{H}$OH), 4.89(m, CH₂N), 8.3(t, pyridyl H5), 8.84(d, pyridyl H6), 9.15(d, pyridyl H2).

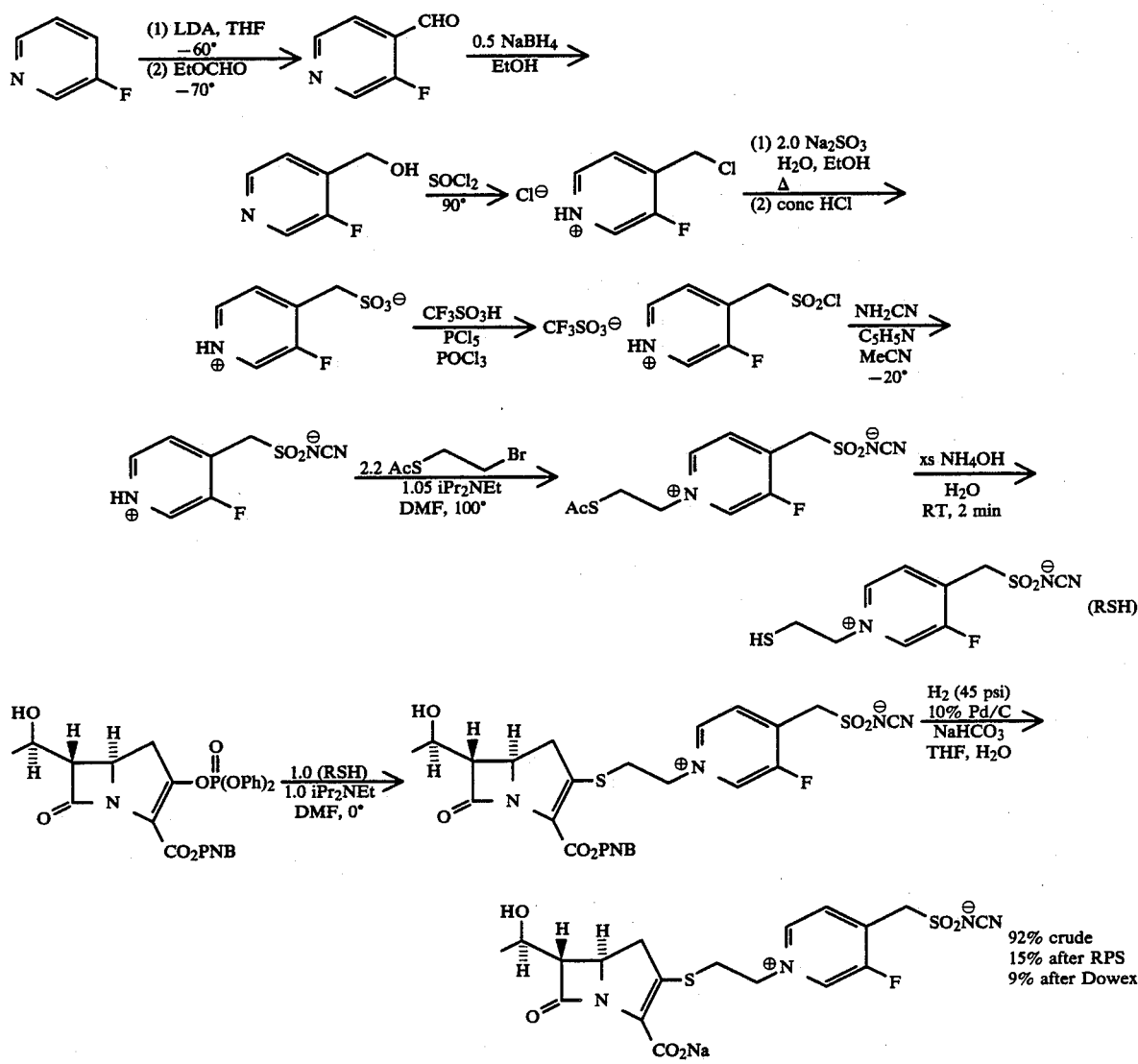

UV (H₂O) λ max 235(ε7,540), 273(ε7,990), 293(sh, ε6,500)nm.

EXAMPLE 69

Using procedures as described in Examples 1–68, the following formula 1 compounds are prepared:

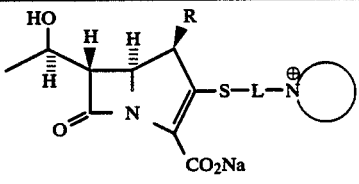

| Compound No. | R | L | –N⊕⟨ring⟩ |
|---|---|---|---|
| 1,2 | H,CH₃ | —CH₂CH₂— | 1-methylpyridinium-2-carboxylate |
| 3 | H | —CH₂CH₂— | 1-methylpyridinium-3-CH₂CO₂⁻ |
| 4 | H | —CH₂CH₂— | 1-methylpyridinium-4-carboxylate |
| 5,6 | H,CH₃ | —CH₂CH₂— | 1-methylpyridinium-3-CH₂CH₂CO₂⁻ |
| 7,8 | H,CH₃ | —CH₂CH₂— | 1-methylpyridinium-3-CH=CHCO₂⁻ |
| 9,10 | H,CH₃ | —CH₂CH₂— | 1-methylpyridinium-3-C(O)N(O⁻)OH |
| 11,12 | H,CH₃ | —CH₂CH₂— | 1-methylpyridinium-4-C(O)N(O⁻)OH |
| 13,14 | H,CH₃ | —CH₂CH₂— | 1-methylpyridinium-4-CONH₂-3-CO₂⁻ |
| 15,16 | H,CH₃ | —CH(CH₃)CH₂— | 1-methylpyridinium-3-CH₂CO₂⁻ |
| 17,18 | H,CH₃ | —CH(CH₃)CH₂— | 1-methylpyridinium-4-CO₂⁻ |

-continued
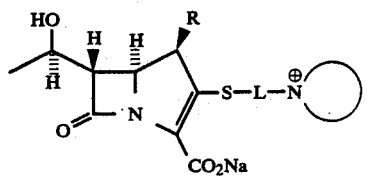
| Compound No. | R | L | |
|---|---|---|---|
| 19,20 | H,CH₃ | —CH₂CH₂— | 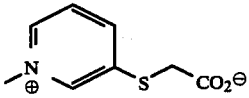 |
| 21,22 | H,CH₃ | —CH₂CH₂— | 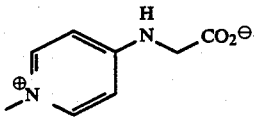 |
| 23,24 | H,CH₃ | —CH₂CH₂— | 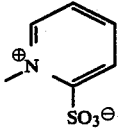 |
| 25 | H | —CH₂CH₂— | 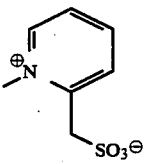 |
| 26 | H | —CH₂CH₂— | 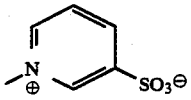 |
| 27 | H | —CH₂CH₂— | 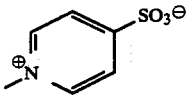 |
| 28 | H | —CH₂CH₂— | 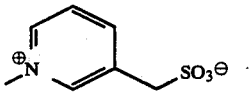 |
| 29 | H | —CH₂CH₂— | 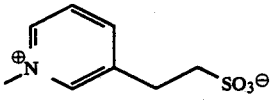 |
| 30 | CH₃ | —CH₂CH₂— | 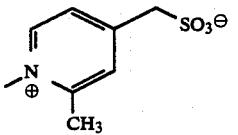 |

-continued

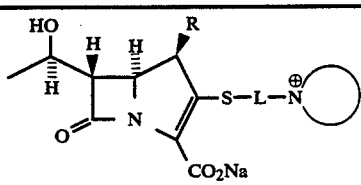

| Compound No. | R | L | |
|---|---|---|---|
| 31 | CH₃ | —CH₂CH₂— | pyridinium N-CH₃, 4-CH₂SO₃⁻, 3-SCH₃ |
| 32 | CH₃ | —CH₂CH₂— | pyridinium N-CH₃, 4-CH₂SO₃⁻, 3-Br |
| 33,34 | H,CH₃ | —CH₂CH₂— | pyridinium N-CH₃, 4-CH₂SO₃⁻, 3-CN |
| 35 | CH₃ | —CH₂CH₂— | pyridinium N-CH₃, 4-CH₂SO₃⁻, 3-CH₃ |
| 36 | CH₃ | —CH₂CH₂— | pyridinium N-CH₃, 4-CH₂SO₃⁻, 3-SO₂NHCH₃ |
| 37 | CH₃ | —CH₂CH₂— | pyridinium N-CH₃, 4-CH₂SO₃⁻, 3-CO₂CH₃ |
| 38 | CH₃ | —CH₂CH₂— | pyridinium N-CH₃, 4-CH₂SO₃⁻, 3-CH₂CH₃ |
| 39 | CH₃ | —CH₂CH₂— | pyridinium N-CH₃, 4-CH₂SO₃⁻, 3-CONH₂ |
| 40 | CH₃ | —CH₂CH₂— | pyridinium N-CH₃, 4-CH₂SO₃⁻, 3-NH₂ |
| 41 | CH₃ | —CH₂CH₂— | pyridinium N-CH₃, 4-CH₂SO₃⁻, 3-NHAc |
| 42 | CH₃ | —CH₂CH₂— | pyridinium N-CH₃, 4-CH₂SO₃⁻, 3-SO₂NH₂ |

-continued

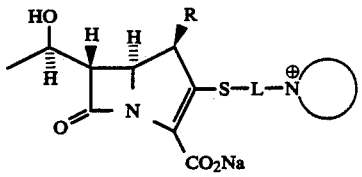

| Compound No. | R | L | |
|---|---|---|---|
| 43 | CH₃ | —CH₂CH₂— | pyridinium with CH₂SO₃⁻ and OCH₃, N-methyl |
| 44,45 | H,CH₃ | —CH₂CH₂— | pyridinium with CH(OH)SO₃⁻, N-methyl |
| 46,47 | H,CH₃ | —CH₂CH₂— | pyridinium with CH₂SO₃⁻ and CON(CH₃)₂, N-methyl |
| 48 | H | —CH₂CH₂— | pyridinium with CH₂SO₃⁻ and S(O)CH₃, N-methyl |
| 49 | CH₃ | —CH₂CH₂— | pyridinium with CH₂SO₃⁻ and SO₂CH₃, N-methyl |
| 50,51 | H,CH₃ | —CH₂CH₂— | pyridinium with CH₂SO₃⁻ and CF₃, N-methyl |
| 52,53 | H,CH₃ | —CH(CH₃)CH₂— | pyridinium with SO₃⁻, N-methyl |
| 54,55 | H,CH₃ | —CH(CH₃)CH₂— | pyridinium with CH₂SO₃⁻, N-methyl |
| 56,57 | H,CH₃ | —CH(CH₃)CH₂— | pyridinium with CH₂SO₃⁻ and F, N-methyl |
| 58,59 | H,CH₃ | —CH(CH₃)CH₂— | pyridinium with CH₂SO₃⁻ and Cl, N-methyl |

-continued

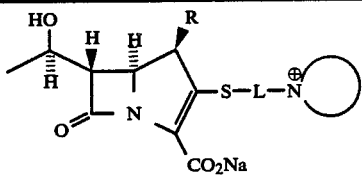

| Compound No. | R | L | |
|---|---|---|---|
| 60,61 | H,CH₃ | —CH(CH₃)CH₂— | pyridinium: N-methyl, 3-NH₂, 4-CH₂SO₃⁻ |
| 62,63 | H,CH₃ | —CH(CH₃)CH₂— | pyridinium: N-methyl, 3-CH₃, 4-CH₂SO₃⁻ |
| 62,63 | H,CH₃ | —CH(CH₃)CH₂— | pyridinium: N-methyl, 3-CH₃, 4-CH₂SO₃⁻ |
| 64,65 | H,CH₃ | —CH₂— | pyridinium: N-methyl, 4-CH₂SO₃⁻ |
| 66,67 | H,CH₃ | —CH₂CH₂— | pyridinium: N-methyl, 3-CN, 5-CH₂SO₃⁻ |
| 68,69 | H,CH₃ | —CH₂CH₂— | pyridinium: N-methyl, 3-SO₂NH₂, 5-CH₂SO₃⁻ |
| 70,71 | H,CH₃ | —CH₂CH₂— | pyridinium: N-methyl, 3-CN, 5-CH₂CH₂SO₃⁻ |
| 72 | H | —CH₂CH₂— | pyridinium: N-methyl, 4-NHCH₂SO₃⁻ |
| 73 | H | —CH₂CH₂— | pyridinium: N-methyl, 4-CH₂NHSO₃⁻ |
| 74 | H | —CH₂CH₂— | pyridinium: N-methyl, 4-CONHSO₃⁻ |

-continued

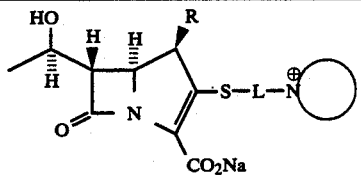

| Compound No. | R | L | |
|---|---|---|---|
| 75 | H | —CH₂CH₂— | (N-methylpyridinium-4-yl)methyl-tetrazolate |
| 76,77 | H,CH₃ | —CH(CH₃)CH₂— | (N-methylpyridinium-4-yl)ethylsulfonate |
| 78,79 | H,CH₃ | —CH₂CH₂— | (N-methylpyridinium-4-yl)methyl-P(=O)(OMe)(O⁻) |
| 80 | H | —CH₂CH₂— | (N-methylpyridinium-4-yl)methyl-P(=O)(OEt)(O⁻) |
| 81 | H | —CH₂CH₂— | (N-methylpyridinium-4-yl)methyl-P(=O)(OH)(O⁻) |
| 82,83 | H,CH₃ | —CH₂CH₂— | (N-methylpyridinium-4-yl)methyl-P(=O)(CH₃)(O⁻) |
| 84,85 | H,CH₃ | —CH₂CH₂— | (N-methylpyridinium-3-yl)methyl-P(=O)(CH₃)(O⁻) |
| 86,87 | H,CH₃ | —CH₂CH₂— | (N-methylpyridinium-3-yl)methyl-P(=O)(OMe)(O⁻) |
| 88,89 | H,CH₃ | —CH₂CH₂— | (N-methyl-3-methylpyridinium-4-yl)methyl-SO₂-N(⁻)-CN |
| 90,91 | H,CH₃ | —CH₂CH₂— | (N-methylpyridinium-3-yl)-SO₂-N(⁻)-C(=N-thienyl)- |

-continued

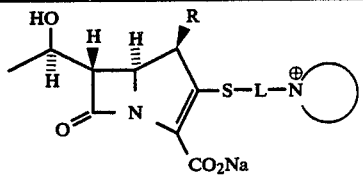

| Compound No. | R | L | |
|---|---|---|---|
| 92,93 | H,CH₃ | —CH₂CH₂— | (4-methylpyridinium-CH₂-SO₂-N⁻-C(=S)-thiazole) |
| 94,95 | H,CH₃ | —CH₂CH₂— | (4-methylpyridinium-CH₂-SO₂-N⁻-C(=S)-NH₂) |
| 96,97 | H,CH₃ | —CH₂CH₂— | (4-methylpyridinium-CH₂-SO₂-N⁻-pyrimidine) |
| 98,99 | H,CH₃ | —CH₂CH₂— | (3-methylpyridinium-CH₂-SO₂-N⁻-thiazole) |
| 100,101 | H,CH₃ | —CH₂CH₂— | (4-methylpyridinium-CH₂-SO₂-N⁻-(5-methylisoxazol-3-yl)) |
| 102,103 | H,CH₃ | —CH₂CH₂— | (1-methylpyridazinium-4-CO₂⁻) |
| 104,105 | H,CH₃ | —CH₂CH₂— | (1-methylpyridazinium-3-CO₂⁻) |
| 106,107 | H,CH₃ | —CH₂CH₂— | (2-methyl-3-methylthiazolium-SO₃⁻) |
| 108,109 | H,CH₃ | —CH₂CH₂— | (N-methyltriazolium-CH₂SO₃⁻) |
| 110 | CH₃ | —CH₂CH₂— | (methylpyrimidinium-CH₂SO₃⁻) |

-continued
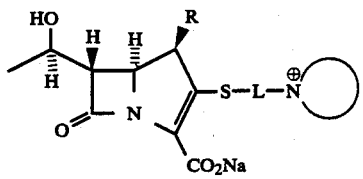
| Compound No. | R | L | 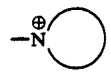 |
|---|---|---|---|
| 111 | H | —CH₂CH₂— | 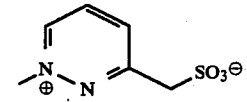 |
| 112 | H | —CH₂CH₂— | 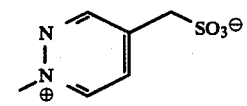 |
| 113 | H | —CH₂CH₂— | 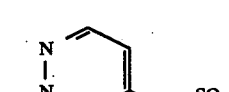 |
| 114 | H | —CH₂CH₂— | 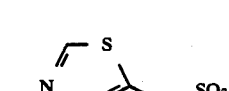 |
| 115 | H | —CH₂CH₂— | 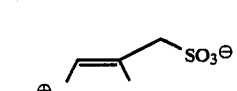 |
| 116,117 | H,CH₃ | —CH₂CH₂— |  |
| 118,119 | H,CH₃ | —CH₂CH₂— | 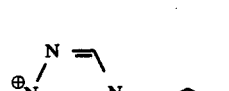 |
| 120 | H | —CH₂CH₂— | 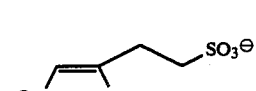 |
| 121,122 | H,CH₃ | —CH₂CH₂— |  |
| 123 | H | —CH₂CH₂— | 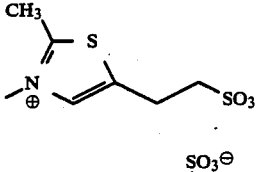 |

-continued

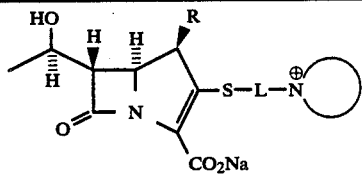

| Compound No. | R | L |  |
|---|---|---|---|
| 124,125 | H,CH₃ | —CH₂CH₂— | (indene-pyridinium with SO₃⁻) |
| 126,127 | H,CH₃ | —CH₂CH₂— | (thienopyridinium with SO₃⁻) |
| 128,129 | H,CH₃ | —CH₂CH₂— | (hydroxyquinolinium with SO₃⁻) |
| 130,131 | H,CH₃ | —CH₂CH₂— | (aminopyridinium-CH₂SO₂N⁻CN) |
| 132 | CH₃ | —CH₂CH₂— | (fluoropyridinium-CH₂SO₂N⁻CN) |
| 133 | CH₃ | —CH₂CH₂— | (chloropyridinium-CH₂SO₂N⁻CN) |

What is claimed is:
1. A compound of the formula:

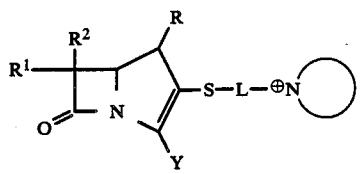

(I.)

wherein:
R is H or CH₃;
R¹ is CH₃CH(OH)—;
R² is H;

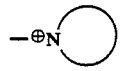

is a quaternary, monocyclic, substituted heteroary group comprising pyridinium, which is required to be substituted in the 4-position by an acidic sidechain of the structure —B, where B is optionally attached by way of a bridging group which is a member selected from the group consisting essentially of —CH₂—; and B is an acidic function which is a member selected from the group consisting essentially of sulfo (SO₃H); SO₂NHCN; and heteroarylsulfonamino (SO₂NHR$^x$), where R$^x$ is substituted or unsubstituted heteroaryl, selected from thiazole and thiadiazole; and where the heteroaryl group is substituted, it is mono- or disubstituted by a member or members independently selected from the group consisting essentially of C₁-C₄alkyl; CF₃; carbamoyl, and cyano;

the heteroaryl group

is optionally substituted by one to three of the radicals independently selected from the group consisting of:
(a) a trifluoromethyl group; —CF₃;
(b) a halogen atom: —Br, —Cl —F, or —I;
(c) C₁-C₄ alkoxy radical; —OC₁₋₄ alkyl;
(d) a hydroxy group: —OH;
(e) an amino group, or a mono (C₁C₄ alkyl) amino or di(C₁-C₄ alkyl) amino group:

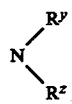

where R$^y$ and R$^z$ are independently H or C₁-C₄alkyl;
(f) C₁-C₆ alkyl radical; and L is —CH₂CH₂—; and Y is is selected from;
(i) COOH or a pharmaceutically acceptable thereof;
(ii) COOM wherein M is an alkali metal or other pharmaceutically acceptable salt; and
(iii) COOM where M is a negative charge in the case where a permanent positive charge exists elsewhere in the molecule.

2. A compound according to claim 1 wherein the

group with the acidic sidechain and optional substituent is selected from the group consisted of:

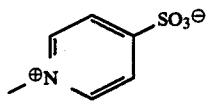 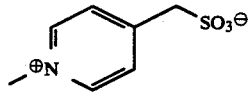

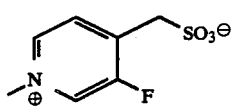

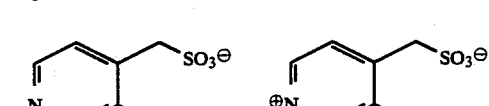
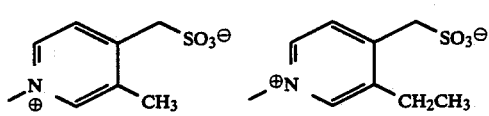
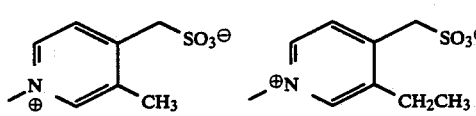

-continued

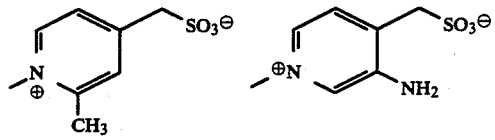

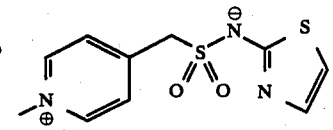

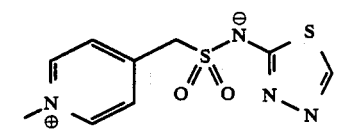

3. A compound according to claim 1 wherein the acidic sidechain B is SO₃H, CH₂SO₃H, or CH₂SO₂NHCN, while the optional substituent thereon is selected from the group consisting of: Cl and F.

4. The compounds

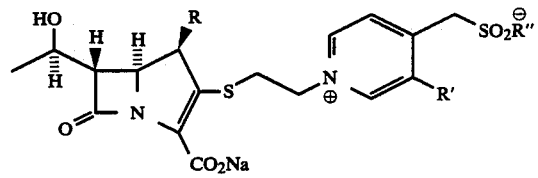

wherein R =H, CH₃; R'=H, F, Cl; and R"=O or NCN.

5. A compound selected from the group consisting of

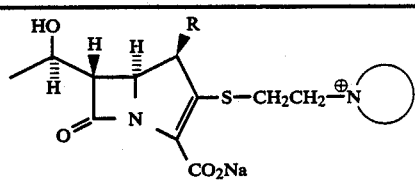

| Compound No. | R | |
|---|---|---|
| 1 | H |  |
| 2 | H | 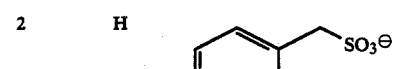 |
| 5 | H | 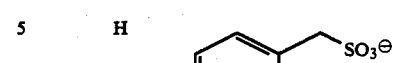 |

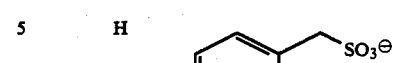

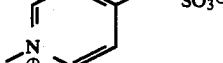

-continued

[Structure: carbapenem core with HO-CH(H)-CH3 group, R substituent, S-CH2CH2-N⊕(ring), CO2Na]

⊖N⊕(ring)

| Compound No. | R | (substituent) |
|---|---|---|
| 6 | H | 4-(SO3⊖-CH2)-3-methyl-N-methylpyridinium |
| 7 | H | 4-(SO3⊖-CH2)-3-fluoro-N-methylpyridinium |
| 8 | H | 4-(SO3⊖-CH2)-3-chloro-N-methylpyridinium |
| 9 | H | 4-(SO3⊖-CH2)-3-bromo-N-methylpyridinium |
| 10 | H | 4-(SO3⊖-CH2)-3-amino-N-methylpyridinium |
| 11 | H | 4-(SO3⊖-CH2)-3-methoxy-N-methylpyridinium |
| 14 | H | 4-[CH2-S(O)2-N⊖-C(=S)-N=CH-CH=] N-methylpyridinium (thiazoline) |
| 15 | H | 4-[CH2-S(O)2-N⊖-C(=S)-N=N-CH=] N-methylpyridinium (thiadiazoline) |
| 16 | CH3 | 4-SO3⊖-N-methylpyridinium |
| 17 | CH3 | 4-(CH2-SO3⊖)-N-methylpyridinium |

-continued

[Structure: same carbapenem core]

⊖N⊕(ring)

| Compound No. | R | (substituent) |
|---|---|---|
| 19 | CH3 | 4-(SO3⊖-CH2)-3-fluoro-N-methylpyridinium |
| 20 | CH3 | 4-(SO3⊖-CH2)-3-chloro-N-methylpyridinium |
| 21 | CH3 | 4-[CH2-S(O)2-N⊖-C(=S)-N=CH-CH=] N-methylpyridinium |
| 22 | CH3 | 4-[CH2-S(O)2-N⊖-C(=S)-N=N-CH=] N-methylpyridinium |
| 24 | H | 4-(SO2NCN⊖)-N-methylpyridinium |
| 25 | H | 4-(SO2NCN⊖-CH2)-3-fluoro-N-methylpyridinium |
| 26 | H | 4-(SO2NCN⊖-CH2)-3-chloro-N-methylpyridinium |
| 27 | CH3 | 4-(SO2NCN⊖-CH2)-N-methylpyridinium |
| 28 | CH3 | 4-(SO2NCN⊖-CH2)-3-fluoro-N-methylpyridinium |
| 29 | CH3 | 4-(SO2NCN⊖-CH2)-3-chloro-N-methylpyridinium |

6. A pharmaceutical composition for antibacterial use comprising an antibacterially effective amount of a compound of claim 1 and a pharmaceutically acceptable carrier thereof.

7. A method of treating bacterial infections in human or animal subjects in need of such treatment comprising adminstering to such subject an antibacterially effective amount of a compound of claim 1.

8. The combination of a compound of claim 1 and a DHP inhibitor.

9. The combination of a compound of claim 4 and the DHP inhibitor 7-(L-2-amino-2-carboxyethylthio)-2-(2,2-dimethylcyclopropanecarboxamide)-2-heptanoic acid.

10. A pharmaceutical composition for antibacterial use comprising an antibacterially effective amount of a compound of claim 1 an inhibitorily effective amount of a DHF inhibitor, and a pharmaceutically acceptable carrier thereof.

11. A pharmaceutical composition according to claim 10 wherein the DHP inhibitor is 7-(L-2-amino-2-carboxyethylthio)-2 (2,2-dimethylcyclopropanecarboxyamide)-2-heptanoic acid.

12. A method of treating bacterial infections in human or animal subjects in need of such treatment comprising coadminstering to such subject an antibacterially effective amount of a compound of claim 1 and an inhibitorily effective amount of a DHP inhibitor.

13. A method according to claim 12 wherein the DHP inhibitor is 7-(L-2-amino-2-carboxyethylthio)-2-(2,2-dimethylcyclopropanecarboxamide)-2-heptanoic acid.

* * * * *